(12) United States Patent
Kanematsu et al.

(10) Patent No.: US 10,710,989 B2
(45) Date of Patent: Jul. 14, 2020

(54) METHOD FOR PRODUCING HETEROCYCLIC COMPOUND

(71) Applicant: TAKEDA PHARMACEUTICAL COMPANY LIMITED, Osaka (JP)

(72) Inventors: Makoto Kanematsu, Osaka (JP); Kazuhisa Ishimoto, Osaka (JP); Tomoaki Katou, Osaka (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 16/488,770

(22) PCT Filed: Feb. 27, 2018

(86) PCT No.: PCT/JP2018/007349
§ 371 (c)(1),
(2) Date: Aug. 26, 2019

(87) PCT Pub. No.: WO2018/159639
PCT Pub. Date: Sep. 7, 2018

(65) Prior Publication Data
US 2019/0375736 A1    Dec. 12, 2019

(30) Foreign Application Priority Data
Feb. 28, 2017 (JP) .................. 2017-036898

(51) Int. Cl.
C07D 405/14 (2006.01)
C07D 231/12 (2006.01)
C07D 405/10 (2006.01)

(52) U.S. Cl.
CPC ......... *C07D 405/14* (2013.01); *C07D 231/12* (2013.01); *C07D 405/10* (2013.01)

(58) Field of Classification Search
None
See application file for complete search history.

(56) References Cited

U.S. PATENT DOCUMENTS

| | | |
|---|---|---|
| 2015/0307451 A1 | 10/2015 | Yamada et al. |
| 2016/0152598 A1 | 6/2016 | Yamada et al. |
| 2016/0152603 A1 | 6/2016 | Yamada et al. |
| 2017/0027921 A1 | 2/2017 | Yamada et al. |
| 2017/0044143 A1 | 2/2017 | Yamada et al. |
| 2017/0100373 A1 | 4/2017 | Yamada et al. |
| 2017/0100384 A1 | 4/2017 | Yamada et al. |
| 2017/0216255 A1 | 8/2017 | Yamada et al. |
| 2017/0258764 A1 | 9/2017 | Yamada et al. |
| 2017/0266162 A1 | 9/2017 | Yamada et al. |
| 2018/0000780 A1 | 1/2018 | Yamada et al. |
| 2018/0346452 A1 | 12/2018 | Yamada et al. |
| 2019/0083467 A1 | 3/2019 | Ogino et al. |

FOREIGN PATENT DOCUMENTS

| | | |
|---|---|---|
| JP | 55-141457 | 11/1980 |
| SU | 1502568 | 8/1989 |
| WO | 2015/163485 | 10/2015 |
| WO | 2017/155050 | 9/2017 |

OTHER PUBLICATIONS

International Search Report dated May 22, 2018 in International (PCT) Application No. PCT/JP2018/007349.
Uno et al., "1-[4-(N-Benzylamino)phenyl]-3-phenylurea derivatives as a new class of hypoxia-inducible factor-1α Inhibitors", Bioorganic & Medicinal Chemistry Letters, vol. 19, 2009, pp. 3166-3169.
Nayal et al., "Synthesis of tertiary arylamines: Lewis acid-catalyzed direct reductive N-alkylation of secondary amines with ketones through an alternative pathway", Chemical Communications, vol. 52, No. 62, 2016, pp. 9648-9651.

*Primary Examiner* — Alicia L Otton

(74) *Attorney, Agent, or Firm* — Wenderoth, Lind & Ponack, L.L.P.

(57) ABSTRACT

The present invention provides a method of producing a heterocyclic compound useful as an agent for the prophylaxis and/or treatment of Alzheimer's disease and the like. The present invention relates to a method of producing 1,5-anhydro-2,4-dideoxy-2-(4-fluoro-5-methyl-1-oxo-6-(4-(1H-pyrazol-1-yl)benzyl)-1,3-dihydro-2H-isoindol-2-yl)-L-threo-pentitol or a salt thereof, which comprises reacting 4-fluoro-3-hydroxy-5-methyl-6-[4-(1H-pyrazol-1-yl)benzyl]-2-benzofuran-1(3H)-one or a salt thereof, 3-fluoro-2-formyl-4-methyl-5-[4-(1H-pyrazol-1-yl)benzyl]benzoic acid or a salt thereof, or a mixture thereof, with 2-amino-1,5-anhydro-2,4-dideoxy-L-threo-pentitol.

17 Claims, 1 Drawing Sheet

[Figure 1]
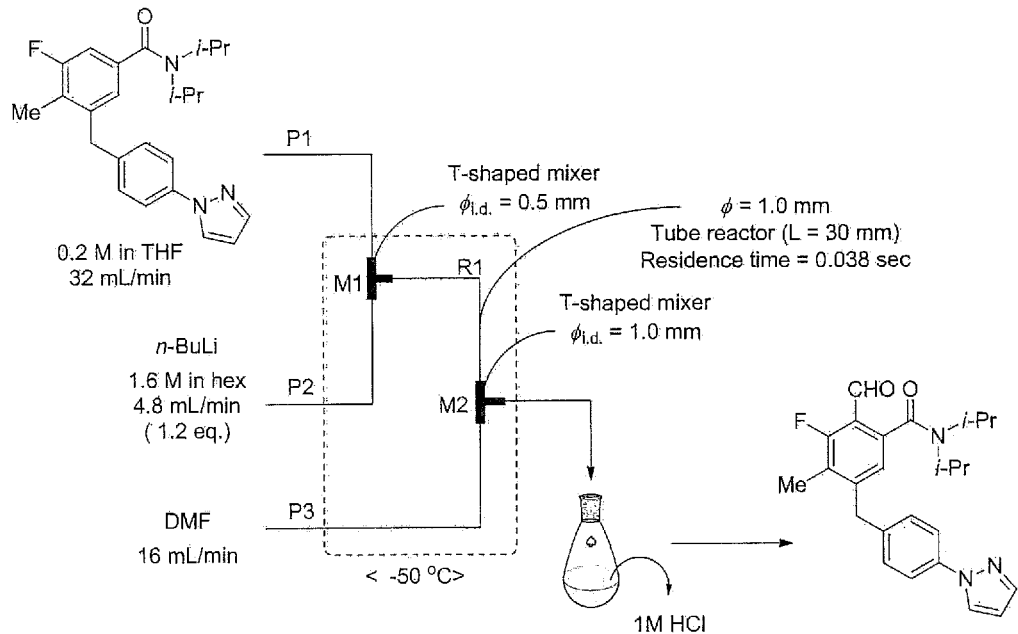
[Figure 2]
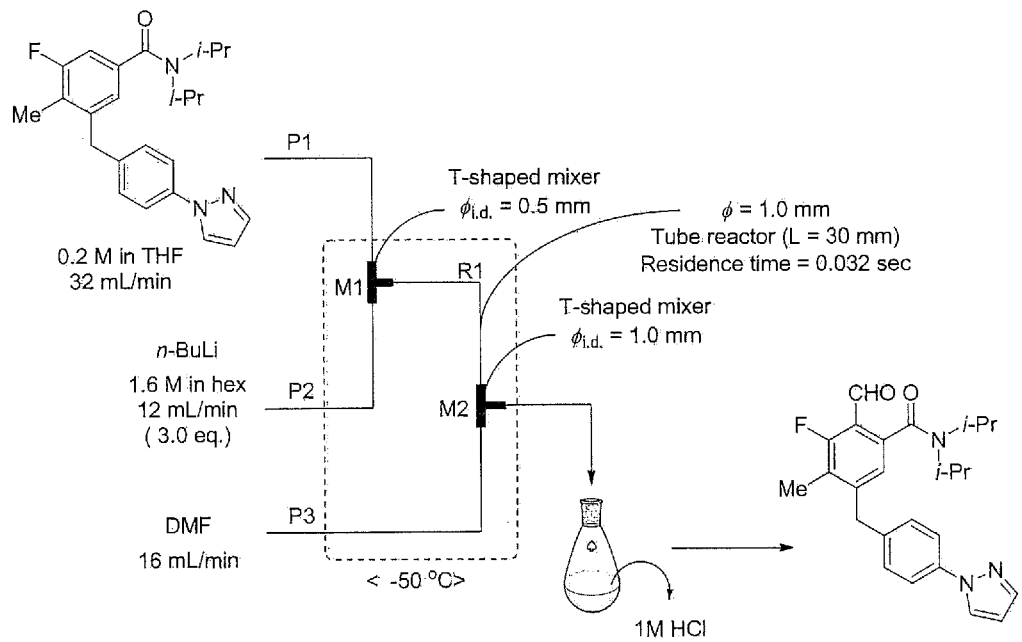

METHOD FOR PRODUCING HETEROCYCLIC COMPOUND

TECHNICAL FIELD

The present invention relates to a method of producing a heterocyclic compound useful for the prophylaxis and/or treatment of Alzheimer's disease and the like.

BACKGROUND OF THE INVENTION 1,5-Anhydro-2,4-dideoxy-2-(4-fluoro-5-methyl-1-oxo-6-(4-(1H-pyrazol-1-yl)benzyl)-1,3-dihydro-2H-isoindol-2-yl)-L-threo-pentitol is known to be useful as an agent for the prophylaxis and/or treatment of Alzheimer's disease and the like (Patent Document 1).

DOCUMENT LIST

Patent Document

Patent Document 1: WO 2015/163485

SUMMARY OF THE INVENTION

Problems to be Solved by the Invention

The aim of the present invention is to provide a method of producing 1,5-anhydro-2,4-dideoxy-2-(4-fluoro-5-methyl-1-oxo-6-(4-(1H-pyrazol-1-yl)benzyl)-1,3-dihydro-2H-isoindol-2-yl)-L-threo-pentitol, without using a highly poisonous reagent, in an efficient way (e.g., in short steps, in high-yield, in a highly selective manner).

Means of Solving the Problems

The present inventors have conducted intensive studies in an attempt to solve the above-mentioned problems and found that 1,5-anhydro-2,4-dideoxy-2-(4-fluoro-5-methyl-1-oxo-6-(4-(1H-pyrazol-1-yl)benzyl)-1,3-dihydro-2H-isoindol-2-yl)-L-threo-pentitol can produced without using a highly poisonous reagent, in an efficient way (e.g., in short steps, in high-yield, in a highly selective manner), which resulted in the completion of the present invention.

Accordingly, the present invention provides the following.

[1] A method of producing 1,5-anhydro-2,4-dideoxy-2-(4-fluoro-5-methyl-1-oxo-6-(4-(1H-pyrazol-1-yl)benzyl)-1,3-dihydro-2H-isoindol-2-yl)-L-threo-pentitol or a salt thereof (herein sometimes to be referred to as "compound A"), which comprises reacting 4-fluoro-3-hydroxy-5-methyl-6-[4-(1H-pyrazol-1-yl)benzyl]-2-benzofuran-1(3H)-one or a salt thereof, 3-fluoro-2-formyl-4-methyl-5-[4-(1H-pyrazol-1-yl)benzyl]benzoic acid or a salt thereof, or a mixture thereof (herein sometimes to be referred to as "PHBO") with 2-amino-1,5-anhydro-2,4-dideoxy-L-threo-pentitol (herein sometimes to be referred to as "ATHP").

[2] A method of producing PHBO, which comprises subjecting a compound represented by the formula (I)

(I)

wherein $R^1$ and $R^2$ are each independently a hydrogen atom or an optionally substituted hydrocarbon group, or $R^1$ and $R^2$ form, together with the adjacent nitrogen atom, a 3- to 8-membered monocyclic nitrogen-containing non-aromatic heterocycle, or a salt thereof (herein sometimes to be referred to as "compound (I)"), to a hydrolysis reaction.

[3] A method of producing compound (I), which comprises subjecting a compound represented by the formula (II)

(II)

wherein $R^1$ and $R^2$ are each independently a hydrogen atom or an optionally substituted hydrocarbon group, or $R^1$ and $R^2$ form, together with the adjacent nitrogen atom, a 3- to 8-membered monocyclic nitrogen-containing non-aromatic heterocycle, or a salt thereof (herein sometimes to be referred to as "compound (II)"), to a formylation reaction.

[4] A method of producing PHBO, which comprises

Step (i): a step of subjecting compound (II) to a formylation reaction to obtain compound (I), and Step (ii): a step of subjecting compound (I) to a hydrolysis reaction.

[5] A method of producing compound A, which comprises

Step (i): a step of subjecting compound (II) to a formylation reaction to obtain compound (I), Step (ii): a step of subjecting compound (I) to a hydrolysis reaction to obtain PHBO, and Step (iii): a step of reacting PHBO with ATHP.

[6] 4-Fluoro-3-hydroxy-5-methyl-6-[4-(1H-pyrazol-1-yl)benzyl]-2-benzofuran-1(3H)-one or a salt thereof.

[7] 3-Fluoro-2-formyl-4-methyl-5-[4-(1H-pyrazol-1-yl)benzyl]benzoic acid or a salt thereof.

[8] 3-Fluoro-2-formyl-4-methyl-N,N-di(propan-2-yl)-5-[4-(1H-pyrazol-1-yl)benzyl]benzamide or a salt thereof.

[9] 3-Fluoro-4-methyl-N,N-di(propan-2-yl)-5-[4-(1H-pyrazol-1-yl)benzyl]benzamide or a salt thereof.

[10] A method of producing PHBO, which comprises subjecting a compound represented by the formula (VIII)

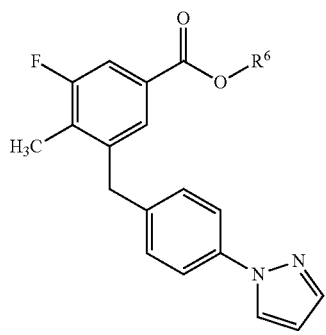

(VIII)

wherein $R^6$ is a hydrogen atom or an optionally substituted $C_{1-6}$ alkyl group, or a salt thereof (herein sometimes to be referred to as "compound (VIII)"), to a formylation reaction, and then a hydrolysis reaction, if desired.

[11] A method of producing compound (VIII), which comprises subjecting a compound represented by the formula (IX)

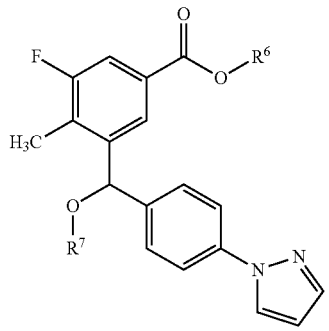

(IX)

wherein $R^6$ is a hydrogen atom or an optionally substituted $C_{1-6}$ alkyl group, and $R^7$ is a protecting group, or a salt thereof (herein sometimes to be referred to as "compound (IX)"), to a reduction reaction.

[12] A method of producing compound (IX), which comprises subjecting a compound represented by the formula (X)

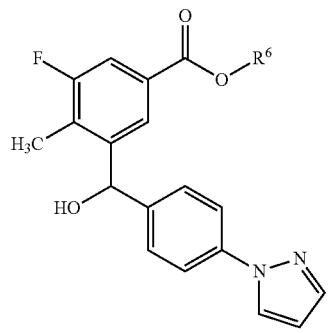

(X)

wherein $R^6$ is a hydrogen atom or an optionally substituted $C_{1-6}$ alkyl group.

or a salt thereof (herein sometimes to be referred to as "compound (X)"), to a protection reaction of the hydroxy group.

[13] A method of producing compound (X), which comprises reacting a compound represented by the formula (XI)

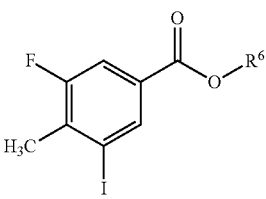

(XI)

wherein $R^6$ is a hydrogen atom or an optionally substituted $C_{1-6}$ alkyl group.

or a salt thereof (herein sometimes to be referred to as "compound (XI)"), with 4-(1H-pyrazol-1-yl)benzaldehyde.

[14] A method of producing compound (IX), which comprises

Step (i): a step comprising reacting compound (XI) with 4-(1H-pyrazol-1-yl)benzaldehyde to obtain compound (X), and Step (ii): a step of subjecting compound (X) to a protection reaction of the hydroxy group.

[15] A method of producing compound (VIII), which comprises

Step (i): a step of reacting compound (XI) with 4-(1H-pyrazol-1-yl)benzaldehyde to obtain compound (X), Step (ii): a step of subjecting compound (X) to a protection reaction of the hydroxy group to obtain compound (IX), and Step (iii): a step of subjecting compound (IX) to a reduction reaction.

[16] A method of producing PHBO, which comprises

Step (i): a step of reacting compound (XI) with 4-(1H-pyrazol-1-yl)benzaldehyde to obtain compound (X), Step (ii): a step of subjecting compound (X) to a protection reaction of the hydroxy group to obtain compound (IX), Step (iii): a step of subjecting compound (IX) to a reduction reaction to obtain compound (VIII), and Step (iv): a step of subjecting compound (VIII) to a formylation reaction, and then a hydrolysis reaction, if desired.

[17] A method of producing compound A, which comprises

Step (i): a step comprising reacting compound (XI) with 4-(1H-pyrazol-1-yl)benzaldehyde to obtain compound (X), Step (ii): a step of subjecting compound (X) to a protection reaction of the hydroxy group to obtain compound (IX), Step (iii): a step of subjecting compound (IX) to a reduction reaction to obtain compound (VIII),
Step (iv): a step of subjecting compound (VIII) to a formylation reaction, and then a hydrolysis reaction, if desired, to obtain PHBO, and
Step (v): a step of reacting PHBO with ATHP.

Effect of the Invention

According to the present invention, 1,5-anhydro-2,4-dideoxy-2-(4-fluoro-5-methyl-1-oxo-6-(4-(1H-pyrazol-1-yl)benzyl)-1,3-dihydro-2H-isoindol-2-yl)-L-threo-pentitol, which is useful for the prophylaxis and/or treatment of Alzheimer's disease and the like, can produced without using a highly poisonous reagent, in an efficient way (e.g., in short steps, in high-yield, in a highly selective manner).

Examples of the highly poisonous reagent include stannum and osmium. In the present invention, the risk associated with the use of these reagents (e.g., exposure risk of manufacturer of objective product, contamination risk of objective product) can be avoided.

BRIEF DESCRIPTION OF THE DRAWINGS

FIG. 1 is a schematic view showing a reaction apparatus (flow reactor) used in Example 8. In the figure, Me means a methyl group, and i-Pr means an isopropyl group.

FIG. 2 is a schematic view showing a reaction apparatus (flow reactor) used in Example 9. In the figure, Me means a methyl group, and i-Pr means an isopropyl group.

DETAILED DESCRIPTION OF THE INVENTION

The present invention is explained in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "C$_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-C$_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-C$_{7-16}$ aralkyl-carbamoyl group" include benzylcarbamoyl and phenethylcarbamoyl.

In the present specification, examples of the "C$_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated C$_{1-6}$ alkylsulfonyl group" include a C$_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and -hexylsulfonyl.

In the present specification, examples of the "C$_{6-14}$ arylsulfonyl group" include phenylsulfonyl, 1-naphthylsulfonyl and 2-naphthylsulfonyl.

In the present specification, examples of the "hydrocarbon group" (including "hydrocarbon group" of "optionally substituted hydrocarbon group") include a C$_{1-6}$ alkyl group, a C$_{2-6}$ alkenyl group, a C$_{2-6}$ alkynyl group, a C$_{3-10}$ cycloalkyl group, a C$_{3-10}$ cycloalkenyl group, a C$_{6-14}$ aryl group and a C$_{7-16}$ aralkyl group.

In the present specification, examples of the "optionally substituted hydrocarbon group" include a hydrocarbon group optionally having substituent(s) selected from the following Substituent group A.

[Substituent group A]
(1) a halogen atom,
(2) a nitro group,
(3) a cyano group,
(4) an oxo group,
(5) a hydroxy group,
(6) an optionally halogenated C$_{1-6}$ alkoxy group,
(7) a C$_{6-14}$ aryloxy group (e.g., phenoxy, naphthoxy),
(8) a C$_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a C$_{1-6}$ alkyl-carbonyloxy group (e.g., acetoxy, propanoyloxy),
(12) a C$_{6-14}$ aryl-carbonyloxy group (e.g., benzoyloxy, 1-naphthoyloxy, 2-naphthoyloxy),
(13) a C$_{1-6}$ alkoxy-carbonyloxy group (e.g., methoxycarbonyloxy, ethoxycarbonyloxy, propoxycarbonyloxy, butoxycarbonyloxy),
(14) a mono- or di-C$_{1-6}$ alkyl-carbamoyloxy group (e.g., methylcarbamoyloxy, ethylcarbamoyloxy, dimethylcarbamoyloxy, diethylcarbamoyloxy),
(15) a C$_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated C$_{1-6}$ alkylsulfonyloxy group (e.g., methylsulfonyloxy, trifluoromethylsulfonyloxy),
(19) a C$_{6-14}$ arylsulfonyloxy group optionally substituted by a C$_{1-6}$ alkyl group (e.g., phenylsulfonyloxy, toluenesulfonyloxy),
(20) an optionally halogenated C$_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated C$_{1-6}$ alkyl-carbonyl group,
(26) a C$_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a C$_{1-6}$ alkoxy-carbonyl group,
(30) a C$_{6-14}$ aryloxy-carbonyl group (e.g., phenyloxycarbonyl, 1-naphthyloxycarbonyl, 2-naphthyloxycarbonyl),
(31) a C$_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-C$_{1-6}$ alkyl-carbamoyl group,
(35) a C$_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated C$_{1-6}$ alkylsulfonyl group,
(39) a C$_{6-14}$ arylsulfonyl group,
(40) a 5- to 14-membered aromatic heterocyclylsulfonyl group (e.g., pyridylsulfonyl, thienylsulfonyl),
(41) an optionally halogenated C$_{1-6}$ alkylsulfinyl group,
(42) a C$_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-C$_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-C$_{6-14}$ arylamino group (e.g., phenylamino),
(47) a 5- to 14-membered aromatic heterocyclylamino group (e.g., pyridylamino),
(48) a C$_{7-16}$ aralkylamino group (e.g., benzylamino),
(49) a formylamino group,
(50) a C$_{1-6}$ alkyl-carbonylamino group (e.g., acetylamino, propanoylamino, butanoylamino),
(51) a (C$_{1-6}$ alkyl) (C$_{1-6}$ alkyl-carbonyl)amino group (e.g., N-acetyl-N-methylamino),
(52) a C$_{6-14}$ aryl-carbonylamino group (e.g., phenylcarbonylamino, naphthylcarbonylamino),
(53) a C$_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a C$_{7-16}$ aralkyloxy-carbonylamino group (e.g., benzyloxycarbonylamino),

(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and
8- to 14-membered fused polycyclic (preferably bi- or tri-cyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi- or tri-cyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

The definition of each symbol in the formulas (I), (II) and (VIII)-(XI) is explained below in detail.

$R^1$ and $R^2$ are each independently a hydrogen atom or an optionally substituted hydrocarbon group, or $R^1$ and $R^2$ form, together with the adjacent nitrogen atom, a 3- to 8-membered monocyclic nitrogen-containing non-aromatic heterocycle.

The "optionally substituted hydrocarbon group" represented by $R^1$ or $R^2$ is preferably a $C_{1-6}$ alkyl group (e.g., methyl, ethyl, isopropyl, tert-butyl), a $C_{3-10}$ cycloalkyl group, a $C_{6-14}$ aryl group (e.g., phenyl) or a $C_{7-16}$ aralkyl group, more preferably a $C_{1-6}$ alkyl group, still more preferably isopropyl.

Preferable examples of the "3- to 8-membered monocyclic nitrogen-containing non-aromatic heterocycle" formed by $R^1$ and $R^2$ together with the adjacent nitrogen atom include a pyrrolidine ring, a piperidine ring, a morpholine ring and the like.

$R^1$ and $R^2$ are preferably each independently a hydrogen atom, a $C_{1-6}$ alkyl group (preferably methyl, ethyl, isopropyl, tert-butyl) or a $C_{6-14}$ aryl group (preferably phenyl), or $R^1$ and $R^2$ form, together with the adjacent nitrogen atom, a 3- to 8-membered monocyclic nitrogen-containing non-aromatic heterocycle (preferably a pyrrolidine ring). $R^1$ and $R^2$ are more preferably each independently a $C_{1-6}$ alkyl group (preferably methyl, ethyl, isopropyl, tert-butyl), still more preferably both isopropyl.

In compound (I), when one of $R^1$ and $R^2$ is a hydrogen atom, as shown below, the formyl group and the amido group can be bonded to each other to form a closed ring structure. A compound having such a closed ring structure is also encompassed in compound (I).

Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzyl ethylene diamine and the like.

Preferable examples of the salt with inorganic acid include salts with hydrofluoric acid, hydrochloric acid, hydrobromic acid, hydroiodic acid, nitric acid, sulfuric acid, sulfurous acid, phosphoric acid, phosphorus acid, carbonic acid, bicarbonic acid and the like.

Preferable examples of the salt with organic acid include salts with carboxylic acids (i.e., organic compounds having 1 or more carboxy groups; the specific examples thereof include formic acid, acetic acid, benzoic acid, trifluoroacetic acid, phthalic acid, fumaric acid, oxalic acid, tartaric acid, maleic acid, citric acid, succinic acid, malic acid and the like); and sulfonic acids (i.e., organic compounds having 1 or more sulfo groups; the specific examples thereof include

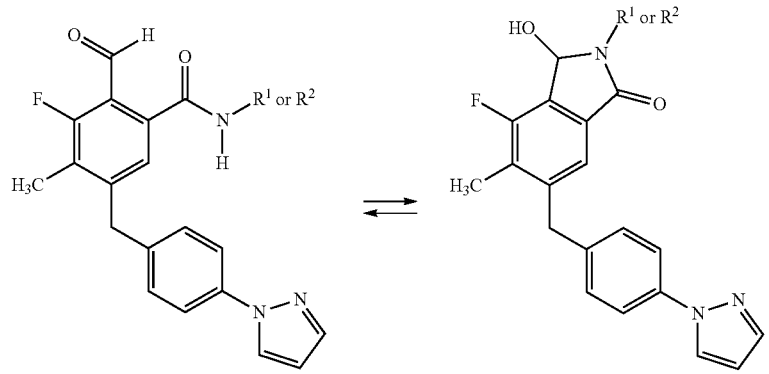

wherein the symbols are as defined above.

In preferable embodiment,
compound (I) is 3-fluoro-2-formyl-4-methyl-N,N-di(propan-2-yl)-5-[4-(1H-pyrazol-1-yl)benzyl]benzamide or a salt thereof, preferably 3-fluoro-2-formyl-4-methyl-N,N-di(propan-2-yl)-5-[4-(1H-pyrazol-1-yl)benzyl]benzamide, and compound (II) is 3-fluoro-4-methyl-N,N-di(propan-2-yl)-5-[4-(1H-pyrazol-1-yl)benzyl]benzamide or a salt thereof, preferably 3-fluoro-4-methyl-N,N-di(propan-2-yl)-5-[4-(1H-pyrazol-1-yl)benzyl]benzamide.

$R^6$ is a hydrogen atom or an optionally substituted $C_{1-6}$ alkyl group.

The "optionally substituted $C_{1-6}$ alkyl group" represented by $R^6$ is preferably a $C_{1-6}$ alkyl group (e.g., ethyl, tert-butyl), more preferably tert-butyl.

$R^7$ is a protecting group.

Examples of the "protecting group" represented by $R^7$ include those employed generally as a protecting of group hydroxy group in the field. The "protecting group" represented by $R^7$ is preferably a $C_{1-6}$ alkyl-carbonyl group (e.g., methylcarbonyl), more preferably methylcarbonyl.

When compound (I), compound (II) or compound (VIII)-(XI) is in the form of a salt, examples of such salt include metal salts, an ammonium salt, salts with organic base, salts with inorganic acid, salts with organic acid, and salts with basic or acidic amino acid.

Preferable examples of the metal salt include alkali metal salts such as sodium salt, potassium salt and the like; alkaline-earth metal salts such as calcium salt, magnesium salt, barium salt and the like; an aluminium salt and the like.

methanesulfonic acid, trifluoromethanesulfonic acid, benzenesulfonic acid, p-toluenesulfonic acid, camphorsulfonic acid and the like).

Preferable examples of the salt with basic amino acid include salts with arginine, lysine, ornithine and the like. Preferable examples of the salt with acidic amino acid include salts with aspartic acid, glutamic acid and the like.

Compound (I), compound (II) and compounds (VIII)-(XI) may contain isomers such as enantiomer or diastereomer and the like. All of such isomers and mixtures thereof are also encompassed in compounds (I), (II) and (VIII)-(XI). In addition, when compound (I), compound (II) and compounds (VIII)-(XI) may contain isomers due to conformation or tautomerism, such isomers and mixtures thereof are also encompassed in compounds (I), (II) and (VIII)-(XI).

Compound (I), compound (II) and compounds (VIII)-(XI) may be each a solvate (e.g., a hydrate, an ethanolate, etc.) or a non-solvate (e.g., a non-hydrate, etc.), and both are encompassed in compounds (I), (II) and (VIII)-(XI).

Compounds labeled an isotope (e.g., $^2H$, $^3H$, $^{11}C$, $^{14}C$, $^8F$, $^{35}S$, $^{125}I$ and the like) and the like are also encompassed in compound (I), compound (II) and compounds (VIII)-(XI).

The production method of the present invention is explained in detail below.
(Production Method A)

The present invention is a method of producing compound A, which comprises reacting PHBO with ATHP.

The scheme of the above-mentioned reaction is shown below (hereinafter to be referred to as Step (iii)).

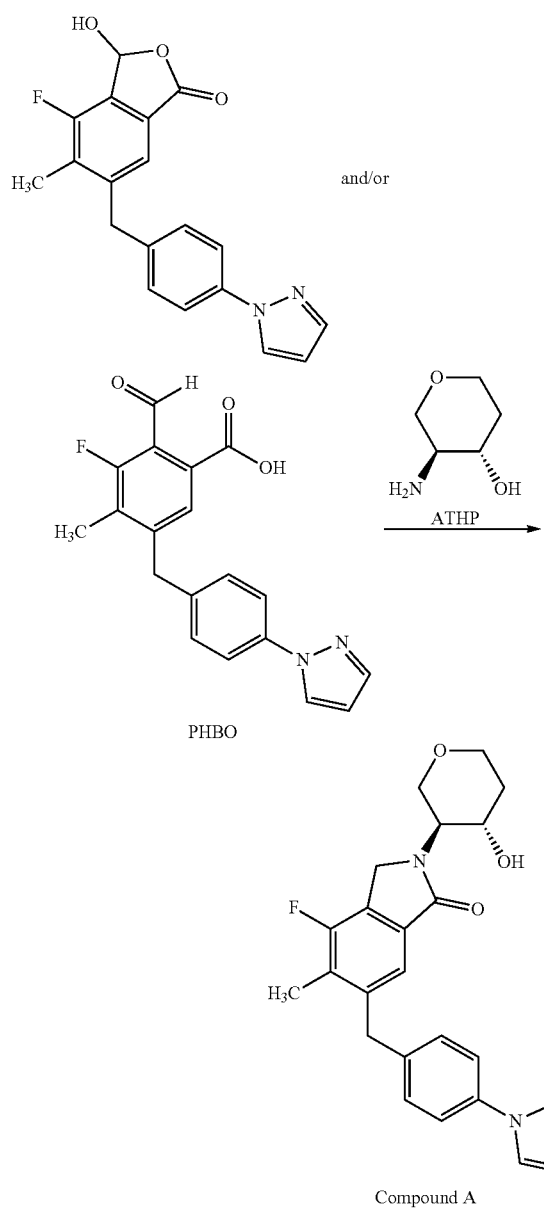

PHBO

Compound A

Step (iii) corresponds to Step 06 in the below-mentioned production method.

As PHBO, 4-fluoro-3-hydroxy-5-methyl-6-[4-(1H-pyrazol-1-yl)benzyl]-2-benzofuran-1(3H)-one or a salt thereof, 3-fluoro-2-formyl-4-methyl-5-[4-(1H-pyrazol-1-yl)benzyl]benzoic acid or a salt thereof, and a mixture thereof at an any ratio can be used. Examples of the salt include those exemplified as the salt of compound (I) or (II).

PHBO is preferably 3-fluoro-2-formyl-4-methyl-5-[4-(1H-pyrazol-1-yl)benzyl]benzoic acid or a salt thereof, more preferably 3-fluoro-2-formyl-4-methyl-5-[4-(1H-pyrazol-1-yl)benzyl]benzoic acid 1,4-diazabicyclo[2.2.2]octane salt.

Examples of the salt of compound A include pharmaceutically acceptable salts, from among those exemplified as the salt of compound (I) and the like. Compound A is preferably 1,5-anhydro-2,4-dideoxy-2-(4-fluoro-5-methyl-1-oxo-6-(4-(1H-pyrazol-1-yl)benzyl)-1,3-dihydro-2H-isoindol-2-yl)-L-threo-pentitol.

(Production Method B).

The present invention also relates to a method of producing PHBO, which comprises subjecting compound (I) to a hydrolysis reaction.

The scheme of the above-mentioned reaction is shown below (hereinafter to be referred to as Step (ii)).

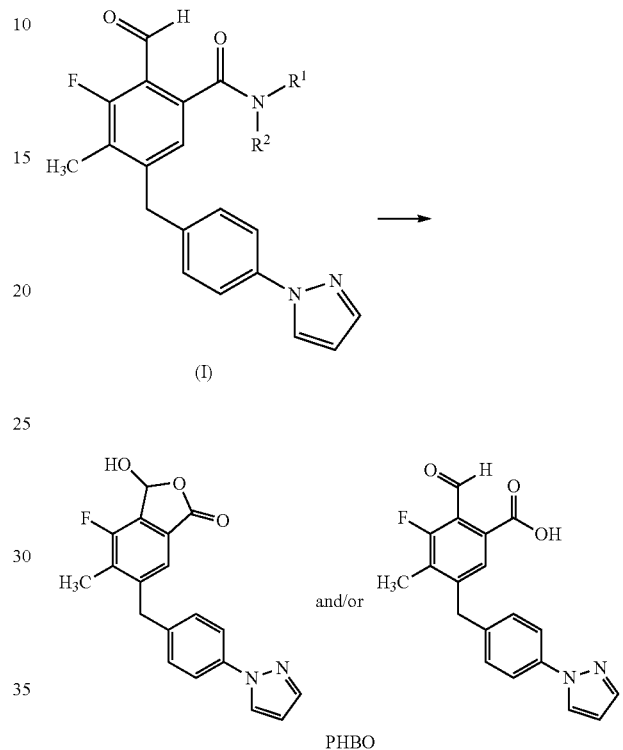

(I)

PHBO wherein the symbols are as defined above.

Step (ii) corresponds to Step 05 in the below-mentioned production method.

(Production Method C)

The present invention also relates to a method of producing compound (I), which comprises subjecting compound (II) to a formylation reaction.

The scheme of the above-mentioned reaction is shown below (hereinafter to be referred to as Step (i)).

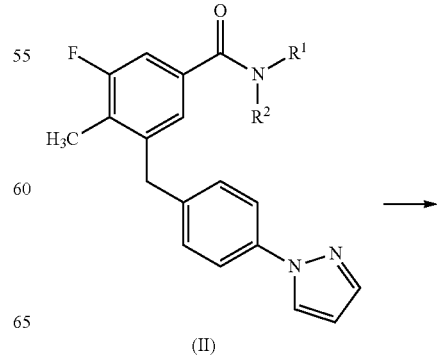

(II)

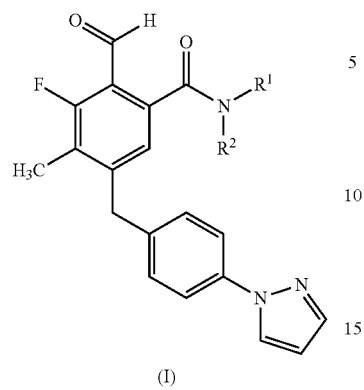

(I)

wherein the symbols are as defined above.

Step (i) corresponds to Step 04 (including Step 04-1) in the below-mentioned production method.

Another embodiment of Step (i) is a continuous production method, which comprises subjecting compound (II) to a formylation reaction in a flow reactor.

(Production Method D)

The present invention also relates to a method of producing PHBO, which comprises Step (i): a step of subjecting compound (II) to a formylation reaction to obtain compound (I) and Step (ii): a step of subjecting compound (I) to a hydrolysis reaction.

The scheme of the above-mentioned reaction is shown below.

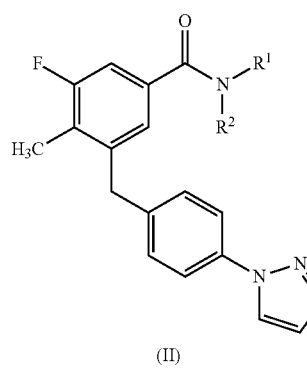

(II)

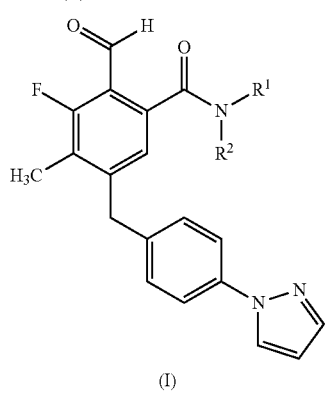

(I)

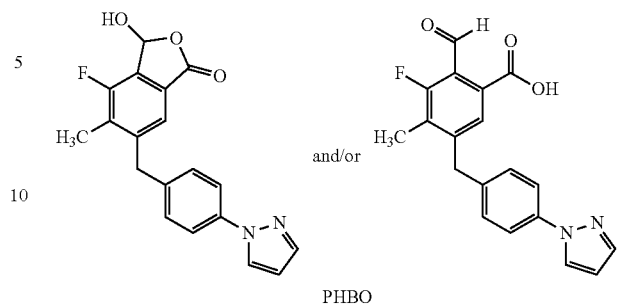

PHBO wherein the symbols are as defined above.

Step (i) and Step (ii) correspond to Steps 04 (including Step 04-1) and 05 in the below-mentioned production method, respectively.

(Production Method E)

The present invention also relates to a method of producing compound A, which comprises Step (i): a step of subjecting compound (II) to a formylation reaction to obtain compound (I), Step (ii): a step of subjecting compound (I) to a hydrolysis reaction to obtain PHBO, and Step (iii): a step of reacting PHBO with ATHP.

The scheme of the above-mentioned reaction is shown below.

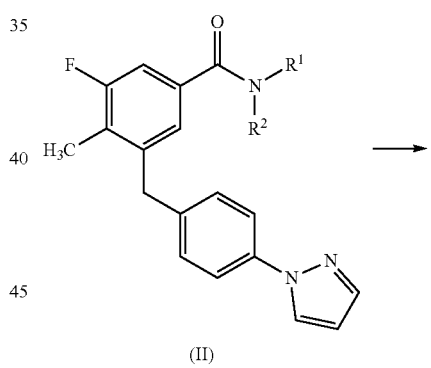

(II)

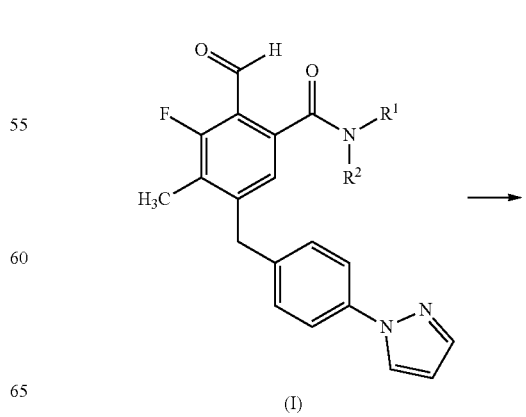

(I)

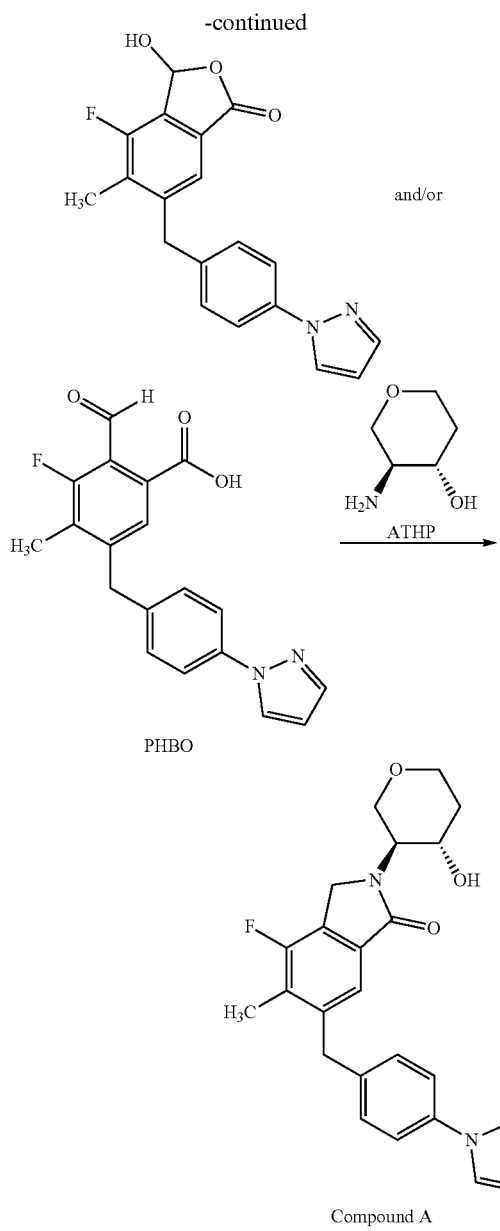

PHBO

Compound A wherein the symbols are as defined above.

Step (i), Step (ii) and Step (iii) correspond to Steps 04 (including Step 04-1), 05 and 06 in the below-mentioned production method, respectively.

4-Fluoro-3-hydroxy-5-methyl-6-[4-(1H-pyrazol-1-yl)benzyl]-2-benzofuran-1(3H)-one or a salt thereof encompassed in PHBO is a novel compound.

3-Fluoro-2-formyl-4-methyl-5-[4-(1H-pyrazol-1-yl)benzyl]benzoic acid or a salt thereof encompassed in PHBO is also a novel compound.

3-Fluoro-2-formyl-4-methyl-N,N-di(propan-2-yl)-5-[4-(1H-pyrazol-1-yl)benzyl]benzamide (compound (I) wherein $R^1$ and $R^2$ are both isopropyl) or a salt thereof is also a novel compound.

3-Fluoro-4-methyl-N,N-di(propan-2-yl)-5-[4-(1H-pyrazol-1-yl)benzyl]benzamide (compound (II) wherein $R^1$ and $R^2$ are both isopropyl) or a salt thereof is also a novel compound.

Compound A can be produced according to the production method shown in the following scheme.

In the production method shown in the following scheme, "room temperature" means generally about 10° C. to about 35° C.

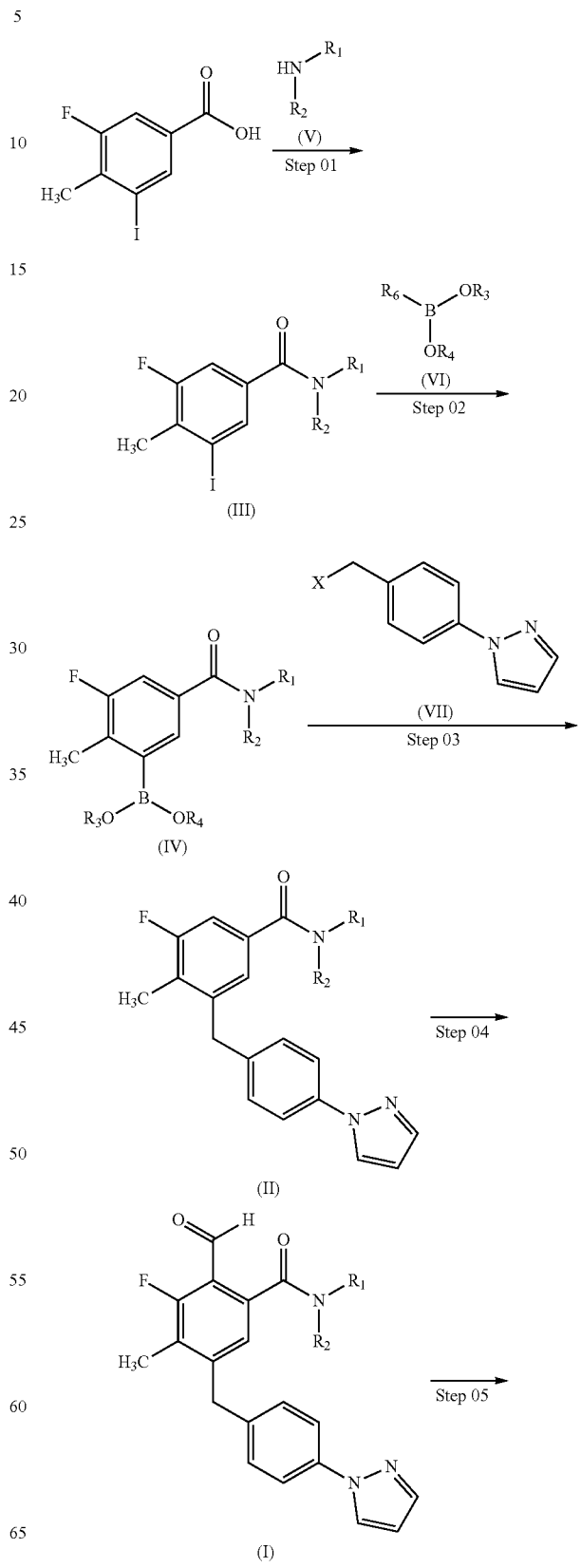

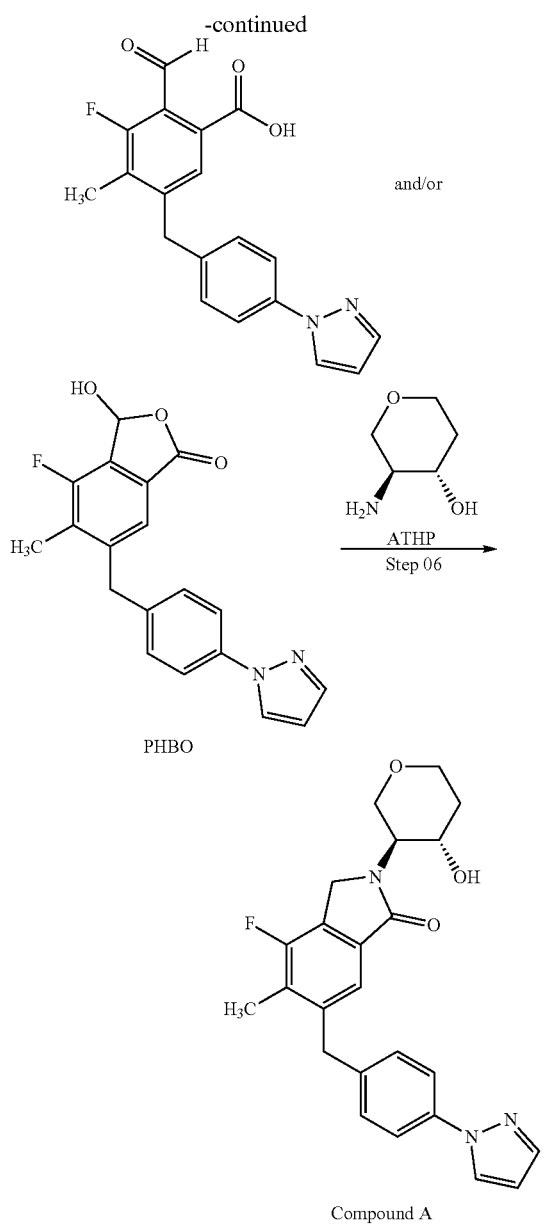

PHBO

Compound A wherein
R¹ and R² are as defined above,
R³ and R⁴ are each independently a hydrogen atom or an optionally substituted hydrocarbon group, or R³ and R⁴ form, together with the adjacent boron atom, a 3- to 8-membered monocyclic boron-containing non-aromatic heterocycle, or a 9- to 14-membered fused bicyclic boron-containing non-aromatic heterocycle,
R⁵ is (1) a hydrogen atom, (2) an optionally substituted $C_{1-6}$ alkoxy group, (3) silicon optionally substituted by 1 to 3 substituents selected from (i) a $C_{1-6}$ alkyl group and (ii) a phenyl group, (4) a boron atom optionally substituted by 1 to 3 substituents selected from a $C_{1-6}$ alkoxy group and a hydroxy group, or a 4,4,5,5-tetramethyl-[1,3,2]dioxaborolan-2-yl group, and X is a halogen atom, or an optionally substituted hydroxy group.

The optionally substituted hydrocarbon group represented by R³ or R⁴ is preferably a $C_{1-6}$ alkyl group (preferably isopropyl).

Examples of the optionally substituted $C_{1-6}$ alkoxy group represented by R⁵ include a $C_{1-6}$ alkoxy group optionally having 1 to 3 substituents selected from the above-mentioned Substituent Group A. Among them, preferred is a $C_{1-6}$ alkoxy group (preferably isopropoxy).

Examples of the above-mentioned 3- to 8-membered monocyclic boron-containing non-aromatic heterocycle include a 3- to 8-membered monocyclic non-aromatic heterocycle containing at least one boron atom (preferably one) as ring constituting atoms. The 3- to 8-membered monocyclic boron-containing non-aromatic heterocycle optionally contains a nitrogen atom, a sulfur atom and/or an oxygen atom, preferably an oxygen atom, as ring constituting atoms, in addition to a boron atom.

Examples of the above-mentioned 9- to 14-membered fused bicyclic boron-containing non-aromatic heterocycle include a 9- to 14-membered fused bicyclic non-aromatic heterocycle containing at least one boron atom (preferably one) as ring constituting atoms. The 9- to 14-membered fused bicyclic boron-containing non-aromatic heterocycle optionally contains a nitrogen atom, a sulfur atom and/or an oxygen atom, preferably an oxygen atom, as ring constituting atoms, in addition to a boron atom.

X is preferably halogen atom (preferably a chlorine atom).

The reagent and condition used in each step of the above-mentioned production method are explained in detail below.

[Step 01]

In this step, a compound represented by the formula (III) or a salt thereof (herein sometimes to be referred to as "compound (III)") is produced by reacting 3-fluoro-5-iodo-4-methylbenzoic acid or a salt thereof (herein sometimes to be referred to as "FIMA") with a compound represented by the formula (V) or a salt thereof (herein sometimes to be referred to as "compound (V)").

Step 01 includes, for example, the following Steps 01-1, 01-2, 01-3 and 01-4.

[Step 01-1]

The reaction of Step 01 can be carried out by converting FIMA to the acid chloride, and then reacting the obtained acid chloride with compound (V).

[Step 01-1-1]

The conversion to the acid chloride in Step 01-1 is carried out using a chlorinating agent. The reaction may be carried out in the presence of a catalyst, if desired.

Examples of the chlorinating agent include phosphorus oxychloride, oxalyl chloride, thionyl chloride, sulfuryl chloride, phosphorus trichloride, phosphorus pentachloride and the like.

Examples of the catalyst include N,N-dimethylformamide, pyridine, N,N-dimethyl-4-aminopyridine and the like.

While the amount of the chlorinating agent to be used varies depending on the kind of the solvent, and the other reaction condition, it is generally 0.1 to 10 mol, preferably 1 to 5 mol, per 1 mol of the substrate FIMA. The chlorinating agent may be used as a solvent.

While the amount of the catalyst to be used varies depending on the kind of the solvent, and the other reaction condition, it is generally 0.001 to 1 mol, preferably 0.01 to 0.5 mol, per 1 mol of the substrate FIMA.

The conversion to the acid chloride is carried out in the absence of a solvent, or in the presence of a solvent inert to the reaction.

The solvent inert to the reaction is not particularly limited as long as the reaction proceeds, and examples thereof include ethers such as diethyl ether, diisopropyl ether, tert-butyl methyl ether, diphenyl ether, tetrahydrofuran, 1,4- dioxane, methyltetrahydrofuran, 1,2-dimethoxyethane, 1,1-diethoxypropane, 1,1-dimethoxymethane, 2,2-dimethoxypropane, anisole and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like; amides such as N,N-dimethylformamide, N,N-dimethylacetamide, formamide, hexamethylphosphoramide, N-methylpyrrolidone, 1,3-dimethyl-2-imidazolidinone and the like; halogenated hydrocarbons such as chloroform, dichloromethane, chloroform, carbon tetrachloride, 1,2-dichloroethane and the like; nitriles such as acetonitrile, propionitrile and the like; sulfoxides such as dimethyl sulfoxide and the like; sulfones such as dimethylsulfone, sulfolane and the like; ketones such as acetone, ethyl methyl ketone, methyl isopropyl ketone, methyl butyl ketone and the like; esters such as ethyl acetate, isopropyl acetate, n-propyl acetate, n-butyl acetate, isobutyl acetate, methyl acetate, ethyl formate and the like; nitromethane and the like. These solvents may be used as a mixture at an appropriate ratio.

The conversion to the acid chloride is carried out at generally −20° C.-150° C., preferably 0° C.-100° C.

While the reaction time varies depending on the kinds of the chlorinating agent, catalyst and solvent, and the reaction temperature, it is generally 1 min-24 hr, preferably 1 min-5 hr.

[Step 01-1-2]

The reaction of the acid chloride and compound (V) in Step 01-1 can be carried out in the presence of a base.

Examples of the base include inorganic bases and organic bases.

Examples of the inorganic base include alkali metal hydroxides such as lithium hydroxide, potassium hydroxide, sodium hydroxide, cesium hydroxide and the like; alkali metal $C_{1-6}$ alkoxides such as lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide, sodium tert-butoxide, potassium tert-butoxide and the like; alkali metal thio $C_{1-6}$ alkoxides such as sodium thiomethoxide and the like; carbonates such as sodium carbonate, potassium carbonate, cesium carbonate and the like; hydrogencarbonate such as sodium hydrogencarbonate, potassium hydrogencarbonate and the like; acetates such as sodium acetate, potassium acetate and the like; phosphorates such as tripotassium phosphate, sodium phosphate and the like; and monohydrogen phosphoates such as potassium monohydrogen phosphoate, sodium monohydrogen phosphoate and the like.

Examples of the organic base include aliphatic amines such as trimethylamine, triethylamine, N-methylmorpholine, N,N-diisopropylethylamine, diethylamine, diisopropylamine, cyclohexylamine, ethylene diamine, 1,8-diazabicyclo[5.4.0]undecene and the like; aromatic amines such as pyridine, picoline, N,N-dimethylaniline and the like, and basic amino acids such as arginine, lysine, ornithine and the like.

The base to be used in this step is preferably a tertiary amine, for example, triethylamine, N-methylmorpholine, N,N-diisopropylethylamine or the like.

While the amount of compound (V) to be used varies depending on the kind of the solvent, and the other reaction condition, it is generally 0.1 to 10 mol, preferably 1 to 5 mol, per 1 mol of the substrate acid chloride.

While the amount of the base to be used varies depending on the kind of the solvent, and the other reaction condition, it is generally 0.1 to 10 mol, preferably 1 to 5 mol, per 1 mol of the substrate acid chloride. The organic base may be used as a solvent.

The reaction of the acid chloride and compound (V) is carried out in the absence of a solvent, or in the presence of a solvent inert to the reaction. The solvent inert to the reaction is not particularly limited as long as the reaction proceeds, and examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; alcohols such as methanol, ethanol, n-propanol, isopropanol, n-butanol, 2-butanol, tert-butanol, 3-methyl-1-butanol, 2-methyl-1-propanol, 1-pentanol, benzyl alcohol, 2-methoxyethanol, 2-ethoxyethanol, ethylene glycol and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like; amides such as N,N-dimethylformamide, N,N-dimethylacetamide, formamide, hexamethylphosphoramide, N-methylpyrrolidone, 1,3-dimethyl-2-imidazolidinone and the like; halogenated hydrocarbons such as chloroform, dichloromethane, chloroform, carbon tetrachloride, 1,2-dichloroethane and the like; nitriles such as acetonitrile, propionitrile and the like; sulfoxides such as dimethyl sulfoxide and the like; sulfones such as dimethylsulfone, sulfolane and the like; ketones such as acetone, ethyl methyl ketone, methyl isopropyl ketone, methyl butyl ketone and the like; esters such as ethyl acetate, isopropyl acetate, n-propyl acetate, n-butyl acetate, isobutyl acetate, methyl acetate, ethyl formate and the like; nitromethane; water and the like. These solvents may be used as a mixture at an appropriate ratio.

The reaction of the acid chloride and compound (V) is carried out at generally −20° C.-150° C., preferably 0° C.-100° C.

While the reaction time varies depending on the kinds of the base, compound (V) and solvent, and the reaction temperature, it is generally 1 min-24 hr, preferably 1 min-5 hr.

[Step 01-2]

The reaction of Step 01 can also be carried out by converting FIMA to an active acid anhydride, and then reacting the obtained active acid anhydride with compound (V).

[Step 01-2-1]

The conversion to the active acid anhydride in Step 01-2 may be carried out using an active acid anhydride-forming agent, in the presence of a base.

Examples of the base include those exemplified in the above-mentioned Step 01-1-2.

Examples of the active acid anhydride-forming agent include acid chlorides such as ethyl chloroformate, isopropyl chloroformate, pivaloyl chloride and the like; carbonyldiimidazole and the like.

While the amount of the base to be used varies depending on the kind of the solvent, and the other reaction condition, it is generally 0.1 to 10 mol, preferably 1 to 5 mol, per 1 mol of the substrate FIMA. The organic base may be used as a solvent.

While the amount of the active acid anhydride-forming agent to be used varies depending on the kind of the solvent, and the other reaction condition, it is generally 0.1 to 10 mol, preferably 1 to 5 mol, per 1 mol of the substrate FIMA.

The conversion to the active acid anhydride is carried out in the absence of a solvent, or in the presence of a solvent inert to the reaction.

Examples of the solvent inert to the reaction include those exemplified in the above-mentioned Step 01-1-2.

The conversion to the active acid anhydride is carried out at generally −20° C.-150° C., preferably 0° C.-100° C.

While the reaction time varies depending on the kinds of the base, active acid anhydride-forming agent and solvent, and the reaction temperature, it is generally 1 min-24 hr, preferably 1 min-5 hr.

[Step 01-2-2]

The reaction of the active acid anhydride and compound (V) in Step 01-2 may be carried out in the presence of a base.

Examples of the base include those exemplified in the above-mentioned Step 01-1-2.

The base to be used in this step is preferably a tertiary amine, for example, triethylamine, N-methylmorpholine, N,N-diisopropylethylamine or the like.

While the amount of the base to be used varies depending on the kind of the solvent, and the other reaction condition, it is generally 0.1 to 10 mol, preferably 1 to 5 mol, per 1 mol of the substrate active acid anhydride. The organic base may be used as a solvent.

While the amount of compound (V) to be used varies depending on the kind of the solvent, and the other reaction condition, it is generally 0.1 to 10 mol, preferably 1 to 5 mol, per 1 mol of the substrate active acid anhydride.

The reaction of the active acid anhydride and compound (V) is carried out in the absence of a solvent, or in the presence of a solvent inert to the reaction.

Examples of the solvent inert to the reaction include those exemplified in the above-mentioned Step 01-1-2.

The reaction of the active acid anhydride and compound (V) is carried out at generally −20° C.-150° C., preferably 0° C.-100° C.

While the reaction time varies depending on the kinds of the base, compound (V) and solvent, and the reaction temperature, it is generally 1 min-24 hr, preferably 1 min-5 hr.

[Step 01-3]

The reaction of Step 01 can also be carried out by reacting FIMA and compound (V) using a condensing agent.

The reaction using a condensing agent may be carried out in the presence of a base and an additive.

Examples of the condensing agent include 1-[3-(dimethylamino)propyl]-3-ethylcarbodiimide or a hydrochloride thereof, N,N'-dicyclohexylcarbodiimide, N,N'-diisopropylcarbodiimide, 4-(4,6-dimethoxy-1,3,5-triazin-2-yl)-4-methylmorpholinium=chloride n hydrate, 1H-benzotriazol-1-yloxytris(dimethylamino)phosphonium hexafluorophosphorate, 1H-benzotriazol-1-yloxytripyrrolidinophosphonium hexafluorophosphorate, (7-azabenzotriazol-1-yloxy)tripyrrolidinophosphonium hexafluorophosphorate, chlorotripyrrolidinophosphonium hexafluorophosphorate, bromotris(dimethylamino)phosphonium hexafluorophosphorate, 3-(diethoxyphosphoryloxy)-1,2,3-benzotriazin-4(3H)-one, O-(benzotriazol-1-yl)-N,N,N',N'-tetramethyluronium hexafluorophosphorate, 0-(7-azabenzotriazol-1-yl)-N,N,N',N'-tetramethyluronium hexafluorophosphorate, O—(N-succinimidyl)-N,N,N',N'-tetramethyluronium tetrafluoroborate, 0-(3,4-dihydro-4-oxo-1,2,3-benzotriazin-3-yl)-N,N,N',N'-tetramethyluronium tetrafluoroborate, S-(1-oxido-2-pyridyl)-N,N,N',N'-tetramethylthiuronium tetrafluoroborate, 0-[2-oxo-1(2H)-pyridyl]-N,N,N',N'-tetramethyluronium tetrafluoroborate, {{[(1-cyano-2-ethoxy-2-oxoethylidene)amino]oxy}-4-morpholinomethylene}dimethylammonium hexafluorophosphorate, 2-chloro-1,3-dimethylimidazoliniumhexafluorophosphorate, 1-(chloro-1-pyrrolidinylmethylene)pyrrolidinium hexafluorophosphorate, 2-fluoro-1,3-dimethylimidazoliniumhexafluorophosphorate, fluoro-N,N,N',N'-tetramethylformamidinium hexafluorophosphorate and the like. The condensing agent may be used as a mixture of two or more kinds thereof, if desired.

Examples of the base include those exemplified in the above-mentioned Step 01-1-2.

The base to be used in this step is preferably a tertiary amine, for example, triethylamine, N-methylmorpholine, N,N-diisopropylethylamine or the like.

Examples of the additive include 1-hydroxybenzotriazole, 1-hydroxy-7-azabenzotriazole, N-hydroxysuccinimide, N,N'-disuccinimidyl carbonate and the like.

While the amount of the condensing agent to be used varies depending on the kind of the solvent, and the other reaction condition, it is generally 0.1 to 10 mol, preferably 1 to 5 mol, per 1 mol of the substrate FIMA.

While the amount of the base to be used varies depending on the kind of the solvent, and the other reaction condition, it is generally 0.1 to 10 mol, preferably 1 to 5 mol, per 1 mol of the substrate FIMA. The organic base may be used as a solvent.

While the amount of the additive to be used varies depending on the kind of the solvent, and the other reaction condition, it is generally 0.1 to 10 mol, preferably 1 to 5 mol, per 1 mol of the substrate FIMA.

While the amount of compound (V) to be used varies depending on the kind of the solvent, and the other reaction condition, it is generally 0.1 to 10 mol, preferably 1 to 5 mol, per 1 mol of the substrate FIMA.

The reaction with compound (V) using a condensing agent is carried out in the absence of a solvent, or in the presence of a solvent inert to the reaction.

Examples of the solvent inert to the reaction include those exemplified in the above-mentioned Step 01-1-2.

The reaction with compound (V) using a condensing agent is carried out at generally −20° C.-150° C., preferably 0° C.-100° C.

While the reaction time varies depending on the kinds of the condensing agent, base, additive, compound (V) and solvent, and the reaction temperature, it is generally 1 min-24 hr, preferably 1 min-5 hr.

[Step 01-4]

The reaction of Step 01 can also be carried out by reacting FIMA and compound (V) using an acid.

Examples of the acid include boranes such as catecholborane, borane-trimethylamine complex, borane-tetrahydrofuran complex and the like, trialkyl borates such as trimethyl borate, isopropyl borate, tris(2,2,2-trifluoroethyl) borate and the like; borontrifluoride-ethyl ether complex, 2,4,6-tris(3,4,5-trifluorophenyl)boroxine and boric acid.

While the amount of the acid to be used varies depending on the kind of the solvent, and the other reaction condition, it is generally 0.1 to 10 mol, preferably 1 to 5 mol, per 1 mol of the substrate FIMA. The acid may be used as a solvent.

While the amount of compound (V) to be used varies depending on the kind of the solvent, and the other reaction condition, it is generally 0.1 to 10 mol, preferably 1 to 5 mol, per 1 mol of the substrate FIMA.

The reaction with compound (V) using an acid is carried out in the absence of a solvent, or in the presence of a solvent inert to the reaction.

Examples of the solvent inert to the reaction include those exemplified in the above-mentioned Step 01-1-2.

The reaction with compound (V) using an acid is carried out at generally −20° C.-150° C., preferably 0° C.-100° C.

While the reaction time varies depending on the kinds of the acid, compound (V) and solvent, and the reaction temperature, it is generally 1 min-24 hr, preferably 1 min-5 hr.

In formula (III), the compound wherein $R^1$ and $R^2$ are both isopropyl:

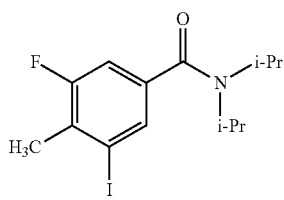 [SMILES: Cc1c(F)cc(C(=O)N(C(C)C)C(C)C)cc1I]

or a salt thereof is a novel compound.

[Step 02]

In this step, a compound represented by the formula (IV) or a salt thereof (herein sometimes to be referred to as "compound (IV)") is produced by reacting compound (III) with a boronating agent (VI).

Step 02 includes, for example, the following Steps 02-1, 02-2, 02-3 and 02-4.

[Step 02-1]

The reaction of Step 02 can be carried out by activating compound (III) with a metal, and then reacting the resulting compound with boronating agent (VI). The reaction may be carried out in the presence of an additive, if desired.

Examples of the metal include alkali metals such as lithium, sodium, potassium and the like; and alkaline-earth metals such as magnesium and the like.

Preferable examples of boronating agent (VI) include tri-$C_{1-6}$ alkyl borates such as trimethyl borate, triethyl borate, triisopropyl borate and the like; and pinacol isopropoxyborate.

Examples of the additive include iodine, 1,2-dibromoethane, diisobutylaluminium hydride, sodium bis(2-methoxyethoxy)aluminium hydride and the like.

While the amount of the metal to be used varies depending on the kind of the solvent, and the other reaction condition, it is generally 0.1 to 10 mol, preferably 1 to 5 mol, per 1 mol of the substrate compound (III).

While the amount of the boronating agent to be used varies depending on the kind of the solvent, and the other reaction condition, it is generally 0.1 to 10 mol, preferably 1 to 5 mol, per 1 mol of the substrate compound (III).

While the amount of the additive to be used varies depending on the kind of the solvent, and the other reaction condition, it is generally 0.001 to 10 mol, preferably 0.01 to 1 mol, per 1 mol of the substrate compound (III).

This reaction is advantageously carried out in the absence of a solvent, or in the presence of a solvent inert to the reaction.

The solvent inert to the reaction is not particularly limited as long as the reaction proceeds, and examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like, and the like. These solvents may be used as a mixture at an appropriate ratio.

The reaction is carried out generally at a low temperature or a high temperature, preferably −100° C.-200° C., more preferably −80° C.-150° C.

While the reaction time varies depending on the kinds of the compound (III), metal, boronating agent, additive and solvent, and the reaction temperature, it is generally 0.1 min-24 hr, preferably 1 min-5 hr.

[Step 02-2]

The reaction of Step 02 can also be carried out by reacting compound (III) with an organic metal reagent, and then reacting the resulting compound with boronating agent (VI).

Examples of the organic metal reagent include alkyl lithiums such as methyllithium, n-butyllithium, cyclohexyllithium and the like, aryl lithiums such as phenyllithium and the like, lithium amides such as lithium diisopropylamide, lithium dicyclohexylamide, lithium 2,2,6,6-tetramethylpiperidide and the like, alkyl magnesiums such as isopropylmagnesium chloride, isopropylmagnesium bromide, isopropylmagnesium chloride-lithium chloride complex and the like, and magnesium amides such as diisopropylaminomagnesium chloride, diisopropylaminomagnesium bromide, bis(isopropylamino)magnesium, 2,2,6,6-tetramethylpiperidinomagnesium chloride, 2,2,6,6-tetramethylpiperidinomagnesium bromide, 2,2,6,6-tetramethylpiperidinomagnesium chloride-lithium chloride complex and the like.

While the amount of the organic metal reagent to be used varies depending on the kind of the solvent, and the other reaction condition, it is generally 0.1 to 10 mol, preferably 1 to 5 mol, per 1 mol of the substrate compound (III).

While the amount of the boronating agent to be used varies depending on the kind of the solvent, and the other reaction condition, it is generally 0.1 to 10 mol, preferably 1 to 5 mol, per 1 mol of the substrate compound (III).

This reaction is advantageously carried out in the absence of a solvent, or in the presence of a solvent inert to the reaction.

Examples of the solvent inert to the reaction include those exemplified in the above-mentioned Step 02-1.

The reaction is carried out at generally −100° C.-200° C., preferably −80° C.-150° C.

While the reaction time varies depending on the kinds of the compound (III), organic metal reagent, boronating agent and solvent, and the reaction temperature, it is generally 1 min-24 hr, preferably 1 min-5 hr.

[Step 02-3]

The reaction of Step 02 can also be carried out by reacting compound (III) with boronating agent (VI) using a metal catalyst in the presence of a base. The reaction may be carried out by addition of an additive, if desired.

Examples of the base include those exemplified in the above-mentioned Step 01-1-2.

Examples of the metal catalyst include palladium catalysts such as tetrakis(triphenylphosphine)palladium, [1,1'-bis(diphenylphosphino)ferrocene]palladium(II) dichloride, tris(dibenzylideneacetone)dipalladium and the like; nickel catalysts such as nickel bromide, bis(triphenylphosphine)nickel(II) dichloride, [1,3-bis(diphenylphosphino)propane]nickel(II) dichloride, bis(1,5-cyclooctadiene)nickel(0) and the like; copper catalysts such as copper chloride, copper iodide, copper oxide, copper acetate and the like; and iron catalysts such as iron bromide, [1,2-bis(diphenylphosphino)ethane]dichloroiron(II), [1,2-bis(dicyclohexylphosphino)ethane]dichloroiron(II) and the like.

Examples of the additive include 2,2'-bis(diphenylphosphino)-1,1'-binaphthyl (hereinafter sometimes to be referred to as BINAP); BINAP derivatives having substituent(s) such as a $C_{1-6}$ alkyl group, a $C_{6-14}$ aryl group and the like on the naphthyl ring of BINAP, for example, 2,2'-bis(diphenylphosphino)-6,6'-dimethyl-1,1'-binaphthyl; BINAP derivatives wherein the naphthyl ring of BINAP is partially hydrogenated, for example, 2,2'-bis(diphenylphosphino)-5,6,7,8,5',6',7',8'-octahydro-1,1'-binaphthyl (H8BINAP); BINAP derivatives having 1 to 5 substituents such as a $C_{1-6}$ alkyl group, a halogen atom, a mono- or di-$C_{1-6}$ alkylamino group, a $C_{1-6}$ alkoxy group, a pyrrolidinyl group and the like on the benzene ring on the phosphorus atom of BINAP, for example, 2,2'-bis[bis(4-chlorophenyl)phosphino)-1,1'-binaphthyl, 2,2'-bis(di-p-tolylphosphino)-1,1'-binaphthyl (tol-BINAP), 2,2'-bis[bis(3,5-dimethylphenyl)phosphino]-1,1'-binaphthyl (xyl-BINAP), 2,2'-bis[bis(3,5-diethylphenyl)phosphino]-1,1'-binaphthyl, 2,2'-bis[bis(3,5-diisopropylphenyl)phosphino]-1,1'-binaphthyl, 2,2'-bis[bis(3,5-di-tert-butylphenyl)phosphino]-1,1'-binaphthyl, 2,2'-bis[bis(4-dimethylaminophenyl)phosphino]-1,1'-binaphthyl, 2,2'-bis[bis(4-dimethylamino-3,5-dimethylphenyl)phosphino]-1,1'-binaphthyl, 2,2'-bis[bis(4-dimethylamino-3,5-diethylphenyl)phosphino]-1,1'-binaphthyl, 2,2'-bis[bis(4-dimethylamino-3,5-diisopropylphenyl)phosphino]-1,1'-binaphthyl, 2,2'-bis[bis(4-diethylaminophenyl)phosphino]-1,1'-binaphthyl, 2,2'-bis[bis[4-(pyrrolidin-1-yl)phenyl]phosphino]-1,1'-binaphthyl, 2,2'-bis(di-p-methoxyphenylphosphino)-1,1'-binaphthyl, 2,2'-bis[bis(3,5-dimethyl-4-methoxyphenyl)phosphino]-1,1'-binaphthyl, 2,2'-bis[bis(3,5-di-tert-butyl-4-methoxyphenyl)phosphino]-1,1'-binaphthyl (DTBM-BINAP); 2,2'-bis(dicyclohexylphosphino)-6,6'-dimethyl-1,1'-biphenyl (BICHEP), 2,2'-bis(diphenylphosphino)-6,6'-dimethoxybiphenyl (MeO-BIPHEP), 2,3-bis(diphenylphosphino)butane (CHIRAPHOS), 1-cyclohexyl-1,2-bis(diphenylphosphino)ethane (CYCPHOS), 1,2-bis[(2-methoxyphenyl)phenylphosphino]ethane (DIPAMP), 1,2-bis(diphenylphosphino)propane (PROPHOS), 2,4-bis(diphenylphosphino)pentane (SKEWPHOS), SKEWPHOS derivatives having 1 to 5 substituents such as a $C_{1-6}$ alkyl group and the like on the benzene ring on the phosphorus atom of SKEWPHOS, 1-[1',2-bis(diphenylphosphino)ferrocenyl]ethylene diamine (BPPFA), 1-substituted-3,4-bis(diphenylphosphino)pyrrolidine (DEGPHOS), 2,3-O-isopropylidene-2,3-dihydroxy-1,4-bis(diphenylphosphino)butane(DIOP), substituted-1,2-bisphospholanobenzene (DuPHOS), substituted-1,2-bisphospholanoethane (BPE), 5,6-bis(diphenylphosphino)-2-norbornene (NORPHOS), N,N'-bis(diphenylphosphino)-N,N'-bis(1-phenylethyl)ethylene diamine (PNNP), 2,2'-diphenylphosphino-1,1'-bicyclopentyl (BICP), 4,12-bis(diphenylphosphino)-[2,2]-paracyclophane (PhanePHOS), N-substituted-N-diphenylphosphino-1-[2-(diphenylphosphino)ferrocenyl]ethylamine (BoPhoz), 1-[2-(disubstituted-phosphino)ferrocenyl]ethyl-disubstituted-phosphine (Josiphos), 1-[2-(2'-disubstituted-phosphinophenyl)ferrocenyl]ethyl-disubstituted-phosphine (Walphos), 2,2'-bis(a-N,N-dimethylaminophenylmethyl)-1,1'-bis(disubstituted-phosphino)ferrocene (Mandyphos), disubstituted-phosphino-2-[a-(N,N-dimethylamino)-o-disubstituted-phosphinophenyl-methyl]ferrocene (Taniaphos), 1,1-bis(disubstituted-phosphotano)ferrocene (FerroTANE), 7,7'-bis(diphenylphospino)-3,3',4,4'-tetrahydro-4,4'-dimethyl-8,8'-bi(2H-1,4-benzoxazine) (Solphos) and the like.

Preferable examples of boronating agent (VI) include diborons such as bis(pinacolato)diboron, tetrahydroxydiboron, bis(neo-pentylglycolato)diboron, bis(hexylene glycolato)diboron, bis(catecholato)diboron and the like, tri-$C_{1-6}$ alkyl borates such as trimethyl borate, triethyl borate, triisopropyl borate and the like; silylborons such as 2-(dimethylphenylsilyl)-4,4,5,5-tetramethyl-1,3,2-dioxaborolane and the like; and boranes such as pinacolborane and the like.

While the amount of the base to be used varies depending on the kind of the solvent, and the other reaction condition, it is generally 0.1 to 10 mol, preferably 1 to 5 mol, per 1 mol of the substrate compound (III).

While the amount of the metal catalyst to be used varies depending on the kind of the solvent, and the other reaction condition, it is generally 0.0001 to 1 mol, preferably 0.01 to 0.1 mol, per 1 mol of the substrate compound (III).

While the amount of the additive to be used varies depending on the kind of the solvent, and the other reaction condition, it is generally 0.0001 to 1 mol, preferably 0.01 to 0.1 mol, per 1 mol of the substrate compound (III).

While the amount of boronating agent (VI) to be used varies depending on the kind of the solvent, and the other reaction condition, it is generally 0.1 to 10 mol, preferably 1 to 5 mol, per 1 mol of the substrate compound (III).

This reaction is advantageously carried out in the absence of a solvent, or in the presence of a solvent inert to the reaction.

Examples of the solvent inert to the reaction include those exemplified in the above-mentioned Step 01-1-2.

The reaction is carried out at generally −100° C.-200° C., preferably −80° C.-150° C.

While the reaction time varies depending on the kinds of the compound (III), base, metal catalyst, additive, boronating agent and solvent, and the reaction temperature, it is generally 1 min-24 hr, preferably 1 min-10 hr.

[Step 02-4]

The reaction of Step 02 can also be carried out by reacting compound (III) with boronating agent (VI) under light irradiation. The method by light irradiation can be carried out according to the method described in Journal of the American Chemical Society 2016, 138, 2985-2988, or Organic Letters 2016, 18, 5248-5251, or a method analogous thereto.

In formula (IV), the compound wherein $R^1$ and $R^2$ are both isopropyl, and $R^3$ and $R^4$ are both hydrogen atoms:

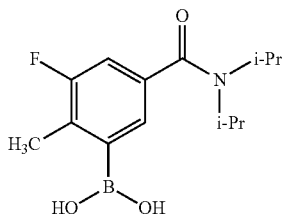

or a salt thereof is a novel compound.

[Step 03]

In this step, compound (II) is produced by reacting compound (IV) with a compound represented by the formula (VII) or a salt thereof (herein sometimes to be referred to as "compound (VII)").

The reaction of compound (IV) with compound (VII) may be carried out in the presence of a metal catalyst and a base, if desired. The reaction may be carried out by addition of an additive, if desired. When the metal catalyst is not used, the reaction can be carried out according to the method described in Tetrahedron Letters 2016, 57, 4142-4144, or a method analogous thereto.

Examples of the metal catalyst include palladium catalysts such as palladium chloride, palladium acetate, tetrakis(triphenylphosphine)palladium, dichlorobis(triphenylphosphine)palladium, [1,1'-bis(diphenylphosphino)ferrocene]palladium(II) dichloride, tris(dibenzylideneacetone)dipalladium and the like, copper catalysts such as copper chloride, copper iodide and the like, iron catalysts such as tris(2,4-pentanedionato)iron, 1,2-phenylene bis[diphenyl]phosphine iron complex and the like, and the like.

Examples of the base include those exemplified in the above-mentioned Step 01-1-2.

Examples of the additive include those exemplified in the above-mentioned Step 02-3.

While the amount of the metal catalyst to be used varies depending on the kind of the solvent, and the other reaction condition, it is generally 0.0001 to 1 mol, preferably 0.01 to 0.1 mol, per 1 mol of the substrate compound (IV).

While the amount of the base to be used varies depending on the kind of the solvent, and the other reaction condition, it is generally 0.1 to 10 mol, preferably 1 to 5 mol, per 1 mol of the substrate compound (IV).

While the amount of the additive to be used varies depending on the kind of the solvent, and the other reaction condition, it is generally 0.0001 to 1 mol, preferably 0.01 to 0.1 mol, per 1 mol of the substrate compound (IV).

While the amount of compound (VII) to be used varies depending on the kind of the solvent, and the other reaction condition, it is generally 0.1 to 10 mol, preferably 1 to 5 mol, per 1 mol of the substrate compound (IV).

This reaction is advantageously carried out in the absence of a solvent, or in the presence of a solvent inert to the reaction.

Examples of the solvent inert to the reaction include those exemplified in the above-mentioned Step 01-1-2.

The reaction is carried out at generally −20° C.-150° C., preferably 0° C.-100° C.

While the reaction time varies depending on the kinds of the compound (IV), compound (VII), metal catalyst, base, additive and solvent, and the reaction temperature, it is generally 1 min-24 hr, preferably 1 min-5 hr.

[Step 04]

In this step, compound (I) is produced by subjecting compound (II) to a formylation reaction.

The reaction is generally carried out using a formylating agent.

The reaction is preferably carried out in the presence of an organic metal reagent.

Examples of the organic metal reagent include those exemplified in the above-mentioned Step 02-2.

Preferable examples of the organic metal reagent include n-butyllithium, lithium diisopropylamide, lithium dicyclohexylamide, lithium 2,2,6,6-tetramethylpiperidide, diisopropylaminomagnesium chloride, diisopropylaminomagnesium bromide, 2,2,6,6-tetramethylpiperidinomagnesium chloride, and 2,2,6,6-tetramethylpiperidinomagnesium chloride-lithium chloride complex. Among them, preferred are n-butyllithium, lithium diisopropylamide, 2,2,6,6-tetramethylpiperidinomagnesium chloride, and 2,2,6,6-tetramethylpiperidinomagnesium chloride-lithium chloride complex. More preferred are n-butyllithium, lithium diisopropylamide, and 2,2,6,6-tetramethylpiperidinomagnesium chloride-lithium chloride complex.

Use of 2,2,6,6-tetramethylpiperidinomagnesium chloride-lithium chloride complex as an organic metal reagent enables high-yield production of compound (I) with high purity.

Examples of the formylating agent include N,N-disubstituted formylamides such as dimethylformamide, N-formylmorpholine, N-formylpiperidine and the like; formate esters such as methyl formate, ethyl formate and the like; orthoformate esters such as orthomethyl formate, orthoethyl formate and the like; and N-ethoxymethyleneaniline and the like. Among them, preferred is dimethylformamide.

While the amount of the organic metal reagent to be used varies depending on the kind of the solvent, and the other reaction condition, it is generally 0.1 to 100 mol, preferably 1 to 10 mol, per 1 mol of the substrate compound (II).

While the amount of the formylating agent to be used varies depending on the kind of the solvent, and the other reaction condition, it is generally 0.1 to 40 mol, preferably 1 to 10 mol, per 1 mol of the substrate compound (II).

The organic metal reagent and formylating agent may be each added in one batch or in several batches. Alternatively, the formylating agent may be added in the presence of the organic metal reagent, or the organic metal reagent may be added in the presence of the formylating agent.

For example, when n-butyllithium is added in the presence of dimethylformamide, addition of diisopropylamine to dimethylformamide enables high-yield production of compound (I) with high purity.

This reaction is advantageously carried out in the absence of a solvent, or in the presence of a solvent inert to the reaction.

The solvent inert to the reaction is not particularly limited as long as the reaction proceeds, and examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like, and the like. These solvents may be used as a mixture at an appropriate ratio. The solvent is preferably tetrahydrofuran.

The reaction is carried out at generally −100° C.-150° C., preferably −20° C.-50° C.

While the reaction time varies depending on the kinds of the compound (II), organic metal reagent, formylating agent and solvent, and the reaction temperature, it is generally 1 min-24 hr, preferably 1 min-5 hr.

[Step 04-1]

Flow chemistry technique can be applied to Step 04.

As flow chemistry techniques, methods commonly used in a chemical synthesis field are employed.

Specifically, compound (II) is dissolved in the above-mentioned solvent inert to the reaction, the obtained solution is supplied to a tube reactor, and an organic metal reagent and formylating agent are added successively to the solution flowing through the reactor, and thereby, the formylation reaction of compound (II), which is explained in detail in Step 04, can be carried out in an extremely short time.

When flow chemistry technique is employed, preferable examples of the organic metal reagent include n-butyllithium, lithium diisopropylamide, lithium dicyclohexylamide, lithium 2,2,6,6-tetramethylpiperidide, diisopropylaminomagnesium chloride, diisopropylaminomagnesium bromide, 2,2,6,6-tetramethylpiperidinomagnesium chloride, and 2,2,6,6-tetramethylpiperidinomagnesium chloride-lithium chloride complex. Among them, preferred is n-butyllithium.

When flow chemistry technique is employed, while the amount of the organic metal reagent to be used varies depending on the kind of the solvent, and the other reaction condition, it is generally 0.1 to 20 mol, preferably 1.0 to 3.0 mol, per 1 mol of the substrate compound (II).

When flow chemistry technique is employed, while the amount of the formylating agent to be used varies depending on the kind of the solvent, and the other reaction condition, it is generally 0.1 to 40 mol, preferably 1 to 33 mol, per 1 mol of the substrate compound (II).

When flow chemistry technique is employed, the reaction is carried out at generally −100° C.-30° C., preferably −60° C.-0° C.

When flow chemistry technique is employed, while the reaction time varies depending on the kinds of the compound (II), organic metal reagent, formylating agent and solvent, and the reaction temperature, it is generally 0.01 sec-1 min, preferably 0.01 sec-1 sec.

[Step 05]

In this step, PHBO is produced by subjecting compound (I) to a hydrolysis reaction.

The reaction may be carried out in the presence of an acid or base, if desired. The reaction may be carried out by addition of an additive, if desired.

Examples of the acid include mineral acids such as hydrofluoric acid, hydrochloric acid, hydrobromic acid, hydroiodic acid, nitric acid, sulfuric acid, sulfurous acid and the like; phosphoric acid, phosphorus acid, carbonic acid, bicarbonic acid; carboxylic acids such as formic acid, acetic acid, trifluoroacetic acid, phthalic acid, fumaric acid, oxalic acid, tartaric acid, maleic acid, citric acid, succinic acid, malic acid and the like; acidic amino acids such as aspartic acid, glutamic acid and the like; and sulfonic acids such as methanesulfonic acid, trifluoromethanesulfonic acid, benzenesulfonic acid, p-toluenesulfonic acid, camphorsulfonic acid and the like. The acid may be used as a mixture of two or more kinds thereof, if desired.

Examples of the base include those exemplified in the above-mentioned Step 01-1-2.

Examples of the additive include sodium salts such as sodium chloride, sodium bromide, sodium iodide and the like, and potassium salts such as potassium chloride, potassium bromide, potassium iodide and the like. Among them, preferred is sodium bromide.

While the amount of the acid to be used varies depending on the kind of the solvent, and the other reaction condition, it is generally 0.1 to 10000 mol, preferably 1 to 10 mol, per 1 mol of the substrate compound (I). The acid may be used as a solvent.

While the amount of the base to be used varies depending on the kind of the solvent, and the other reaction condition, it is generally 0.1 to 10000 mol, preferably 1 to 10 mol, per 1 mol of the substrate compound (I). The organic base may be used as a solvent.

While the amount of the additive to be used varies depending on the kind of the solvent, and the other reaction condition, it is generally 0.1 to 10 mol, preferably 1 to 5 mol, per 1 mol of the substrate compound (I).

This reaction is preferably carried out in the presence of an acid. The acid is preferably hydrobromic acid, sulfuric acid or p-toluenesulfonic acid.

For example, combination use of hydrobromic acid and p-toluenesulfonic acid as an acid enables suppression of impurity generation.

For example, the reaction in the presence of sulfuric acid and sodium bromide enables suppression of impurity generation, and thereby, PHBO with high purity can be produced.

This reaction is advantageously carried out in the absence of a solvent, or in the presence of a solvent inert to the reaction.

Examples of the solvent inert to the reaction include those exemplified in the above-mentioned Step 01-1-2.

The reaction is carried out at generally −20° C.-200° C., preferably 0° C.-150° C.

While the reaction time varies depending on the kinds of the compound (I), acid, base, additive, solvent, and the reaction temperature, it is generally 1 min-24 hr, preferably 1 min-12 hr.

[Step 06]

In this step, compound A is produced by reacting PHBO with ATHP.

The reaction is preferably carried out in the presence of a reducing agent.

Examples of the reducing agent include metal borohydrides such as sodium borohydride, lithium borohydride, calcium borohydride, sodium cyanoborohydride, sodium triacetoxyborohydride and the like, boranes such as borane-pyridine complex, 2-picoline-borane complex, 5-ethyl-2-methylpyridine-borane complex and the like, and the like. The reducing agent may be used as a mixture of two or more kinds thereof, if desired. Alternatively, as a reducing agent, hydrogen can be used together with a metal catalyst such as palladium carbon, platinum carbon, Raney nickel and the like. The reducing agent is preferably sodium triacetoxyborohydride.

While the amount of the reducing agent to be used varies depending on the kind of the solvent, and the other reaction condition, it is generally 0.1 to 10 mol, preferably 1 to 5 mol, per 1 mol of the substrate PHBO.

While the amount of ATHP to be used varies depending on the kind of the solvent, and the other reaction condition, it is generally 0.1 to 10 mol, preferably 1 to 5 mol, per 1 mol of the substrate PHBO.

This reaction is advantageously carried out in the absence of a solvent, or in the presence of a solvent inert to the reaction.

The solvent inert to the reaction is not particularly limited as long as the reaction proceeds, and examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; alcohols such as methanol, ethanol, n-propanol, isopropanol, n-butanol, 2-butanol, tert-butanol, 3-methyl-1-butanol, 2-methyl-1-propanol, 1-pentanol, benzyl alcohol, 2-methoxyethanol, 2-ethoxyethanol, ethylene glycol and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like; amides such as N,N-dimethylformamide, N,N-dimethylacetamide, formamide, hexamethylphosphoramide, N-methylpyrrolidone, 1,3-dimethyl-2-imidazolidinone and the like; halogenated hydrocarbons such as chloroform, dichloromethane, chloroform, carbon tetrachloride, 1,2-dichloroethane and the like; nitriles such as acetonitrile, propionitrile and the like; sulfoxides such as dimethyl sulfoxide and the like; sulfones such as dimethylsulfone, sulfolane and the like; ketones such as acetone, ethyl methyl ketone, methyl isopropyl ketone, methyl butyl ketone and the like; esters such as ethyl acetate, isopropyl acetate, n-propyl acetate, n-butyl acetate, isobutyl acetate, methyl acetate, ethyl formate and the like; nitromethane; water; acetic acid and the like. These solvents may be used as a mixture at an appropriate ratio. The solvent is preferably a mixture of tetrahydrofuran and acetic acid at an any ratio.

The reaction is carried out at generally −20° C.-150° C., preferably 0° C.-100° C.

While the reaction time varies depending on the kinds of the reducing agent and solvent, and the reaction temperature, it is generally 1 min-24 hr, preferably 1 min-3 hr.

In this reaction, when 3-fluoro-2-formyl-4-methyl-5-[4-(1H-pyrazol-1-yl)benzyl]benzoic acid 1,4-diazabicyclo[2.2.2]octane salt is used as PHBO, washing of the reaction crude product under a basic condition enables production of compound A with high purity. Washing under a basic condition is preferably carried out using aqueous ammonia.

(Production Method F)

The present invention also relates to a method of producing PHBO, which comprises subjecting compound (VIII) to a formylation reaction, and then a hydrolysis reaction, if desired.

The scheme of the above-mentioned reaction is shown below (hereinafter to be referred to as Step (iv-1)).

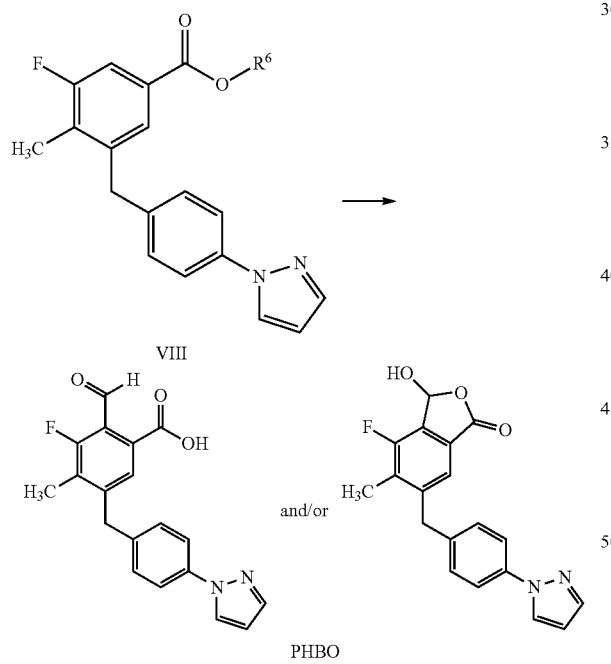

wherein $R^6$ is a hydrogen atom or an optionally substituted $C_{1-6}$ alkyl group.

Step (iv-1) corresponds to Step 10 in the below-mentioned production method.

(Production Method G)

The present invention also relates to a method of producing compound (VIII), which comprises subjecting compound (IX) to a reduction reaction.

The scheme of the above-mentioned reaction is shown below (hereinafter to be referred to as Step (iii-1)).

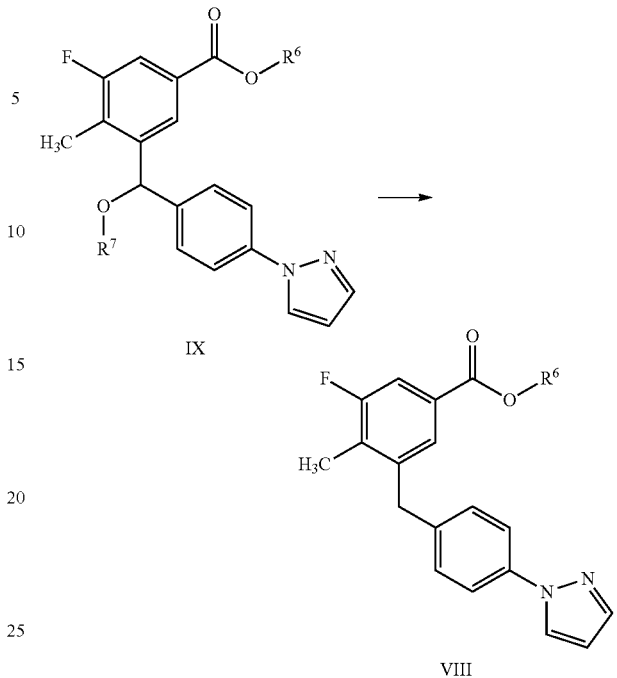

wherein $R^6$ is as defined above, and $R^7$ is a protecting group.

Step (iii-1) corresponds to Step 09 (including Step 09-1) in the below-mentioned production method.

(Production Method H)

The present invention also relates to a method of producing compound (IX), which comprises subjecting compound (X) to a protection reaction of the hydroxy group.

The scheme of the above-mentioned reaction is shown below (hereinafter to be referred to as Step (ii-1)).

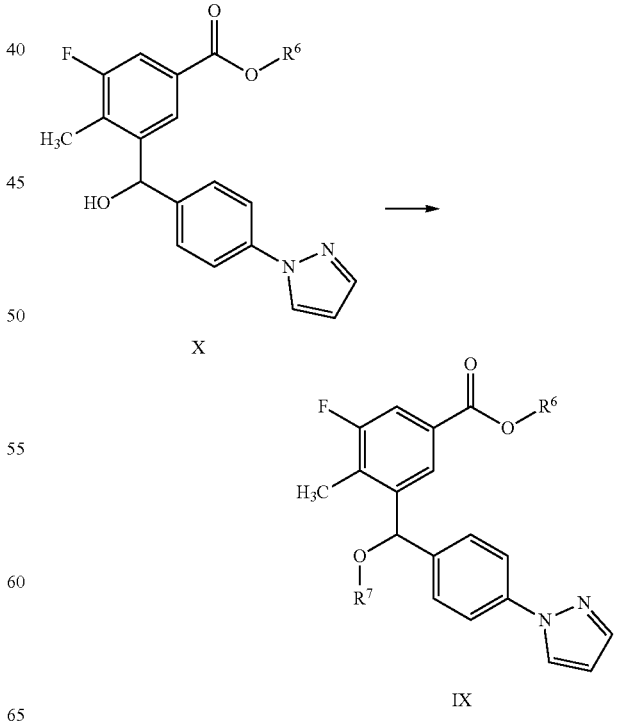

wherein the symbols are as defined above.

Step (ii-1) corresponds to Step 08 (including Step 08-1, Step 08-2, Step 08-3, Step 08-4, Step 08-5 and Step 08-6) in the below-mentioned production method.
(Production Method I)

The present invention also relates to a method of producing compound (X), which comprises reacting compound (XI) with 4-(1H-pyrazol-1-yl)benzaldehyde.

The scheme of the above-mentioned reaction is shown below (hereinafter to be referred to as Step (i-1)).

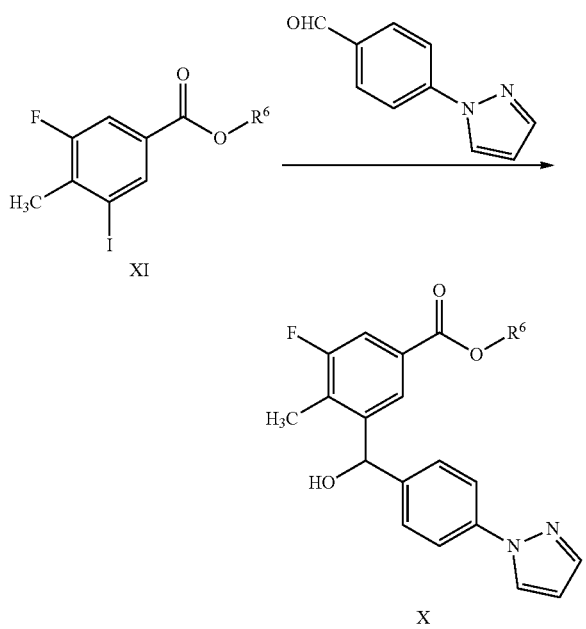

wherein the symbol is as defined above.

Step (i-1) corresponds to Step 07 (including Step 07-1 and Step 07-2) in the below-mentioned production method.
(Production Method J)

The present invention also relates to a method of producing compound (IX), which comprises Step (i-1): a step of reacting compound (XI) with 4-(1H-pyrazol-1-yl)benzaldehyde to obtain compound (X), and Step (ii-1): a step of subjecting compound (X) to a protection reaction of the hydroxy group.

Step (i-1) and Step (ii-1) correspond to Step 07 (including Step 07-1 and Step 07-2) and Step 08 (including Step 08-1, Step 08-2, Step 08-3, Step 08-4, Step 08-5 and Step 08-6) in the below-mentioned production method, respectively.
(Production Method K)

The present invention also relates to a method of producing compound (VIII), which comprises Step (i-1): a step of reacting compound (XI) with 4-(1H-pyrazol-1-yl)benzaldehyde to obtain compound (X), Step (ii-1): a step of subjecting compound (X) to a protection reaction of the hydroxy group to obtain compound (IX), and Step (iii-1): a step of subjecting compound (IX) to a reduction reaction.

Step (i-1), Step (ii-1) and Step (iii-1) correspond to Step 07 (including Step 07-1 and Step 07-2), Step 08 (including Step 08-1, Step 08-2, Step 08-3, Step 08-4, Step 08-5 and Step 08-6) and Step 09 (including Step 09-1) in the below-mentioned production method, respectively.
(Production Method L)

The present invention also relates to a method of producing PHBO, which comprises Step (i-1): a step of reacting compound (XI) with 4-(1H-pyrazol-1-yl)benzaldehyde to obtain compound (X), Step (ii-1): a step of subjecting compound (X) to a protection reaction of the hydroxy group to obtain compound (IX), Step (iii-1): a step of subjecting compound (IX) to a reduction reaction to obtain compound (VIII), and Step (iv-1): a step of subjecting compound (VIII) to a formylation reaction, and then a hydrolysis reaction, if desired.

Step (i-1), Step (ii-1), Step (iii-1) and Step (iv-1) correspond to Step 07 (including Step 07-1 and Step 07-2), Step 08 (including Step 08-1, Step 08-2, Step 08-3, Step 08-4, Step 08-5 and Step 08-6), Step 09 (including Step 09-1) and Step 10 in the below-mentioned production method, respectively.
(Production Method M)

The present invention also relates to a method of producing compound A, which comprises Step (i-1): a step of reacting compound (XI) with 4-(1H-pyrazol-1-yl)benzaldehyde to obtain compound (X), Step (ii-1): a step of subjecting compound (X) to a protection reaction of the hydroxy group to obtain compound (IX), Step (iii-1): a step of subjecting compound (IX) to a reduction reaction to obtain compound (VIII), Step (iv-1): a step of subjecting compound (VIII) to a formylation reaction, and then a hydrolysis reaction, if desired, to obtain PHBO, and Step (v-1): reacting a step of PHBO with ATHP.

Step (i-1), Step (ii-1), Step (iii-1) and Step (iv-1) correspond to Step 07 (including Step 07-1 and Step 07-2), Step 08 (including Step 08-1, Step 08-2, Step 08-3, Step 08-4, Step 08-5 and Step 08-6), Step 09 (including Step 09-1) and Step 10 in the below-mentioned production method, respectively.

Step (v-1) corresponds to Step 06 in the below-mentioned production method.

Compound A can be produced according to the production method shown in the following scheme.

In the production method shown in the following scheme, "room temperature" means generally about 10° C. to about 35° C.

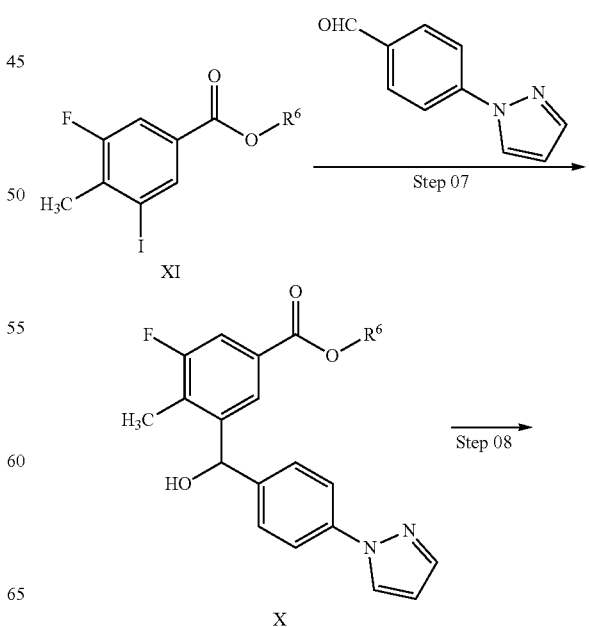

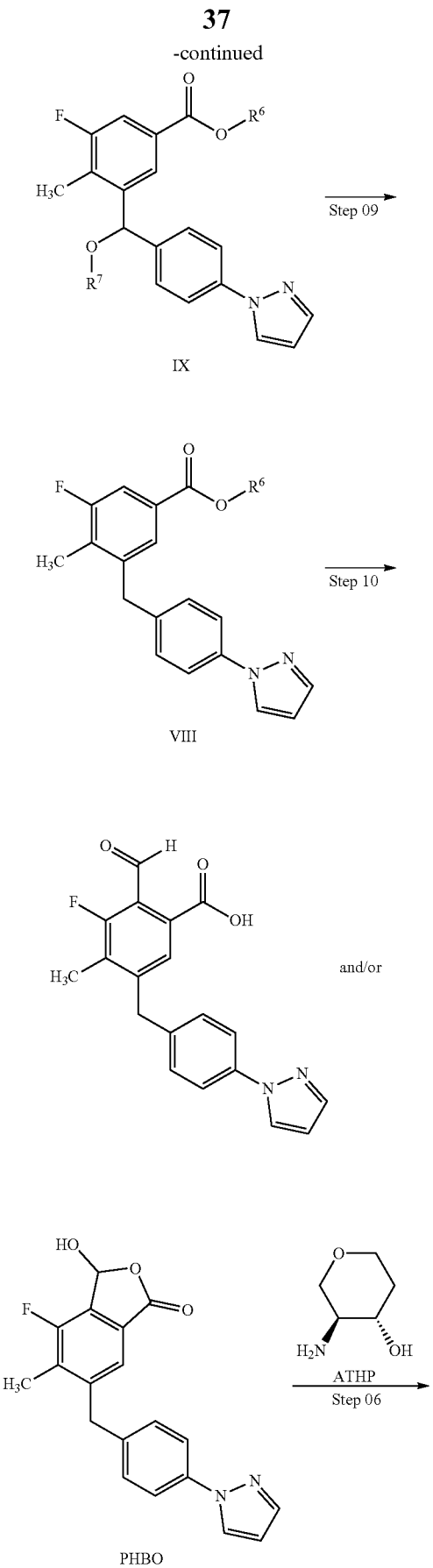

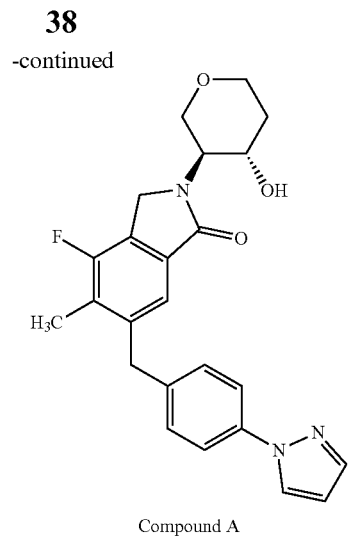

Compound A wherein
R⁶ is a hydrogen atom or an optionally substituted $C_{1-6}$ alkyl group, and
R⁷ is a protecting group.

The reagent and condition used in each step of the above-mentioned production method are explained in detail below.

[Step 07]

In this step, compound (X) is produced by reacting compound (XI) with 4-(1H-pyrazol-1-yl)benzaldehyde.

Step 07 includes, for example, the following Step 07-1 and Step 07-2.

[Step 07-1]

The reaction of Step 07 can be carried out by activating compound (XI) with a metal, and then reacting the resulting compound with 4-(1H-pyrazol-1-yl)benzaldehyde. The reaction may be carried out in the presence of an additive, if desired.

Examples of the metal include alkali metals such as lithium, sodium, potassium and the like; and alkaline-earth metals such as magnesium and the like.

Examples of the additive include iodine, 1,2-dibromoethane, diisobutylaluminium hydride, sodium bis(2-methoxyethoxy)aluminium hydride and the like.

While the amount of the metal to be used varies depending on the kind of the solvent, and the other reaction condition, it is generally 0.1 to 10 mol, preferably 1 to 5 mol, per 1 mol of compound (XI).

While the amount of 4-(1H-pyrazol-1-yl)benzaldehyde to be used varies depending on the kind of the solvent, and the other reaction condition, it is generally 0.1 to 10 mol, preferably 0.9 to 5 mol, per 1 mol of compound (XI).

While the amount of the additive to be used varies depending on the kind of the solvent, and the other reaction condition, it is generally 0.001 to 10 mol, preferably 0.01 to 1 mol, per 1 mol of compound (XI).

This reaction is advantageously carried out in the absence of a solvent, or in the presence of a solvent inert to the reaction.

The solvent inert to the reaction is not particularly limited as long as the reaction proceeds, and examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like, and the like. These solvents may be used as a mixture at an appropriate ratio.

The reaction is carried out generally at a low temperature or a high temperature, preferably −100° C.-200° C., more preferably −80° C.-150° C.

While the reaction time varies depending on the kinds of the compound (XI), metal, additive and solvent, and the reaction temperature, it is generally 1 min-24 hr, preferably 1 min-5 hr.

[Step 07-2]

The reaction of Step 07 can also be carried out by reacting compound (XI) with an organic metal reagent, and then reacting the resulting compound with 4-(1H-pyrazol-1-yl) benzaldehyde.

Examples of the organic metal reagent include alkyl lithiums such as methyllithium, n-butyllithium, cyclohexyllithium and the like, aryl lithiums such as phenyllithium and the like, lithium amides such as lithium diisopropylamide, lithium dicyclohexylamide, lithium 2,2,6,6-tetramethylpiperidide and the like, alkyl magnesiums such as isopropylmagnesium chloride, isopropylmagnesium bromide, isopropylmagnesium chloride-lithium chloride complex and the like, and magnesium amides such as diisopropylaminomagnesium chloride, diisopropylaminomagnesium bromide, bis(isopropylamino)magnesium, 2,2,6,6-tetramethylpiperidinomagnesium chloride, 2,2,6,6-tetramethylpiperidinomagnesium bromide, 2,2,6,6-tetramethylpiperidinomagnesium chloride-lithium chloride complex and the like. Among them, preferred are isopropylmagnesium bromide, and isopropylmagnesium chloride-lithium chloride complex.

While the amount of the organic metal reagent to be used varies depending on the kind of the solvent, and the other reaction condition, it is generally 0.1 to 10 mol, preferably 1 to 5 mol, per 1 mol of compound (XI).

While the amount of 4-(1H-pyrazol-1-yl)benzaldehyde to be used varies depending on the kind of the solvent, and the other reaction condition, it is generally 0.1 to 10 mol, preferably 0.9 to 5 mol, per 1 mol of compound (XI).

This reaction is advantageously carried out in the absence of a solvent, or in the presence of a solvent inert to the reaction.

Examples of the solvent inert to the reaction include those exemplified in the above-mentioned Step 07-1. Among them, preferred is tetrahydrofuran.

The reaction is carried out at generally −100° C.-200° C., preferably −80° C.-150° C.

While the reaction time varies depending on the kinds of the compound (XI), organic metal reagent and solvent, and the reaction temperature, it is generally 1 min-24 hr, preferably 1 min-5 hr.

[Step 08]

In this step, compound (IX) is produced, for example, by subjecting compound (X) to a protection reaction of the hydroxy group.

Step 08 includes, for example, the following Step 08-1, Step 08-2, Step 08-3, Step 08-4, Step 08-5 and Step 08-6.

[Step 08-1]

The reaction of Step 08 can be carried out, for example, by reacting compound (X) with an anhydride in the presence of a base. The reaction may be carried out in the presence of a catalyst, if desired.

Examples of the base include inorganic bases and organic bases.

Examples of the inorganic base include alkali metal hydroxides such as lithium hydroxide, potassium hydroxide, sodium hydroxide, cesium hydroxide and the like; alkali metal $C_{1-6}$ alkoxides such as lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide, sodium tert-butoxide, potassium tert-butoxide and the like; alkali metal thio $C_{1-6}$ alkoxides such as sodium thiomethoxide and the like; carbonates such as sodium carbonate, potassium carbonate, cesium carbonate and the like; hydrogencarbonates such as sodium hydrogencarbonate, potassium hydrogencarbonate and the like; acetates such as sodium acetate, potassium acetate and the like; phosphorates such as tripotassium phosphate, sodium phosphate and the like; and monohydrogen phosphates such as potassium monohydrogen phosphate, sodium monohydrogen phosphate and the like.

Examples of the organic base include aliphatic amines such as trimethylamine, triethylamine, N-methylmorpholine, N,N-diisopropylethylamine, diethylamine, diisopropylamine, cyclohexylamine, ethylene diamine, 1,8-diazabicyclo[5.4.0]undecene and the like; aromatic amines such as pyridine, picoline, N,N-dimethylaniline and the like, and basic amino acids such as arginine, lysine, ornithine and the like.

The base to be used in this step is preferably a tertiary amine, for example, triethylamine, N-methylmorpholine, N,N-diisopropylethylamine or the like.

Examples of the anhydride include carboxylic anhydrides such as acetic anhydride, propionic anhydride, butyric anhydride, pivalic anhydride, trifluoroacetic anhydride, benzoic anhydride and the like, sulfonic anhydrides such as methanesulfonic anhydride, p-toluenesulfonic anhydride, trifluoromethanesulfonic anhydride and the like, and di-tert-butyl dicarbonate.

Examples of the catalyst include N,N-dimethyl-4-aminopyridine, pyridine, 4-pyrrolidinopyridine and the like.

While the amount of the base to be used varies depending on the kind of the solvent, and the other reaction condition, it is generally 0.1 to 10 mol, preferably 1 to 5 mol, per 1 mol of compound (X). The organic base may be used as a solvent.

While the amount of the anhydride to be used varies depending on the kind of the solvent, and the other reaction condition, it is generally 0.1 to 10 mol, preferably 1 to 5 mol, per 1 mol of compound (X).

While the amount of the catalyst to be used varies depending on the kind of the solvent, and the other reaction condition, it is generally 0.001 to 1 mol, preferably 0.01 to 0.5 mol, per 1 mol of compound (X).

This reaction is carried out in the absence of a solvent, or in the presence of a solvent inert to the reaction.

The solvent inert to the reaction is not particularly limited as long as the reaction proceeds, and examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; alcohols such as methanol, ethanol, n-propanol, isopropanol, n-butanol, 2-butanol, tert-butanol, 3-methyl-1-butanol, 2-methyl-1-propanol, 1-pentanol, benzyl alcohol, 2-methoxyethanol, 2-ethoxyethanol, ethylene glycol and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like; halogenated hydrocarbons such as chloroform, dichloromethane, chloroform, carbon tetrachloride, 1,2-dichloroethane and the like; nitriles such as acetonitrile, propionitrile and the like; sulfones such as dimethylsulfone, sulfolane and the like; ketones such as acetone, ethyl methyl ketone, methyl isopropyl ketone, methyl butyl ketone and the like; esters such as ethyl acetate, isopropyl acetate, n-propyl acetate, n-butyl acetate, isobutyl acetate, methyl acetate, ethyl formate and the like; nitromethane; water and the like. These solvents may be used as a mixture at an appropriate ratio.

The reaction is carried out at generally −20° C.-150° C., preferably 0° C.-100° C.

While the reaction time varies depending on the kinds of the compound (X), anhydride, base, catalyst and solvent, and the reaction temperature, it is generally 1 min-24 hr, preferably 1 min-5 hr.

[Step 08-2]

The reaction of Step 08 can also be carried out by reacting compound (X) with an acid chloride in the presence of a base.

Examples of the base include those exemplified in the above-mentioned Step 08-1.

The base to be used in this step is preferably a tertiary amine, for example, triethylamine, N-methylmorpholine, N,N-diisopropylethylamine or the like.

Examples of the acid chloride include carboxyl chlorides such as acetyl chloride, propionyl chloride, butyryl chloride, pivaloyl chloride, benzoyl chloride and the like, sulfonyl chlorides such as methanesulfonyl chloride, p-toluenesulfonyl chloride, trifluoromethanesulfonyl chloride and the like, and acid chlorides such as ethyl chloroformate, isopropyl chloroformate, isobutyl chloroformate and the like.

While the amount of the base to be used varies depending on the kind of the solvent, and the other reaction condition, it is generally 0.1 to 10 mol, preferably 1 to 5 mol, per 1 mol of compound (X). The organic base may be used as a solvent.

While the amount of the acid chloride to be used varies depending on the kind of the solvent, and the other reaction condition, it is generally 0.1 to 10 mol, preferably 1 to 5 mol, per 1 mol of compound (X).

This reaction is carried out in the absence of a solvent, or in the presence of a solvent inert to the reaction.

Examples of the solvent inert to the reaction include those exemplified in the above-mentioned Step 08-1.

The reaction is carried out at generally −20° C.-150° C., preferably 0° C.-100° C.

While the reaction time varies depending on the kinds of the compound (X), acid chloride, base and solvent, and the reaction temperature, it is generally 1 min-24 hr, preferably 1 min-5 hr.

[Step 08-3]

The reaction of Step 08 can also be carried out by converting an acid to the acid chloride, and the reacting the obtained acid chloride with compound (X).

[Step 08-3-1]

The conversion of an acid to the acid chloride in Step 08-3 is carried out using a chlorinating agent. The reaction may be carried out in the presence of a catalyst, if desired.

Examples of the acid include carboxylic acids such as acetic acid, propionic acid, butyric acid, pivalic acid, trifluoroacetic acid, benzoic acid and the like; sulfonic acids such as methanesulfonic acid, p-toluenesulfonic acid, trifluoromethanesulfonic acid and the like, and the like.

Examples of the chlorinating agent include phosphorus oxychloride, oxalyl chloride, thionyl chloride, sulfuryl chloride, phosphorus trichloride, phosphorus pentachloride and the like.

Examples of the catalyst include N,N-dimethylformamide, pyridine, N,N-dimethyl-4-aminopyridine and the like.

While the amount of the chlorinating agent to be used varies depending on the kind of the solvent, and the other reaction condition, it is generally 0.1 to 10 mol, preferably 1 to 5 mol, per 1 mol of the acid. The chlorinating agent may be used as a solvent.

While the amount of the catalyst to be used varies depending on the kind of the solvent, and the other reaction condition, it is generally 0.001 to 1 mol, preferably 0.01 to 0.5 mol, per 1 mol of the acid.

The conversion to the acid chloride is carried out in the absence of a solvent, or in the presence of a solvent inert to the reaction.

Examples of the solvent inert to the reaction include those exemplified in the above-mentioned Step 08-1.

The conversion to the acid chloride is carried out at generally −20° C.-150° C., preferably 0° C.-100° C.

While the reaction time varies depending on the kinds of the acid, chlorinating agent, catalyst and solvent, and the reaction temperature, it is generally 1 min-24 hr, preferably 1 min-5 hr.

[Step 08-3-2]

The reaction of the acid chloride and compound (X) in Step 08-3 can be carried out in the presence of a base.

Examples of the base include those exemplified in the above-mentioned Step 08-1.

The base to be used in this step is preferably a tertiary amine, for example, triethylamine, N-methylmorpholine, N,N-diisopropylethylamine or the like.

While the amount of the acid chloride to be used varies depending on the kind of the solvent, and the other reaction condition, it is generally 0.1 to 10 mol, preferably 1 to 5 mol, per 1 mol of compound (X).

While the amount of the base to be used varies depending on the kind of the solvent, and the other reaction condition, it is generally 0.1 to 10 mol, preferably 1 to 5 mol, per 1 mol of compound (X). The organic base may be used as a solvent.

The reaction of the acid chloride and compound (X) is carried out in the absence of a solvent, or in the presence of a solvent inert to the reaction.

Examples of the solvent inert to the reaction include those exemplified in the above-mentioned Step 08-1.

The reaction of the acid chloride and compound (X) is carried out at generally −20° C.-150° C., preferably 0° C.-100° C.

While the reaction time varies depending on the kinds of the compound (X), acid chloride, base and solvent, and the reaction temperature, it is generally 1 min-24 hr, preferably 1 min-5 hr.

[Step 08-4]

The reaction of Step 08 can also be carried out by converting an acid to the active acid anhydride, and then reacting the obtained active acid anhydride with compound (X).

[Step 08-4-1]

The conversion of an acid to the active acid anhydride in Step 08-4 can be carried out using an active acid anhydride-forming agent, in the presence of a base.

Examples of the acid include those exemplified in the above-mentioned Step 08-3-1.

Examples of the base include those exemplified in the above-mentioned Step 08-1.

Examples of the active acid anhydride-forming agent include acid chlorides such as ethyl chloroformate, isopropyl chloroformate, pivaloyl chloride and the like, di-tert-butyl dicarbonate, carbonyldiimidazole and the like.

While the amount of the base to be used varies depending on the kind of the solvent, and the other reaction condition, it is generally 0.1 to 10 mol, preferably 1 to 5 mol, per 1 mol of the acid. The organic base may be used as a solvent.

While the amount of the active acid anhydride-forming agent to be used varies depending on the kind of the solvent, and the other reaction condition, it is generally 0.1 to 10 mol, preferably 1 to 5 mol, per 1 mol of the acid.

The conversion to the active acid anhydride is carried out in the absence of a solvent, or in the presence of a solvent inert to the reaction.

Examples of the solvent inert to the reaction include those exemplified in the above-mentioned Step 08-1.

The conversion to the active acid anhydride is carried out at generally −20° C.-150° C., preferably 0° C.-100° C.

While the reaction time varies depending on the kinds of the acid, base, the active acid anhydride-forming agent and solvent, and the reaction temperature, it is generally 1 min-24 hr, preferably 1 min-5 hr.

[Step 08-4-2]

The reaction of the active acid anhydride and compound (X) in Step 08-4 can be carried out in the presence of a base.

The reaction may be carried out in the presence of a catalyst, if desired.

Examples of the base include those exemplified in the above-mentioned Step 08-1.

The base is preferably a tertiary amine such as triethylamine, N-methylmorpholine, N,N-diisopropylethylamine and the like.

Examples of the catalyst include those exemplified in the above-mentioned Step 08-1.

While the amount of the base to be used varies depending on the kind of the solvent, and the other reaction condition, it is generally 0.1 to 10 mol, preferably 1 to 5 mol, per 1 mol of the active acid anhydride. The organic base may be used as a solvent.

While the amount of the active acid anhydride to be used varies depending on the kind of the solvent, and the other reaction condition, it is generally 0.1 to 10 mol, preferably 1 to 5 mol, per 1 mol of compound (X).

While the amount of the catalyst to be used varies depending on the kind of the solvent, and the other reaction condition, it is generally 0.001 to 1 mol, preferably 0.01 to 0.5 mol, per 1 mol of compound (X).

The reaction of the active acid anhydride and compound (X) is carried out in the absence of a solvent, or in the presence of a solvent inert to the reaction.

Examples of the solvent inert to the reaction include those exemplified in the above-mentioned Step 08-1.

The reaction of the active acid anhydride and compound (X) is carried out at generally −20° C.-150° C., preferably 0° C.-100° C.

While the reaction time varies depending on the kinds of the compound (X), active acid anhydride, base, catalyst and solvent, and the reaction temperature, it is generally 1 min-24 hr, preferably 1 min-5 hr.

[Step 08-5]

The reaction of Step 08 can also be carried out by reacting compound (X) with an acid using a condensing agent.

The reaction using a condensing agent can also be carried out in the presence of a base and an additive.

Examples of the acid include those exemplified in the above-mentioned Step 08-3-1.

Examples of the condensing agent include 1-[3-(dimethylamino)propyl]-3-ethylcarbodiimide or a hydrochloride thereof, N,N'-dicyclohexylcarbodiimide, N,N'-diisopropylcarbodiimide, 4-(4,6-dimethoxy-1,3,5-triazin-2-yl)-4-methylmorpholinium=chloride n hydrate, 1H-benzotriazol-1-yloxytris(dimethylamino)phosphonium hexafluorophosphate, 1H-benzotriazol-1-yloxytripyrrolidinophosphonium hexafluorophosphate, (7-azabenzotriazol-1-yloxy)tripyrrolidinophosphonium hexafluorophosphorate, chlorotripyrrolidinophosphonium hexafluorophosphorate, bromotris(dimethylamino)phosphonium hexafluorophosphorate, 3-(diethoxyphosphoryloxy)-1,2,3-benzotriazin-4(3H)-one, O-(benzotriazol-1-yl)-N,N,N',N'-tetramethyluronium hexafluorophosphate, O-(7-azabenzotriazol-1-yl)-N,N,N',N'-tetramethyluronium hexafluorophosphate, O—(N-succinimidyl)-N,N,N',N'-tetramethyluronium tetrafluoroborate, 0-(3,4-dihydro-4-oxo-1,2,3-benzotriazin-3-yl)-N,N,N',N'-tetramethyluronium tetrafluoroborate, S-(l-oxido-2-pyridyl)-N,N,N',N'-tetramethylthiuronium tetrafluoroborate, O-[2-oxo-1(2H)-pyridyl]-N,N,N',N'-tetramethyluronium tetrafluoroborate, {{[(1-cyano-2-ethoxy-2-oxoethylidene)amino]oxy}-4-morpholinomethylene}dimethylammonium hexafluorophosphate, 2-chloro-1,3-dimethylimidazoliniumhexafluorophosphate, 1-(chloro-1-pyrrolidinylmethylene) pyrrolidinium hexafluorophosphate, 2-fluoro-1,3-dimethylimidazoliniumhexafluorophosphate, fluoro-N,N,N',N'-tetramethylformamidinium hexafluorophosphorate and the like. The condensing agent may be used as a mixture of two or more kinds thereof, if desired.

Examples of the base include those exemplified in the above-mentioned Step 08-1.

The base is preferably a tertiary amine such as triethylamine, N-methylmorpholine, N,N-diisopropylethylamine and the like.

Examples of the additive include 1-hydroxybenzotriazole, 1-hydroxy-7-azabenzotriazole, N-hydroxysuccinimide, N,N'-disuccinimidyl carbonate and the like.

While the amount of the acid to be used varies depending on the kind of the solvent, and the other reaction condition, it is generally 0.1 to 10 mol, preferably 1 to 5 mol, per 1 mol of compound (X).

While the amount of the condensing agent to be used varies depending on the kind of the solvent, and the other reaction condition, it is generally 0.1 to 10 mol, preferably 1 to 5 mol, per 1 mol of compound (X).

While the amount of the base to be used varies depending on the kind of the solvent, and the other reaction condition, it is generally 0.1 to 10 mol, preferably 1 to 5 mol, per 1 mol of compound (X). The organic base may be used as a solvent.

While the amount of the additive to be used varies depending on the kind of the solvent, and the other reaction condition, it is generally 0.1 to 10 mol, preferably 1 to 5 mol, per 1 mol of compound (X).

The reaction using a condensing agent is carried out in the absence of a solvent, or in the presence of a solvent inert to the reaction.

The solvent inert to the reaction is not particularly limited as long as the reaction proceeds, and examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like; amides such as N,N-dimethylformamide, N,N-dimethylacetamide, formamide, hexamethylphosphoramide, N-methylpyrrolidone, 1,3-dimethyl-2-imidazolidinone and the like; halogenated hydrocarbons such as chloroform, dichloromethane, chloroform, carbon tetrachloride, 1,2-dichloroethane and the like; nitriles such as acetonitrile, propionitrile and the like; sulfoxides such as dimethyl sulfoxide and the like; sulfones such as dimethylsulfone, sulfolane and the like; ketones such as acetone, ethyl methyl ketone, methyl isopropyl ketone, methyl butyl ketone and the like; esters such as ethyl acetate, isopropyl acetate, n-propyl acetate, n-butyl acetate, isobutyl acetate, methyl acetate, ethyl formate and the like; nitromethane and the like. These solvents may be used as a mixture at an appropriate ratio.

The reaction using a condensing agent is carried out at generally −20° C.-150° C., preferably 0° C.-100° C.

While the reaction time varies depending on the kinds of the compound (X), acid, condensing agent, base, additive and solvent, and the reaction temperature, it is generally 1 min-24 hr, preferably 1 min-5 hr.

[Step 08-6]

The reaction of Step 08 can also be carried out by reacting compound (X) with an acid using a boric acid.

Examples of the acid include those exemplified in the above-mentioned Step 08-3-1.

Examples of the boric acid include tri-$C_{1-6}$ alkyl borates such as trimethyl borate, isopropyl borate, tris(2,2,2-trifluoroethyl) borate and the like; borontrifluoride-ethyl ether complex, 2,4,6-tris(3,4,5-trifluorophenyl)boroxine and boric acid.

While the amount of the acid to be used varies depending on the kind of the solvent, and the other reaction condition, it is generally 0.1 to 10 mol, preferably 1 to 5 mol, per 1 mol of compound (X).

While the amount of the boric acid to be used varies depending on the kind of the solvent, and the other reaction condition, it is generally 0.1 to 10 mol, preferably 1 to 5 mol s, per 1 mol of compound (X). The acid may be used as a solvent.

The reaction using a boric acid is carried out in the absence of a solvent, or in the presence of a solvent inert to the reaction.

Examples of the solvent inert to the reaction include those exemplified in the above-mentioned Step 08-5.

The reaction using a boric acid is carried out at generally −20° C.-150° C., preferably 0° C.-100° C.

While the reaction time varies depending on the kinds of the compound (X), acid, boric acid and solvent, and the reaction temperature, it is generally 1 min-24 hr, preferably 1 min-5 hr.

[Step 09]

In this step, compound (VIII) is produced by subjecting compound (IX) to a reduction reaction.

The reaction is preferably carried out in the presence of a reducing agent.

Examples of the reducing agent include metal borohydrides such as sodium borohydride, lithium borohydride, calcium borohydride, sodium cyanoborohydride, sodium triacetoxyborohydride and the like, triethylsilane and the like. The reducing agent may be used in the presence of an acid such as trifluoroborane-ether complex, aluminium chloride, trifluoroacetic acid and the like, if desired. Alternatively, as a reducing agent, hydrogen can be used together with a metal catalyst such as palladium carbon, platinum carbon, Raney nickel and the like. Among them, hydrogen is preferably used together with palladium carbon, as a reducing agent.

While the amount of the reducing agent to be used varies depending on the kind of the solvent, and the other reaction condition, it is generally 0.01 to 10 mol, preferably 1 to 5 mol, per 1 mol of compound (IX).

This reaction is advantageously carried out in the absence of a solvent, or in the presence of a solvent inert to the reaction.

The solvent inert to the reaction is not particularly limited as long as the reaction proceeds, and examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; alcohols such as methanol, ethanol, n-propanol, isopropanol, n-butanol, 2-butanol, tert-butanol, 3-methyl-1-butanol, 2-methyl-1-propanol, 1-pentanol, benzyl alcohol, 2-methoxyethanol, 2-ethoxyethanol, ethylene glycol and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like; amides such as N,N-dimethylformamide, N,N-dimethylacetamide, formamide, hexamethylphosphoramide, N-methylpyrrolidone, 1,3-dimethyl-2-imidazolidinone and the like; halogenated hydrocarbons such as chloroform, dichloromethane, chloroform, carbon tetrachloride, 1,2-dichloroethane and the like; nitriles such as acetonitrile, propionitrile and the like; sulfoxides such as dimethyl sulfoxide and the like; sulfones such as dimethylsulfone, sulfolane and the like; ketones such as acetone, ethyl methyl ketone, methyl isopropyl ketone, methyl butyl ketone and the like; esters such as ethyl acetate, isopropyl acetate, n-propyl acetate, n-butyl acetate, isobutyl acetate, methyl acetate, ethyl formate and the like; nitromethane; water; acetic acid and the like. These solvents may be used as a mixture at an appropriate ratio. The solvent is preferably methanol, or a mixture of ethanol and tetrahydrofuran at an any ratio.

The reaction is carried out at generally −20° C.-150° C., preferably 0° C.-100° C.

While the reaction time varies depending on the kinds of the reducing agent and solvent, and the reaction temperature, it is generally 1 min-24 hr, preferably 1 min-3 hr.

[Step 09-1]

In Step 08 and Step 09, Step 08 and Step 09 can be carried out in one step by subjecting compound (X) to a reduction reaction in the same manner as in Step 09, and thereby compound (VIII) can be produced.

The reduction reaction is generally carried out using a reducing agent. Examples of the reducing agent include those exemplified in the above-mentioned Step 09.

While the amount of the reducing agent to be used varies depending on the kind of the solvent, and the other reaction condition, it is generally 0.01 to 10 mol, preferably 1 to 5 mol, per 1 mol of the substrate compound (X).

The reduction reaction is advantageously carried out in the absence of a solvent, or in the presence of a solvent inert to the reaction.

Examples of the solvent inert to the reaction include those exemplified in the above-mentioned Step 09.

The reaction reduction is carried out at generally −20° C.-150° C., preferably 0° C.-100° C.

While the reaction time varies depending on the kinds of the reducing agent and solvent, and the reaction temperature, it is generally 1 min-48 hr, preferably 1 min-24 hr.

[Step 10]

In this step, PHBO is produced by subjecting compound (VIII) to a formylation reaction, and then a hydrolysis reaction, if-desired.

The formylation reaction is generally carried out using a formylating agent.

The formylation reaction is preferably carried out in the presence of an organic metal reagent. The hydrolysis reaction is generally carried out using an acid.

Examples of the organic metal reagent include those exemplified in the above-mentioned Step 07-2.

Preferable examples of the organic metal reagent include n-butyllithium, lithium diisopropylamide, lithium dicyclohexylamide, lithium 2,2,6,6-tetramethylpiperidide, diisopropylaminomagnesium chloride, diisopropylaminomagnesium bromide, 2,2,6,6-tetramethylpiperidinomagnesium chloride, and 2,2,6,6-tetramethylpiperidinomagnesium chloride-lithium chloride complex. Among them, more preferred are 2,2,6,6-tetramethylpiperidinomagnesium chloride, and 2,2,6,6-tetramethylpiperidinomagnesium chloride-lithium chloride complex.

Examples of the formylating agent include N,N-disubstituted formylamides such as dimethylformamide, N-formylmorpholine, N-formylpiperidine and the like; formate esters such as methyl formate, ethyl formate and the like; orthoformate esters such as orthomethyl formate, orthoethyl formate and the like; N-ethoxymethyleneaniline and the like. Among them, preferred are dimethylformamide and N-formylmorpholine. More preferred is N-formylmorpholine.

Examples of the acid include mineral acids such as hydrofluoric acid, hydrochloric acid, hydrobromic acid, hydroiodic acid, nitric acid, sulfuric acid, sulfurous acid and the like; phosphoric acid, phosphorus acid, carbonic acid, bicarbonic acid; carboxylic acids such as formic acid, acetic acid, trifluoroacetic acid, phthalic acid, fumaric acid, oxalic acid, tartaric acid, maleic acid, citric acid, succinic acid, malic acid and the like; acidic amino acids such as aspartic acid, glutamic acid and the like; and sulfonic acids such as methanesulfonic acid, trifluoromethanesulfonic acid, benzenesulfonic acid, p-toluenesulfonic acid, camphorsulfonic acid and the like. The acid may be used as a mixture of two or more kinds thereof, if desired.

While the amount of the organic metal reagent to be used varies depending on the kind of the solvent, and the other reaction condition, it is generally 0.1 to 100 mol, preferably 1 to 10 mol, per 1 mol of compound (VIII).

While the amount of the formylating agent to be used varies depending on the kind of the solvent, and the other reaction condition, it is generally 0.1 to 40 mol, preferably 1 to 10 mol, per 1 mol of compound (VIII).

While the amount of the acid to be used varies depending on the kind of the solvent, and the other reaction condition, it is generally 0.1 to 10000 mol, preferably 1 to 100 mol, per 1 mol of compound (VIII).

This reaction is advantageously carried out in the absence of a solvent, or in the presence of a solvent inert to the reaction.

The solvent inert to the reaction is not particularly limited as long as the reaction proceeds, and examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like, and the like. These solvents may be used as a mixture at an appropriate ratio. The solvent is preferably tetrahydrofuran.

The reaction is carried out at generally −100° C.-150° C., preferably −20° C.-50° C.

While the reaction time varies depending on the kinds of the compound (VIII), organic metal reagent, formylating agent, acid and solvent, and the reaction temperature, it is generally 1 min-24 hr, preferably 1 min-5 hr.

Compound A can be produced by subjecting PHBO produced in Step 10 to the reaction of the above-mentioned Step 06.

(Production Method N)

The present invention also provides a method of producing compound (II), which comprises (1) a step of reacting compound (XIII) with 4-(1H-pyrazol-1-yl)benzaldehyde to obtain compound (XII), and (2) a step of subjecting compound (XII) to a protection reaction of the hydroxy group, if desired, and then a reduction reaction.

The scheme of the above-mentioned reaction is shown below (hereinafter, a step of reacting compound (XIII) with 4-(1H-pyrazol-1-yl)benzaldehyde to obtain compound (XII) is referred to as Step (a), and a step of subjecting compound (XII) to a protection reaction of the hydroxy group, if desired, and then a reduction reaction is referred to as Step (b)).

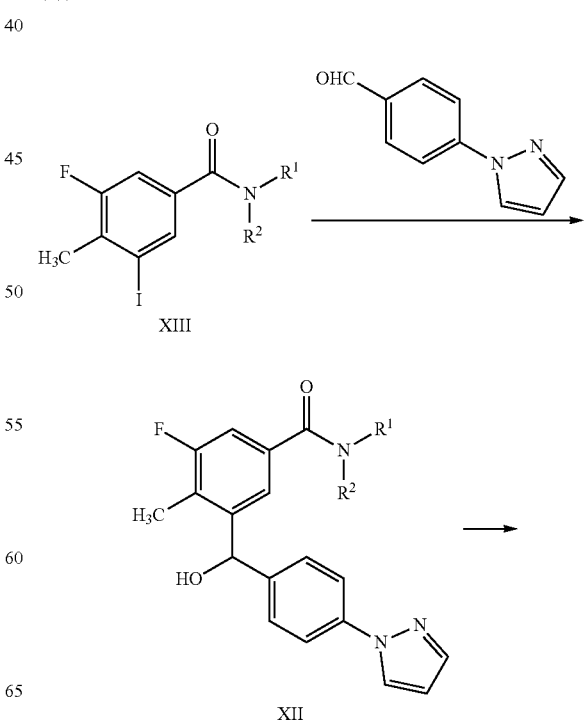

-continued

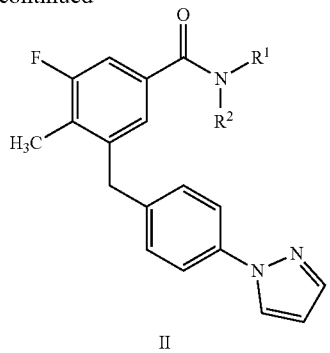

II wherein the symbols are as defined above.

Step (a) is carried out in the same manner as in the above-mentioned Step 07 (including Step 07-1 and Step 07-2).

Step (b) is carried out in the same manners as in the above-mentioned Step 08 (including Step 08-1, Step 08-2, Step 08-3, Step 08-4, Step 08-5 and Step 08-6) and the above-mentioned Step 09 (including Step 09-1).

Compound (II) in obtained Production Method N can be subjected to a step of Production Method C, Production Method D or Production Method E, if desired.

The raw material compound and reagent used and the compound obtained in each step may be each in the form of a salt, and examples of such salt include those similar to the salts of the above-mentioned compound (I) or (II), and the like.

When the compound obtained in each step is a free form, it can be converted to the objective salt according to a method known per se. When the compound obtained in each step is a salt, it can be converted to the free form or the objective other kind of salt according to a method known per se.

The compound obtained in each step can be used directly as the reaction solution or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, chromatography and the like.

When the raw material and reagent used in each step are commercially available, the commercially available product can also be used directly.

EXAMPLES

The present invention is explained in detail in the following by referring to Reference Examples and Examples, which are not to be construed as limitative, and the invention may be changed within the scope of the present invention. In the following Reference Examples and Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bonded silica gel. In HPLC (high performance liquid chromatography), C18 means use of octadecyl-bonded silica gel. The ratios of elution solvents are volume mixing ratios, unless otherwise specified.

In the following Reference Examples and Examples, the following abbreviations are used.
MS: mass spectrum
M: mol concentration
N: normality
$CDCl_3$: deuterochloroform
DMSO: dimethyl sulfoxide
DMSO-$d_6$: deuterodimethyl sulfoxide
$^1$H NMR: proton nuclear magnetic resonance spectrum
LC/MS: liquid chromatograph mass spectrometer
ESI: Electron Spray Ionization
APCI: atmospheric pressure chemical ionization
DMF: N,N-dimethylformamide
THF: tetrahydrofuran
DABCO: 1,4-diazabicyclo[2.2.2]octane $^1$H NMR was measured by Fourier-transform type NMR. For the analysis, ACD/SpecManager (trade name) and the like were used. Peaks with very mild protons such as a hydroxy group, an amino group and the like are not described.

MS was measured by LC/MS. As ionization method, ESI method or APCI method was used. The data indicates actual measured value (found). Generally, molecular ion peaks ([M+H]$^+$, [M−H]$^−$ and the like) are observed. For example, in the case of a compound having a tert-butoxycarbonyl group, a peak after elimination of a tert-butoxycarbonyl group or a tert-butyl group may be observed as a fragment ion. In the case of a compound having a hydroxy group, a peak after elimination of $H_2O$ may be observed as a fragment ion. In the case of a salt, a molecular ion peak or fragment ion peak of free form is generally observed.

The unit of sample concentration (c) for optical rotation ($[\alpha]_D$) is g/100 mL.

Elemental analysis value (Anal.) was described as calculated value (Calcd) and actual measured value (Found).

Reference Example 1

Synthesis of 3-fluoro-5-iodo-4-methylbenzoic Acid

3-Fluoro-4-methylbenzoic acid (150 g) was dissolved in sulfuric acid (1050 mL), and N-iodosuccinimide (284 g) was added thereto in four parts over 1 hr at the internal temperature of −10° C.-0° C. The mixture was reacted at 0° C.-10° C. for 6.5 hr, and kept stand overnight at the same temperature. Dietary salt (338 g) was dissolved in 1M hydrochloric acid (2.25 L) to prepared a solution, and the reaction solution was slowly poured into the prepared solution. The mixture was washed with 2-methoxy-2-methylpropane (300 mL) and water (150 mL). 2-Methoxy-2-methylpropane (1.5 L) was added thereto, and the mixture was subjected to liquid separation. The aqueous layer was subjected to re-extraction with 2-methoxy-2-methylpropane (1.2 L), and the organic layers were combined. The pH of the aqueous layer was adjusted to 5.5 by addition of water (750 mL) and 2M aqueous sodium hydroxide solution (120 mL). To the aqueous layer was added sodium sulfite (75 g), and the mixture was stirred at room temperature for 30 min. The pH of the aqueous layer was adjusted to 3.5 by addition of 3M hydrochloric acid (200 mL) and a small amount of 8M aqueous sodium hydroxide solution, and the mixture was subjected to liquid separation. The organic layer was washed with 10% brine (750 mL), and concentrated. To the mixture was added acetonitrile to adjust the volume to 600 mL, and water (675 mL) was added slowly dropwise thereto at room temperature. The mixture was stirred at room temperature for 2.5 hr, and the crystals were collected by filtration. The crystals were washed twice with acetonitrile/water (1:3, 300 mL) to give the title compound (200 g) as white crystals.

$^1$H NMR (600 MHz, DMSO-d6) δ 2.36 (d, J=2.3 Hz, 3H), 7.64 (dd, J=9.8, 1.1 Hz, 1H), 8.16 (s, 1H), 13.5 (br s, 1H).

Reference Example 2

Synthesis of 3-fluoro-5-iodo-4-methyl-N,N-di(propan-2-yl)benzamide

3-Fluoro-5-iodo-4-methylbenzoic acid (100 g) and N,N-dimethylformamide (2.61 g) were added to toluene (500 mL), and thionyl chloride (51.0 g) was added dropwise thereto at 75-85° C. The mixture was reacted at the same temperature for 1 hr, and concentrated. The volume of the concentrate was adjusted to 300 mL by addition of toluene, and the obtained solution was added slowly dropwise to a solution prepared by adding diisopropylamine (108 g) to tetrahydrofuran (500 mL) at 0° C.-15° C. The mixture was reacted at the same temperature for 1 hr, ethyl acetate (200 mL) and water (500 mL) were added thereto, and the mixture was subjected to liquid separation. The organic layer was washed successively with 10% brine (500 mL), 1M hydrochloric acid (500 mL) and 10% brine (500 mL), and concentrated. The volume of the concentrate was adjusted to 500 mL by addition of acetonitrile, and water (750 mL) was added slowly dropwise to the obtained solution at room temperature. The mixture was stirred at room temperature for 3 hr, and the crystals were collected by filtration. The crystals were washed twice with acetonitrile/water (1:3, 200 mL) to give the title compound (121 g) as white crystals.

$^1$H NMR (600 MHz, CDCl3) δ 1.17 (br s, 6H), 1.49 (br s, 6H), 2.37 (d, J=2.3 Hz, 3H), 3.52 (br s, 1H), 3.79 (br s, 1H), 6.97 (dd, J=9.1, 1.5 Hz, 1H), 7.55 (s, 1H).

Reference Example 3

Synthesis of 3-fluoro-4-methyl-N,N-di(propan-2-yl)-5-(4,4,5,5-tetramethyl-1,3,2-dioxaborolan-2-yl)benzamide 3-Fluoro-5-iodo-4-methyl-N,N-di(propan-2-yl)benzamide (25 g), bis(pinacolato)diboron (22.7 g) and 1,1'-bis(diphenylphosphino)ferrocene (1.91 g) were added to N,N-dimethylformamide (250 mL), and the mixture was subjected to decompression and nitrogen substitution three times. To the mixture were added potassium acetate (20.3 g) and palladium(II) chloride (610 mg), and the mixture was again subjected to decompression and nitrogen substitution three times. The mixture was reacted under nitrogen atmosphere at 80° C.-90° C. for 4 hr. The reaction solution was allowed to cool to room temperature, and activated carbon (1.25 g) was added thereto. The mixture was stirred, and the insoluble substance and activated carbon were removed by filtration. The insoluble substance and activated carbon were washed with ethyl acetate (250 mL), and the washing and the filtrate was combined. 10% Brine (125 mL) was added thereto, and the mixture was subjected to liquid separation. To the aqueous layer were added water (125 mL) and ethyl acetate (250 mL), and the mixture was subjected to re-extraction. The organic layers were combined, and washed three times with water (125 mL). The mixture was concentrated, and the residue was purified by silica gel column chromatography (ethyl acetate/n-hexane 1:15). The purified product was suspended in ethyl acetate/n-hexane (1:9, 56 mL). The suspension was stirred under ice bath, and the crystals were collected by filtration to give the title compound (22.2 g) as white crystals.

$^1$H NMR (600 MHz, CDCl3) δ 1.26 (s, 6H), 1.34 (s, 12H), 1.54-1.63 (m, 6H), 2.46 (d, J=2.3 Hz, 3H), 3.51 (br s, 1H), 3.86 (br s, 1H), 6.96-7.08 (m, 1H), 7.50 (s, 1H).

Reference Example 4

Synthesis of 3-fluoro-4-methyl-N,N-di(propan-2-yl)-5-[4-(1H-pyrazol-1-yl)benzyl]benzamide 3-Fluoro-4-methyl-N,N-di(propan-2-yl)-5-(4,4,5,5-tetramethyl-1,3,2-dioxaborolan-2-yl)benzamide (20.0 g) was added to a mixture of N,N-dimethylformamide (150 mL) and water (150 mL). To the mixture were added 1-[4-(chloromethyl)phenyl]-1-H-pyrazole (11.7 g) and sodium carbonate (11.7 g), and the mixture was subjected to decompression and nitrogen substitution three times. To the mixture was added [1,1'-bis(diphenylphosphino)ferrocene]palladium(II) dichloride (757 mg), and the mixture was again subjected to decompression and nitrogen substitution three times. The mixture was reacted at 80° C. for 4 hr, [1,1'-bis(diphenylphosphino)ferrocene]palladium(II) dichloride (282 mg) was added again thereto, and the mixture was reacted for 1.5 hr. To the reaction solution was added again 1-[4-(chloromethyl)phenyl]-1-H-pyrazole (1.06 g), and the mixture was reacted for 30 min, and allowed to cool to room temperature. The insoluble substance was removed by filtration from the reaction solution, and the mixture was washed with ethyl acetate (200 mL). The filtrate and washing were combined, and subjected to liquid separation. The aqueous layer was subjected to re-extraction with ethyl acetate (200 mL), and the organic layers were combined, and washed three times with 10% brine (100 mL). To the organic layer was added activated carbon (2 g), the mixture was stirred at room temperature, and the activated carbon was removed by filtration. The filtrate was concentrated, and the concentrated residue was purified by silica gel column chromatography (ethyl acetate/n-hexane 1:4 to 1:3). The concentrated residue was stirred while suspended in n-heptane, and collected by filtration to give the title compound (7.82 g) as white crystals.

$^1$H NMR (600 MHz, DMSO-d6) δ 1.12 (br s, 6H), 1.49 (br s, 6H), 2.16 (d, J=1.5 Hz, 3H), 3.49 (br s, 1H), 3.84 (br s, 1H), 4.03 (s, 2H), 6.45 (t, J=2.1 Hz, 1H), 6.90 (s, 1H), 6.92 (d, J=9.4 Hz, 1H), 7.19 (d, J=8.3 Hz, 2H), 7.60 (d, J=8.7 Hz, 2H), 7.71 (d, J=1.5 Hz, 1H), 7.89 (d, J=2.6 Hz, 1H).

Reference Example 5

Synthesis of 3-fluoro-4-methyl-N,N-di(propan-2-yl)-5-[4-(1H-pyrazol-1-yl)benzyl]benzamide 3-Fluoro-5-iodo-4-methyl-N,N-di(propan-2-yl)benzamide (140 g), bis(pinacolato)diboron (108 g) and potassium acetate (114 g) were added to dimethyl sulfoxide (700 mL), and the mixture was subjected to decompression and nitrogen substitution three times. To the mixture was added [1,1'-bis(diphenylphosphino)ferrocene]palladium(II) dichloride (4.23 g), and the mixture was again subjected to decompression and nitrogen substitution three times. The mixture was reacted under nitrogen atmosphere at 105° C.-115° C. for 4 hr. The reaction solution was cooled to 50° C., ethyl acetate (1.4 L) and 20% brine (1.4 L) were added thereto, and the mixture was subjected to liquid separation. To the organic layer was added activated carbon (14 g), the mixture was stirred, and the activated carbon was removed by filtration. The activated carbon was washed with ethyl acetate (280 mL), and the filtrate and washing were combined, and washed twice with 10% brine (700 mL). The organic layer was concentrated, dimethoxyethane was added thereto to adjust the volume to 700 mL. To this solution were added water (700 mL), sodium carbonate (81.6 g) and 1-[4-(chloromethyl)phenyl]-1-H-pyrazole (77.9 g), and the mixture was subjected to decompression and nitrogen substitution three times. To the mixture was added [1,1'-bis(diphenylphosphino)ferrocene]palladium(II) dichloride (2.82 g), and the mixture was again subjected to decompression and nitrogen substitution three times. The mixture was reacted at 70° C.-80° C. for 3 hr, and cooled to 50° C. Ethyl acetate (1.12 L), water (1.12 L) and tetrahydrofuran (1.12 L) were added thereto, and the mixture was subjected to liquid separation. To the organic layer were added ethyl acetate (280 mL), tetrahydrofuran (280 mL) and 0.5M hydrochloric acid (700 mL), and the mixture was subjected to liquid separation. The organic layer was washed successively with 10% brine (700 mL), 28% aqueous ammonia (700 mL) and 10% brine (700 mL×2). To the organic layer was added activated carbon (14 g), the mixture was stirred, and the activated carbon was removed by filtration. The activated carbon was washed with ethanol (280 mL), and the filtrate and washing were combined, and concentrated. Ethanol was added thereto to adjust the volume to 1.4 L, and water (700 mL) was added slowly dropwise thereto at 40° C.-50° C. The mixture was cooled to room temperature, and stirred for 3 hr, and the crystals were collected by filtration. The crystals were washed twice with ethanol/water (1:2, 280 mL), the obtained wet crystals were added to ethyl acetate (420 mL), and n-heptane (840 mL) was added slowly dropwise thereto at 40° C. The mixture was cooled to room temperature, and stirred for 3.5 hr, and the crystals were collected by filtration. The crystals were washed twice with ethyl acetate/n-heptane (1:4, 280 mL) to give the title compound (123 g) as brown crystals.

Reference Example 6

Synthesis of 5-N,N-di(propan-2-yl)carbamoyl-3-fluoro-2-methylphenylboronic Acid

Under nitrogen atmosphere, at −5° C., to a solution of 3-fluoro-5-iodo-4-methyl-N,N-di(propan-2-yl)benzamide (5.0 g) in tetrahydrofuran (35 mL) was added dropwise 1.34M isopropylmagnesium chloride-lithium chloride tetrahydrofuran solution (16.2 mL). The mixture was stirred at the same temperature for 30 min, and tetrahydrofuran solution (15 mL) of triisopropyl borate (7.1 mL) was added thereto. The mixture was stirred at room temperature for 30 min. The reaction mixture was cooled to 5° C., and 2M hydrochloric acid (50 mL) was added dropwise thereto at the temperature not exceeding 35° C. To the mixture was added ethyl acetate (50 mL), and the mixture was subjected to liquid separation. To the aqueous layer was added ethyl acetate (25 mL), and the mixture was subjected to re-extraction. The organic layers were combined, and washed twice with 2M hydrochloric acid (25 mL) and 10% brine (25 mL). The mixture was concentrated, and the residue was purified by silica gel column chromatography to give the title compound (337 mg) as white crystals.

1H NMR (600 MHz, DMSO-d6) δ 1.12 (br s, 3H), 1.41 (br s, 3H), 2.32 (d, J=2.27 Hz, 3H), 3.65 (br s, 2H), 7.04 (dd, J=10.01, 1.32 Hz, 1H), 7.13 (d, J=1.51 Hz, 1H), 8.31 (s, 2H).

Reference Example 7

Synthesis of 3-fluoro-4-methyl-N,N-di(propan-2-yl)-5-[4-(H-pyrazol-1-yl)benzyl]benzamide Under nitrogen atmosphere, at −5° C., to a solution of 3-fluoro-5-iodo-4-methyl-N,N-di(propan-2-yl)benzamide (100 g) in tetrahydrofuran (750 mL) was added dropwise 1.34M isopropylmagnesium chloride-lithium chloride tetrahydrofuran solution (330 mL). The mixture was stirred at the same temperature for 30 min, and tetrahydrofuran solution (250 mL) of triisopropyl borate (126 mL) was added thereto. The mixture was stirred at room temperature for 1 hr, the reaction mixture was cooled to 5° C., and 2M hydrochloric acid (1000 mL) was added dropwise thereto at the temperature not exceeding 35° C. To the mixture was added ethyl acetate (1000 mL), and the mixture Was subjected to liquid separation. To the aqueous layer was ethyl acetate (500 mL), and the mixture was subjected to re-extraction. The organic layers were combined, washed twice with 2M hydrochloric acid (500 mL) and 10% brine (500 mL), and concentrated. To the concentrated residue were added tetrahydrofuran (600 mL), 1-[4-(chloromethyl)phenyl]-1-H-pyrazole (47.7 g) and triphenylphosphine (2.89 g). To this solution was added aqueous solution (400 mL) of sodium carbonate (58.4 g), and the mixture was subjected to decompression and nitrogen substitution three times. To the mixture was added palladium(II) acetate (618 mg), and the mixture was again subjected to decompression and nitrogen substitution three times. The mixture was reacted at 55° C.-65° C. for 30 min, and cooled to 30° C. Ethyl acetate (1000 mL) and water (500 mL) were added thereto, and the mixture was subjected to liquid separation. The organic layer was washed successively with 1M hydrochloric acid (500 mL), 10% brine (500 mL), 14% aqueous ammonia (500 mL×2) and 10% brine (500 mL). To the organic layer was added activated carbon (10.0 g), the mixture was stirred at room temperature for 30 min. The activated carbon was removed by filtration, and washed three times with ethanol (200 mL), and the filtrate and washing were concentrated. To the concentrated residue was added ethanol (1000 mL), and water (500 mL) was added slowly dropwise thereto at 55° C.-65° C. The mixture was cooled to 0° C.-10° C., and the crystals were collected by filtration, and washed twice with ethanol/water (1:2, 200 mL). To the wet crystals was added ethyl acetate (300 mL), and n-heptane (900 mL) was added slowly dropwise thereto at 45° C.-55° C. The mixture was cooled to 0° C.-10° C., and the crystals were collected by filtration, and washed twice with ethyl acetate/n-heptane (1:4, 200 mL) to give the title compound (86.1 g) as pale-yellow crystals.

Reference Example 8

Synthesis of tert-butyl-3-fluoro-5-iodo-4-methylbenzoate

3-Fluoro-5-iodo-4-methylbenzoic acid (30 g) and 4-dimethylaminopyridine (13.1 g) were added to t-butanol/tetrahydrofuran (9:1, 300 mL), and then di-tert-butyl-dicarbonate (46.7 g) was added thereto. The mixture was stirred at 50° C. for 30 min, di-tert-butyl-dicarbonate (11.7 g) was added again thereto, and the mixture was stirred at 50° C. for 30 min. To the reaction solution were added ethyl acetate (300 mL), water (150 mL) and 10% brine (150 mL), and the mixture was subjected to liquid separation. The organic layer was washed successively with 5% aqueous sodium bicarbonate solution (150 mL) and 10% brine (150 mL).

Activated carbon (3 g) was added thereto at room temperature, the mixture was stirred at the same temperature for 30 min, and the activated carbon was removed by filtration. The filtrate and washing were concentrated, and to the concentrated residue was added ethanol (90 mL). Water (180 mL) was added slowly dropwise thereto at 40° C. The mixture was cooled to room temperature, and the crystals were collected by filtration, and washed twice with ethanol/water (1:4, 60 ml.) to give the title compound (35.0 g) as white crystals.

$^1$H NMR (600 MHz, CDCl3-d) δ 1.58 (s, 9H), 2.40 (d, J=2.3 Hz, 3H), 7.26 (s, 1H), 8.20 (s, 1H).

Example 1

Synthesis of 3-fluoro-2-formyl-4-methyl-N,N-di(propan-2-yl)-5-[4-(1H-pyrazol-1-yl)benzyl]benzamide Under nitrogen atmosphere, at −5° C., to a solution of 3-fluoro-4-methyl-N,N-di(propan-2-yl)-5-[4-(1H-pyrazol-1-yl)benzyl]benzamide (10.0 g) and N,N-dimethylformamide (2.95 mL) in tetrahydrofuran (150 mL) was added dropwise 1.73M lithium diisopropylamide tetrahydrofuran/n-heptane/ethylbenzene solution (17.6 mL). The mixture was stirred at the same temperature for 1 hr, N,N-dimethylformamide (2.95 mL) and 1.73M lithium diisopropylamide tetrahydrofuran/n-heptane/ethylbenzene solution (17.6 mL) were added successively dropwise thereto. The mixture was stirred at the same temperature for 1 hr, and N,N-dimethylformamide (2.16 mL) and 1.73M lithium diisopropylamide tetrahydrofuran/n-heptane/ethylbenzene solution (10.3 mL) were added successively dropwise thereto. The mixture was stirred at the same temperature for 1 hr, N,N-dimethylformamide (1.38 mL) and 1.73M lithium diisopropylamide tetrahydrofuran/n-heptane/ethylbenzene solution (7.34 mL) were added successively dropwise thereto. The mixture was stirred at the same temperature for 1 hr, 2M hydrochloric acid (100 mL) was added dropwise thereto at the temperature not exceeding 10° C., and the mixture was subjected to liquid separation. To the aqueous layer was added ethyl acetate (100 mL), and the mixture was subjected to re-extraction. The organic layers were combined, and washed successively with 2M hydrochloric acid (50 mL×2), 5% aqueous sodium hydrogencarbonate solution (50 mL), 28% aqueous ammonia (50 mL) and 10% brine (50 mL). To the organic layer was added activated carbon (1.0 g), and the mixture was stirred at room temperature for 30 min. The activated carbon was removed by filtration, and washed three times with ethyl acetate (20 mL), and the filtrate and washing were concentrated. To the concentrated residue was added ethyl acetate (30 mL), and n-heptane (40 mL) was added slowly dropwise thereto at 45° C.-55° C. The mixture was cooled to 0° C.-10° C., and the crystals were collected by filtration, and washed three times with ethyl acetate/n-heptane (2:5, 5 mL) to give the title compound (7.32 g) as gray crystals.

Example 2

Synthesis of 3-fluoro-2-formyl-4-methyl-5-[4-(1H-pyrazol-1-yl)benzyl]benzoic acid 1,4-diazabicyclo[2.2.2]octane Salt To a mixture of 73% sulfuric acid (750 mL) and sodium bromide (24.4 g) was added 3-fluoro-2-formyl-4-methyl-N,N-di(propan-2-yl)-5-[4-(1H-pyrazol-1-yl)benzyl]benzamide (50.0 g). The mixture was reacted at 95° C.-105° C. for 7 hr, and cooled to 0° C.-10° C., and toluene (250 mL) and tetrahydrofuran (250 mL) were added thereto. To the mixture was added dropwise 8M aqueous sodium hydroxide solution (1000 mL) at 30° C. or below. Toluene (150 mL) and tetrahydrofuran (150 mL) were added thereto, and the mixture was subjected to liquid separation. To the aqueous layer were added toluene (125 mL) and tetrahydrofuran (125 mL) and 8M aqueous sodium hydroxide solution (250 mL), and the mixture was subjected to re-extraction. The organic layers were combined, 0.5M aqueous sodium hydroxide solution (500 mL) and 8M aqueous sodium hydroxide solution (50 mL) were added thereto to adjust the pH of the aqueous layer to 12.5 or more, and the mixture was subjected to liquid separation. To the organic layer was added 0.5M aqueous sodium hydroxide solution (250 mL), and the mixture was subjected to re-extraction. The aqueous layers were combined, toluene (125 mL) and tetrahydrofuran (125 mL) were added thereto, and the mixture was subjected to liquid separation. To the aqueous layer was added 6M hydrochloric acid (58 mL) to adjust the pH of the aqueous layer to 6.5, and ethyl acetate (500 mL) was added thereto. To the mixture was added 6M hydrochloric acid (11 mL) to adjust the pH of the aqueous layer to 5.0, and the mixture was subjected to liquid separation. To the aqueous layer was added ethyl acetate (500 mL). To the mixture was added 6M hydrochloric acid (2.0 mL) to adjust the pH to 5.0, and the mixture was subjected to liquid separation. The organic layers were combined, and washed with 10% brine (250 mL). To the organic layer was added activated carbon (5.0 g), and the mixture was stirred at room temperature for 30 min. The activated carbon was removed by filtration, and washed three times with ethyl acetate (100 mL), and filtrate and washing were concentrated. To the concentrated residue was added ethyl acetate (400 mL), and 1,4-diazabicyclo[2.2.2]octane (12.0 g) was added thereto at 45° C.-55° C. The mixture was cooled to 0° C.-10° C., and the crystals were collected by filtration, and washed three times with cooled ethyl acetate (50 mL) to give the title compound (40.1 g) as pale-yellow crystals.

Example 3

Synthesis of 1,5-anhydro-2,4-dideoxy-2-(4-fluoro-5-methyl-1-oxo-6-(4-(1H-pyrazol-1-yl)benzyl)-1,3-dihydro-2H-isoindol-2-yl)-L-threo-pentitol To a solution of 3-fluoro-2-formyl-4-methyl-5-[4-(1H-pyrazol-1-yl)benzyl]benzoic acid 1,4-diazabicyclo[2.2.2]octane salt (5.00 g) and 2-amino-1,5-anhydro-2,4-dideoxy-L-threo-pentitol (1.37 g) in tetrahydrofuran (50 mL) was added acetic acid (5 mL). The mixture was stirred at 15° C.-35° C. for 15 min, and sodium triacetoxyborohydride (4.70 g) was added thereto at the same temperature. The mixture was stirred at 15° C.-35° C. for 30 min, and warmed to 50° C.-60° C. The mixture was reacted at the same temperature for 2 hr, and cooled to 15° C.-35° C., and ethyl acetate (50 mL) was added thereto. To the mixture was added 2M hydrochloric acid (50 mL), and the mixture was subjected to liquid separation. To the aqueous layer was added ethyl acetate (25 mL), and the mixture was subjected to re-extraction. The organic layers were combined, and washed successively with water (25 mL), 20% aqueous potassium carbonate solution (25 mL×2), 5% aqueous ammonia (25 mL×2) and 20% brine (25 mL). To the organic layer were added magnesium sulfate (10 g), activated carbon (0.5 g) and ethyl acetate (5 mL), the mixture was stirred at room temperature for 30 min, and the insoluble substance was removed by filtration. The mixture was washed three times with ethyl acetate (15 mL), and concentrated. To the concentrated residue were added ethanol (25 mL) and tetrahydrofuran (12.5 mL), and the mixture was heated to 55° C.-65° C. to dissolve the precipitated crystals. The mixture was stirred 40° C.-50° C. for 2 hr, which resulted in crystallization. Water (75 mL) was added slowly dropwise thereto at 20° C.-30° C. The mixture was cooled to 0° C.-10° C., and the crystals were collected by filtration, and washed twice with ethanol/water (1:2, 15 mL) to give crude crystals (3.93 g) of the title compound as pale brown crystals. To the crude 1,5-anhydro-2,4-dideoxy-2-(4-fluoro-5-methyl-1-oxo-6-(4-(1H-pyrazol-1-yl)benzyl)-1,3-dihydro-2H-isoindol-2-yl)-L-threo-pentitol (3 g) were added 2-butanone (27 mL) and dimethyl sulfoxide (3 mL). The mixture was heated to 65° C.-75° C. for dissolution, and the insoluble substance was removed by filtration. The mixture was washed with 2-butanone (6 mL). To the mixture was added slowly dropwise n-heptane (30 mL) at 60° C.-70° C., and the mixture was stirred at the same temperature for 2 hr or more, which resulted in crystallization. To the mixture was added slowly dropwise n-heptane (30 mL) at 60° C.-70° C., and the mixture was stirred at the same temperature for 4 hr or more. The mixture was cooled to 0° C.-10° C., and the crystals were collected by filtration, and washed twice with 2-butanone/n-heptane (1:3, 9 mL) to give the recrystallized product (2.71 g) of the title compound as white crystals.

Example 4

Synthesis of 3-fluoro-2-formyl-4-methyl-N,N-di(propan-2-yl)-5-[4-(1H-pyrazol-1-yl)benzyl]benzamide Under nitrogen atmosphere, at 20° C.-30° C., to a solution of 3-fluoro-4-methyl-N,N-di(propan-2-yl)-5-[4-(1H-pyrazol-1-yl)benzyl]benzamide (5.00 g) and N,N-dimethylformamide (1.27 mL) in tetrahydrofuran (75 mL) was added diisopropylamine (9.44 mL). The mixture was cooled to −10° C.-0° C., and 1.6M n-butyllithium n-hexane solution (8.68 mL) was added dropwise thereto. The mixture was stirred at the same temperature for 1 hr, and N,N-dimethylformamide (9.44 mL) and 1.6M n-butyllithium n-hexane solution (7.89 mL) were added successively dropwise thereto. The mixture was stirred at the same temperature for 1 hr, and N,N-dimethylformamide (8.68 mL) and 1.6M n-butyllithium n-hexane solution (5.52 mL) were added successively dropwise thereto. The mixture was stirred at the same temperature for 1 hr, and 2M hydrochloric acid (50 mL) was added dropwise thereto at the temperature not exceeding 10° C. To the mixture was added ethyl acetate (37.5 mL), and the mixture was subjected to liquid separation. The organic layer was washed successively with 2M hydrochloric acid (25 mL×2), water (25 mL), 20% aqueous potassium carbonate solution (25 mL) and 10% brine (25 mL). To the organic layer was added activated carbon (0.50 g), and the mixture was stirred at room temperature for 30 min. The activated carbon was removed by filtration, and washed three times with ethyl acetate (10 mL), and the filtrate and washing were concentrated. To the concentrated residue was added ethyl acetate (25 mL), and n-heptane (37.5 mL) was added slowly dropwise thereto at 60° C.-70° C. The mixture was cooled to 0° C.-10° C., and the crystals were collected by filtration, and washed twice with ethyl acetate/n-heptane (1:3, 10 mL) to give the title compound (3.98 g) as white-pale gray crystals.

$^1$H NMR (600 MHz, CDCl3) δ 1.06 (br s, 6H), 1.58 (br s, 6H), 2.22 (br d, J=1.51 Hz, 3H), 3.50 (tt, J=13.08 Hz, 6.75 Hz, 2H), 4.06 (br s, 2H), 6.44-6.50 (m, 1H), 6.82 (s, 1H), 7.18 (br d, J=8.31 Hz, 2H), 7.62 (br d, J=8.69 Hz, 2H), 7.72 (br d, J=1.13 Hz, 1H), 7.90 (d, J=2.27 Hz, 1H), 10.35 (s, 1H).

Example 5

Synthesis of 3-fluoro-2-formyl-4-methyl-5-[4-(1H-pyrazol-1-yl)benzyl]benzoic acid 1,4-diazabicyclo[2.2.2]octane salt To a mixture of 3-fluoro-2-formyl-4-methyl-N,N-di(propan-2-yl)-5-[4-(1H-pyrazol-1-yl)benzyl]benzamide (30.0 g) and 48% hydrobromic acid (450 mL) was added p-toluenesulfonic acid monohydrate (135.4 g). The mixture was reacted at 95° C.-105° C. for 7 hr, and cooled to 50° C.-60° C., and water (150 mL) was added thereto. The mixture was cooled to 10° C.-30° C., toluene (150 mL) was added thereto, and 8M aqueous sodium hydroxide solution (150 mL) was added dropwise thereto at 10° C.-30° C. To the mixture was added tetrahydrofuran (300 mL), and 8M aqueous sodium hydroxide solution (420 mL) was added dropwise thereto at 10° C.-30° C. to adjust the pH to 2 to 3. To the mixture was added toluene (150 mL), and the mixture was subjected to liquid separation. To the aqueous layer were added toluene (75 mL) and tetrahydrofuran (75 mL), and the mixture was subjected to re-extraction. The organic layers were combined, and washed twice with water (150 mL). To the organic layer were added 2-butanone (300 mL) and 5% aqueous sodium hydrogencarbonate solution (300 mL), and the mixture was heated to 30° C.-40° C., and subjected to liquid separation. To the organic layer was added 5% aqueous sodium hydrogencarbonate solution (150 mL), and the mixture was heated to 30° C.-40° C., and subjected to re-extraction (1st). To the organic layer was added 5% aqueous sodium hydrogencarbonate solution (150 mL), and the mixture was heated to 30° C.-40° C., and subjected to re-extraction (2nd). The aqueous layers were combined, ethyl acetate (300 mL) was added thereto, and 6M hydrochloric acid (60 mL) was added dropwise thereto at 20° C.-30° C. to adjust the pH of the aqueous layer to 2 to 3. The mixture was subjected to liquid separation, and the organic layer was washed twice with water (150 mL). To the organic layer was added activated carbon (3.0 g), and the mixture was stirred at room temperature for 30 min. The activated carbon was removed by filtration, and washed three times with ethyl acetate (90 mL), and the filtrate and washing were concentrated. To the concentrated residue were added ethyl acetate (150 mL), acetonitrile (30 mL) and tetrahydrofuran (60 mL), and 1,4-diazabicyclo[2.2.2]octane (7.19 g) was added thereto at 45° C.-55° C. The mixture was cooled to 0° C.-10° C., and the crystals were collected by filtration, and washed twice with ethyl acetate (90 mL) to give the title compound (21.9 g) as pale-yellow crystals.

Example 6

Synthesis of 3-fluoro-2-formyl-4-methyl-5-[4-(1H-pyrazol-1-yl)benzyl]benzoic acid 1,4-diazabicyclo[2.2.2]octane salt To a mixture of 3-fluoro-2-formyl-4-methyl-N,N-di(propan-2-yl)-5-[4-(1H-pyrazol-1-yl)benzyl]benzamide (30.0 g) and 48% hydrobromic acid (450 mL) was added p-toluenesulfonic acid monohydrate (135.4 g). The mixture was reacted at 95° C.-105° C. for 7 hr, and cooled to 50° C.-60° C., and water (150 mL) was added thereto. The mixture was cooled to 10° C.-30° C., toluene (150 mL) was added thereto, and 8M aqueous sodium hydroxide solution (150 mL) was added dropwise thereto at 10° C.-30° C. To the mixture was added tetrahydrofuran (300 mL), and 8M aqueous sodium hydroxide solution (430 mL) was added dropwise thereto at 10° C.-30° C. to adjust the pH to 2 to 3. To the mixture was added toluene (150 mL), and the mixture was subjected to liquid separation. To the aqueous layer were added toluene (75 mL) and tetrahydrofuran (75 mL), and the mixture was subjected to re-extraction. The organic layers were combined, and washed twice with water (150 mL). To the organic layer were added 2-butanone (300 mL) and 5% aqueous sodium hydrogencarbonate solution (300 mL), and the mixture was heated to 30° C.-40° C., and subjected to liquid separation. To the organic layer was added 5% aqueous sodium hydrogencarbonate solution (300 mL), and the mixture was heated to 30° C.-40° C., and subjected to re-extraction (1st). To the organic layer was added 5% aqueous sodium hydrogencarbonate solution (150 mL), and the mixture was heated to 30° C.-40° C., and subjected to re-extraction (2nd). The aqueous layers were combined, toluene (150 mL) and tetrahydrofuran (150 mL) were added thereto, and 6M hydrochloric acid (57 mL) was added dropwise thereto at 20° C.-30° C. to adjust the pH of the aqueous layer to 2 to 3. The mixture was subjected to liquid separation, and the organic layer was washed with water (150 mL). To the organic layer were added 2-butanone (300 mL) and 5% aqueous sodium hydrogencarbonate solution (300 mL), and the mixture was heated to 30° C.-40° C., and subjected to liquid separation. To the organic layer was added 5% aqueous sodium hydrogencarbonate solution (150 mL), and the mixture was heated to 30° C.-40° C., and subjected to re-extraction (1st). To the organic layer was added 5% aqueous sodium hydrogencarbonate solution (150 mL), and the mixture was heated to 30° C.-40° C., and subjected to re-extraction (2nd). The aqueous layers were combined, toluene (150 mL) and tetrahydrofuran (150 mL) were added thereto, and 6M hydrochloric acid (55 mL) was added dropwise thereto at 20° C.-30° C. to adjust the pH of the aqueous layer to 2 to 3. The mixture was subjected to re-extraction, and the organic layer was washed twice with water (150 mL). To the organic layer was added activated carbon (3.0 g), and the mixture was stirred at room temperature for 30 min. The activated carbon was removed by filtration, and washed three times with tetrahydrofuran (90 mL), and the filtrate and washing were concentrated. To the concentrated residue were added ethyl acetate (150 mL), acetonitrile (30 mL) and tetrahydrofuran (60 mL), and 1,4-diazabicyclo[2.2.2]octane (7.19 g) was added thereto at 55° C.-65° C. The mixture was cooled to 0° C.-10° C., and the crystals were collected by filtration, and washed twice with ethyl acetate (90 mL) to give the title compound (21.7 g) as pale-yellow crystals.

$^1$H NMR (600 MHz, DMSO-d6) δ 2.21 (s, 3H), 2.81 (s, 12H), 4.14 (s, 2H), 6.49-6.57 (m, 1H), 7.28 (br d, J=8.69 Hz, 2H), 7.47 (s, 1H), 7.73 (d, J=1.13, 1H), 7.78 (br d, J=8.69 Hz, 2H), 8.46 (d, J=2.27, 1H), 8.64 (br s, 1H).

Example 7

Synthesis of 1,5-anhydro-2,4-dideoxy-2-(4-fluoro-5-methyl-1-oxo-6-(4-(1H-pyrazol-1-yl)benzyl)-1,3-dihydro-2H-isoindol-2-yl)-L-threo-pentitol To a solution of 3-fluoro-2-formyl-4-methyl-5-[4-(1H-pyrazol-1-yl)benzyl]benzoic acid 1,4-diazabicyclo[2.2.2] octane salt (15.0 g) and 2-amino-1,5-anhydro-2,4-dideoxy-L-threo-pentitol (4.1 g) in tetrahydrofuran (150 mL) was added acetic acid (15 mL). The mixture was stirred at 15° C.-35° C. for 15 min, and sodium triacetoxyborohydride (14.1 g) was added thereto at the same temperature. The mixture was stirred at 15° C.-35° C. for min, and warmed to 50° C.-60° C. The mixture was reacted at the same temperature for 2 hr, and cooled to 15° C.-35° C., and ethyl acetate (150 mL) was added thereto. To the mixture was added 2M hydrochloric acid (150 mL), and the mixture was subjected to liquid separation. To the aqueous layer was added ethyl acetate (75 mL), and the mixture was subjected to re-extraction. The organic layers were combined, washed successively with water (75 mL), 20% aqueous potassium carbonate solution (75 mL×2) and 5% aqueous ammonia (75 mL×2), and concentrated. To the concentrated residue were added ethanol (75 mL) and tetrahydrofuran (37.5 mL), and the mixture was heated to 55° C.-65° C. to dissolve the precipitated crystals. To the mixture was added slowly dropwise water (225 mL) at the same temperature. The mixture was cooled to 0° C.-10° C., and the crystals were collected by filtration, and washed twice with ethanol/water (1:2, 45 mL) to give the crude crystals (13.3 g) of the title compound as white crystals. To the crude 1,5-anhydro-2,4-dideoxy-2-(4-fluoro-5-methyl-1-oxo-6-(4-(1H-pyrazol-1-yl)benzyl)-1,3-dihydro-2H-isoindol-2-yl)-L-threo-pentitol (2.5 g) were added 2-butanone (22.5 mL) and dimethyl sulfoxide (2.5 mL). The mixture was heated to 65° C.-75° C. to dissolve the compound, and the insoluble substance was removed by filtration, and washed with 2-butanone (5 mL). To the mixture was added slowly dropwise n-heptane (25 mL) at 60° C.-70° C., and the mixture was stirred at the same temperature for 2 hr or more, which resulted in crystallization. To the mixture was added slowly dropwise n-heptane (25 mL) at 60° C.-70° C., and the mixture was stirred at the same temperature for 4 hr or more. The mixture was cooled to 0° C.-10° C., and the crystals were collected by filtration, and washed twice with 2-butanone/n-heptane (1:3, 7.5 mL) to give the recrystallized product (2.27 g) of the title compound as white crystals.

$^1$H NMR (600 MHz, CDCl3) δ 1.75-1.86 (m, 1H), 2.09-2.15 (m, 1H), 2.21 (br d, J=1.51 Hz, 3H), 2.76 (br d, J=5.29 Hz, 1H), 3.44-3.50 (m, 1H), 3.50-3.59 (m, 1H), 4.00-4.05 (m, 2H), 4.06-4.14 (m, 4H), 4.39 (br d, J=16.62 Hz, 1H), 4.56 (br d, J=17.00 Hz, 1H), 6.41-6.49 (m, 1H), 7.17 (br d, J=8.31 Hz, 2H), 7.46 (s, 1H), 7.59 (br d, J=8.69 Hz, 2H), 7.71 (d, J=1.13 Hz, 1H), 7.88 (d, J=1.89 Hz, 1H).

Example 8

Synthesis of 5-(4-(1H-pyrazol-1-yl)benzyl)-3-fluoro-2-formyl-N,N-diisopropyl-4-methylbenzamide using a flow reactor 5-(4-(1H-Pyrazol-1-yl)benzyl)-3-fluoro-2-formyl-N,N-diisopropyl-4-methylbenzamide was synthesized by generation of an aryl lithium species using by n-butyllithium, and the subsequent reaction with dimethylformamide, using a flow reactor shown in FIG. 1. Three tube reactors for precooling (P1, P2, P3; manufactured by GL Sciences, stainless tube, outside diameter 1/16 inch (1.58 mm), inside diameter 1.0 mm, length 500 mm) were connected to a flow reactor consisting of two T-shaped micromixers (M1, M2; manufactured by GL Sciences, stainless SUS Tee) and a tube reactor (R1; manufactured by GL Sciences, stainless tube, outside diameter 1/16 inch (1.58 mm), inside diameter 1.0 mm, length 30 mm) to construct a flow system for reaction. This was put into a thermostat bath set at minus 50° C. The solutions to be supplied from three tube reactors for pre-cooling (P1, P2, P3) were each sucked up using gas-tight syringe, and each supplied from the reactor to T-shaped mixer used for each step, using a syringe pump manufactured by ISIS Co., Ltd., at a given flow rate.

In the first reaction, (1) a solution (0.2M) prepared by diluting 3-(4-(1H-pyrazol-1-yl)benzyl)-5-fluoro-N,N-diisopropyl-4-methylbenzamide with THF, from tube reactor P1, and (2) commercially available 1.6M n-butyllithium from tube reactor P2 were each supplied to T-shaped mixer M1 (inside diameter 500 µm) at a flow rate of 32 mL/min (6.4 mmol/min) for (1) and 4.8 mL/min (7.68 mmol/min) for (2). In the second reaction, dimethylformamide (neat) was supplied from tube reactor P3 to T-shaped mixer M2 (inside diameter 1000 µm) at a flow rate of 16 mL/min, and thereby, the dimethylformamide was reacted with the aryl lithium intermediate generated in tube type reactor R1 via T-shaped mixer M1 in the first reaction. The residence time in tube type reactor R1 was 0.038 min. After the start of the syringe pumping, for several seconds until the flow became stable, the reaction solution from the flow reactor was not collected. For 10 sec after the flow became stable, the reaction solution from the flow reactor was collected. The obtained reaction solution was analyzed by HPLC (LC-2010C HT manufactured by Shimadzu Corporation, column; YMC-Pack ODS-A 150×4.6 mm (S-5 µm, 12 nm), acetonitrile/0.01M aqueous potassium dihydrogenphosphate solution mobile phase (gradient elution program: constant at A=B=50% for 0 to 15 min, gradually changed to A=80 B=20 for 15 to 30 min, constant at A=80 B=20 for 30 to 45 min, constant at A=B=50% for 45 to 60 min), 1.0 mL/min, UV detector 25° C.). From the result of the analysis, it was confirmed that 5-(4-(1H-pyrazol-1-yl)benzyl)-3-fluoro-2-formyl-N,N-diisopropyl-4-methylbenzamide (HPLC retention time 17.1 min) was produced in 96.2% area normalization.

Example 9

Synthesis of 5-(4-(1H-pyrazol-1-yl)benzyl)-3-fluoro-2-formyl-N,N-diisopropyl-4-methylbenzamide using a flow reactor and Isolation 5-(4-(1H-Pyrazol-1-yl)benzyl)-3-fluoro-2-formyl-N,N-diisopropyl-4-methylbenzamide was synthesized by generation of an aryl lithium species using n-butyllithium, and the subsequent reaction with dimethylformamide, using a flow reactor shown in FIG. 2. Three tube reactors for precooling (P1, P2, P3; manufactured by GL Sciences, stainless tube, outside diameter 1/16 inch (1.58 mm), inside diameter 1.0 mm, length 500 mm) were connected to a flow reactor consisting of two T-shaped micromixers (M1, M2; manufactured by GL Sciences, stainless SUS Tee) and a tube reactor (R1; manufactured by GL Sciences, stainless tube, outside diameter 1/16 inch (1.58 mmn), inside diameter 1.0 mm, length 30 mm) to construct a flow system for reaction. This was put into a thermostat bath set at minus 50° C. The solutions to be supplied from three tube reactors for pre-cooling (P1, P2, P3) were each sucked up using gas-tight syringe, and each supplied from the reactor to T-shaped mixer used for each step, using a syringe pump manufactured by ISIS Co., Ltd., at a given flow rate.

In the first reaction, (1) a solution (0.2M) prepared by diluting 3-(4-(1H-pyrazol-1-yl)benzyl)-5-fluoro-N,N-diisopropyl-4-methylbenzamide with THF, from tube reactor P1, and (2) commercially available 1.6M n-butyllithium from tube reactor P2 were each supplied to T-shaped mixer M1 (inside diameter 500 µm) at a flow rate of 32 mL/min (6.4 mmol/min) for (1) and 12 mL/min (19.2 mmol/min) for (2). In the second reaction, dimethylformamide (neat) was supplied from tube reactor P3 to T-shaped mixer M2 (inside diameter 1000 µm) at a flow rate of 16 mL/min, and thereby, the dimethylformamide was reacted with the aryl lithium intermediate generated in tube type reactor R1 via T-shaped mixer M1 in the first reaction. The residence time in tube type reactor R1 was 0.032 sec. After the start of the syringe pumping, for several seconds until the flow became stable, the reaction solution from the flow reactor was not collected. For 10 sec after the flow became stable, the reaction solution from the flow reactor was collected. The obtained reaction solution was quenched with 1M hydrochloric acid (67.5 mL), ethyl acetate (45 mL) was added thereto, and the mixture was subjected to liquid separation. To the organic layer was added 10 w/w % brine (45 mL), and the mixture was subjected to liquid separation. The organic layer was analyzed by HPLC (LC-2010C HT manufactured by Shimadzu Corporation, column; YMC-Pack ODS-A 150×4.6 mm (S-5 µm, 12 nm), acetonitrile/0.01M aqueous potassium dihydrogenphosphate solution mobile phase (gradient elution program: constant at A=B=50% for 0 to 15 min, gradually changed to A=80 B=20 for 15 to 30 min, constant at A=80 B=20 for 30 to 45 min, constant at A=B=50% for 45 to 60 min), 1.0 mL/min, UV detector 25° C.). From the result of the analysis, it was confirmed that 5-(4-(1H-pyrazol-1-yl)benzyl)-3-fluoro-2-formyl-N,N-diisopropyl-4-methylbenzamide (HPLC retention time 17.1 min) was produced in 92.8% area normalization. This organic layer was concentrated (1st concentration), ethyl acetate (45 mL) was added thereto, and the mixture was concentrated (2nd concentration). Then, to this concentrate was added ethyl acetate (45 mL), and the mixture was concentrated (3rd concentration). To the concentrate was added ethyl acetate (18 mL), and the mixture was warned to 77° C. to dissolved the precipitate (5-(4-(1H-pyrazol-1-yl)benzyl)-3-fluoro-2-formyl-N,N-diisopropyl-4-methylbenzamide). The mixture was stirred at 60° C.-70° C., and n-heptane (37.8 mL) was added dropwise thereto over 1 hr. The precipitation of grayish white crystals was confirmed. The mixture was stirred at 60° C.-70° C. for 1 hr, and cooled to room temperature, and stirred overnight. Then, the mixture was cooled to 0° C.-10° C., stirred for 3 hr for aging, and filtered with glass filter to isolate crystals. The crystals were washed with a mixed solution (7.5 mL) of ethyl acetate/n-heptane-1/3, and dried in a vacuum dryer for 2 hr while heating at 50° C. to give grayish white crystals (3.64 g) (isolated yield 90%).

Example 10

Synthesis of 3-fluoro-2-formyl-4-methyl-N,N-di(propan-2-yl)-5-[4-(1H-pyrazol-1-yl)benzyl]benzamide Under nitrogen atmosphere, at 20° C.-30° C., a solution of 3-fluoro-4-methyl-N,N-di(propan-2-yl)-5-[4-(1H-pyrazol-1-yl)benzyl]benzamide (10.0 g) in tetrahydrofuran (140 mL) was cooled to −10° C.-0° C., and 1.0M 2,2,6,6-tetramethylpiperidinomagnesium chloride-lithium chloride tetrahydrofuran/toluene solution (1:1, 43.2 mL) was added dropwise thereto. The mixture was stirred at −10° C.-0° C. for 10 min, and a solution of N,N-dimethylformamide (4.89 mL) in tetrahydrofuran (5 mL) was added dropwise thereto. The mixture was stirred at −10° C.-0° C. for 10 min, and 2M hydrochloric acid (100 mL) was added dropwise thereto at the temperature not exceeding 30° C. To the mixture was added ethyl acetate (50 mL), and the mixture was subjected to liquid separation. To the separated aqueous layer was added ethyl acetate (50 mL), and the mixture was subjected to re-extraction. The combined organic layer was washed successively with (1) 2M hydrochloric acid (50 mL×2), (2) 20% aqueous potassium carbonate solution (50 mL) and (3) 10% brine (50 mL), and concentrated. To the concentrated residue was added ethyl acetate (70 mL), and n-heptane (100 mL) was added slowly dropwise thereto at 60° C.-70° C. The mixture was cooled to 0° C.-10° C., and the crystals were collected by filtration, and washed twice with ethyl acetate/n-heptane (1:3, 20 mL) to give the title compound (9.70 g) as white-pale gray crystals.

Example 11

Synthesis of tert-butyl 3-fluoro-4-methyl-5-[4-(1H-pyrazol-1-yl)benzyl]benzoate tert-Butyl-3-fluoro-5-{hydroxy[4-(1H-pyrazol-1-yl)phenyl]methyl}-4-methylbenzoate (200 mg) was added to tetrahydrofuran/methanol (1:1, 6 mL), and the mixture was subjected to decompression and nitrogen substitution three times. To the mixture was added 20 wt % palladium hydroxide (20 mg), and the mixture was subjected to decompression and hydrogen substitution three times. The reaction was carried out under hydrogen atmosphere at 40° C. for 8 hr. The mixture was cooled to room temperature, the catalyst was removed by filtration, and the filtrate was concentrated. To the concentrated residue was added methanol (2 mL), and water (4 mL) was added slowly dropwise thereto at 35° C.-45° C. The mixture was cooled to room temperature, and the crystals were collected by filtration, and washed with methanol/water (1:3) to give the title compound (168 mg) as white crystals.

Example 12

Synthesis of tert-butyl 3-fluoro-5-{hydroxy[4-(1H-pyrazol-1-yl)phenyl]methyl}-4-methylbenzoate tert-Butyl 3-fluoro-5-iodo-4-methylbenzoate (10 g) was dissolved in tetrahydrofuran (100 mL), and the solution was cooled to −12° C.-−4° C. Isopropylmagnesium chloride-lithium chloride tetrahydrofuran solution (1.34 M, 34.4 mL) was added dropwise thereto over 30 min at −5° C.-−15° C. The mixture was reacted at −5° C.-−15° C. for 2 hr, and isopropylmagnesium chloride-lithium chloride tetrahydrofuran solution (1.34 M, 5.5 mL) Was again added thereto. The mixture was stirred at −5° C.-−15° C. for 30 min, and a solution prepared by dissolving 4-(1H-pyrazol-1-yl)benzaldehyde (5.25 g) in tetrahydrofuran (30 mL) was added dropwise thereto over 30 min. The mixture was stirred at −5° C.-−15° C. for 30 min, ethyl acetate (200 mL) and 1M hydrochloric acid (100 mL) were added thereto, and the mixture was subjected to liquid separation. The organic layer was washed twice with 10% brine (50 mL), and subjected to liquid separation. To the concentrated residue were added tetrahydrofuran (100 mL) and activated carbon (1 g), and the mixture was stirred at room temperature for 30 min. The activated carbon was removed by filtration. The filtrate was concentrated, and to the concentrated residue was added ethyl acetate (50 mL). To the mixture was added slowly dropwise n-heptane (50 mL) at 40° C. The mixture was cooled to room temperature, and the crystals were collected by filtration, and washed with ethyl acetate/n-heptane (1:3, 40 mL) to give the title compound (9.82 g) as white crystals.

$^1$H NMR (600 MHz, CDCl3) δ 1.58-1.60 (m, 9H), 2.15 (d, J=1.9 Hz, 3H), 2.46 (d, J=4.2 Hz, 1H), 6.02 (d, J=3.8 Hz, 1H), 6.46 (t, J=2.1 Hz, 1H), 7.38 (m, J=8.7 Hz, 2H), 7.59 (dd, J=9.8, 1.5 Hz, 1H), 7.66 (m, J=8.7 Hz, 2H), 7.72 (d, J=1.5 Hz, 1H), 7.90 (d, J=2.6 Hz, 1H), 8.03 (s, 1H).

Example 13

Synthesis of tert-butyl 3-fluoro-4-methyl-5-[4-(1H-pyrazol-1-yl)benzyl]benzoate tert-Butyl-3-fluoro-5-{hydroxy[4-(1H-pyrazol-1-yl)phenyl]methyl}-4-methylbenzoate (200 mg) was added to tetrahydrofuran (1 mL), and triethylamine (159 mg), 4-dimethylaminopyridine (12.8 mg) and acetic anhydride (107 mg) were added thereto. The mixture was reacted at 50° C. for 1 hr, and cooled to room temperature. To the mixture was added methanol (1 mL), and the mixture was subjected to decompression and nitrogen substitution three times. To the mixture was added 10% Pd/C (PE type, 20 mg), and the mixture was subjected to decompression and hydrogen substitution three times. The reaction was carried out under hydrogen atmosphere at 40° C. for 3 hr. The mixture was cooled to room temperature, the catalyst was removed by filtration, and the filtrate was concentrated. To the concentrated residue was added methanol (1 mL), and water (1 mL) was added slowly dropwise thereto. The crystals were collected by filtration, and washed with methanol/water (1:3) to give the title compound (178 mg) as white crystals.

$^1$H NMR (600 MHz, CDCl3) δ 1.58 (s, 9H), 2.17 (d, J=2.3 Hz, 3H), 4.07 (s, 2H), 6.39-6.51 (m, 1H), 7.17 (d, J-8.7 Hz, 2H), 7.54 (dd, J=9.8, 1.5 Hz, 1H), 7.58-7.62 (m, 2H), 7.62 (s, 1H), 7.71 (d, J=1.5 Hz, 1H), 7.88 (d, J=2.6 Hz, 1H).

Example 14

Synthesis of 3-fluoro-2-formyl-4-methyl-5-[4-(1H-pyrazol-1-yl)benzyl]benzoic acid 1,4-diazabicyclo [2.2.2]octane salt tert-Butyl 3-fluoro-4-methyl-5-[4-(1H-pyrazol-1-yl)benzyl]benzoate (3 g) was dissolved in tetrahydrofuran (36 mL), and the solution was cooled to 0° C.-−10° C. To the mixture was added slowly dropwise 1.0M 2,2,6,6-tetramethylpiperidinomagnesium chloride-lithium chloride tetrahydrofuran/toluene solution (1:1, 14.7 mL, 1.8 eq.) at 0° C.-−10° C. The mixture was washed with tetrahydrofuran (1.5 mL), and the mixture was stirred at 0° C.-−10° C. for about 1 hr. A solution of 4-formylmorpholine (2.1 mL, 2.5 eq.) in tetrahydrofuran (3 mL) was added dropwise to the mixture at −10° C.-0° C., the used container was washed with tetrahydrofuran (1.5 mL). The mixture was stirred at −10° C.-0° C. for about 1 hr, and 6 M hydrochloric acid (36 mL) was added thereto at the temperature not exceeding 30° C. The mixture was stirred overnight at room temperature, toluene (30 mL) was added thereto, and the mixture was subjected to liquid separation. The aqueous layer was subjected to extraction with toluene/tetrahydrofuran (15 mL/15 mL). The combined organic layer was washed successively with (1) 2M hydrochloric acid (15 mL), (2) 10% brine (15 mL, twice) and (3) water (15 mL). To the organic layer was added activated carbon (300 mg), and the mixture was stirred at room temperature for 30 min. The activated carbon was removed by filtration, and washed with tetrahydrofuran (9 mL×3).

The filtrate was concentrated, and to the concentrated residue were added ethyl acetate (15 mL) and tetrahydrofuran (6 mL). To the mixture was added DABCO (827 mg, 0.9 eq) at 55° C., and the mixture was stirred at 50° C.-60° C. for 1 hr. The mixture was cooled to 5° C., and the crystals were collected by filtration, and washed with ethyl acetate (9 mL×2) to give the title compound (2.51 g) as pale-yellow crystals.

$^1$H NMR (600 MHz, DMSO-d6) δ 2.21 (s, 3H), 2.81 (s, 12H), 4.14 (s, 2H), 6.49-6.57 (m, 1H), 7.28 (br d, J=8.69 Hz, 2H), 7.47 (s, 1H), 7.73 (d, J=1.13, 1H), 7.78 (br d, J=8.69 Hz, 2H), 8.46 (d, J=2.27, 1H), 8.64 (br s, 1H).

Example 15

Synthesis of 3-fluoro-4-methyl-N,N-di(propan-2-yl)-5-[4-(H-pyrazol-1-yl)benzyl]benzamide Under nitrogen atmosphere, at 5° C., to a solution of 3-fluoro-5-iodo-4-methyl-N,N-di(propan-2-yl)benzamide (5 g) in tetrahydrofuran (25 mL) was added dropwise 1.34M isopropylmagnesium chloride-lithium chloride tetrahydrofuran solution (15.9 mL). The mixture was stirred at 5° C. for 30 min, and tetrahydrofuran solution (20 mL) of 4-(1H-pyrazol-1-yl)benzaldehyde (2.19 g) was added thereto. The mixture was stirred at 5° C. for 1 hr, and 2M hydrochloric acid (50 mL) was added dropwise to the reaction mixture at the temperature not exceeding 35° C. To the mixture was added ethyl acetate (50 mL), and the mixture was subjected to liquid separation. To the aqueous layer was added ethyl acetate (25 mL), and the mixture was subjected to re-extraction. The organic layers were combined, and washed successively with 2M hydrochloric acid (25 mL), water (25 mL), 20% aqueous potassium carbonate solution (25 mL), water (25 mL) and 20% brine (25 mL). To the organic layer was added activated carbon (1.0 g), and the mixture was stirred at room temperature for 1 hr. The activated carbon was removed by filtration, and washed three times with ethyl acetate (15 mL), and the filtrate and washing were concentrated. To the concentrated residue was added ethanol (50 mL), and the mixture was subjected to decompression and nitrogen substitution three times. To the mixture was added 20 wt % palladium hydroxide (1.50 g), and the mixture was subjected to decompression and nitrogen substitution by hydrogen gas (0.5 mPa). Under hydrogen atmosphere, the mixture was reacted at 50° C.-60° C. for 39 hr. The mixture was subjected to nitrogen substitution three times, and cooled to 20° C.-30° C. Tetrahydrofuran (10 mL) was added thereto, and the insoluble substance was removed by filtration. The mixture was washed three times with ethanol (15 mL), and concentrated. To the concentrated residue was added ethanol (40 mL), and water (50 mL) was added slowly dropwise thereto at 60° C.-70° C. The mixture was cooled to 20° C.-30° C., and the crystals were collected by filtration, and washed twice with ethanol/water (2:3, 15 mL). To the wet crystals was added ethyl acetate (15 mL), and n-heptane (30 mL) was added slowly dropwise thereto at 45° C.-55° C. The mixture was cooled to 0° C.-10° C., and the crystals were collected by filtration, and washed twice with ethyl acetate/n-heptane (1:4, 10 mL) to give the title compound (3.50 g) as white crystals.

Example 16

Synthesis of 3-fluoro-4-methyl-N,N-di(propan-2-yl)-5-[4-(1H-pyrazol-1-yl)benzyl]benzamide 3-Fluoro-4-methyl-N,N-di(propan-2-yl)-5-{hydroxy[4-(1H-pyrazol-1-yl)phenyl]methyl}benzamide (100 mg) was added to tetrahydrofuran (1 mL), and triethylamine (74.1 mg), 4-dimethylaminopyridine (6.0 mg) and acetic anhydride (49.9 mg) were added thereto. The mixture was reacted at 50° C. for 1 hr, and cooled to room temperature. To the mixture was added methanol (1 mL), and the mixture was subjected to decompression and nitrogen substitution three times. To the mixture was added 10% Pd/C(PE type, 10 mg), and the mixture was subjected to decompression and hydrogen substitution three times. The mixture was reacted under hydrogen atmosphere, at 40° C. for 3 hr reaction. The mixture was cooled to room temperature, and the catalyst was removed by filtration. The mixture was washed three times with methanol (1 mL), and concentrated. To the concentrated residue was added methanol (1 mL), and water (1 mL) was added slowly dropwise thereto. The crystals were collected by filtration, and washed twice with methanol/water (1:3) to give the title compound (69.1 mg) as white crystals.

INDUSTRIAL APPLICABILITY

According to the present invention, 1,5-anhydro-2,4-dideoxy-2-(4-fluoro-5-methyl-1-oxo-6-(4-(1H-pyrazol-1-yl)benzyl)-1,3-dihydro-2H-isoindol-2-yl)-L-threo-pentitol, which is useful for the prophylaxis and/or treatment of Alzheimer's disease and the like, can produced without using a highly poisonous reagent, in an efficient way (e.g., in short steps, in high-yield, in a highly selective manner).

This application is based on patent application No. 2017-36898 filed in Japan, the contents of which are encompassed in full herein.

The invention claimed is:

1. A method of producing 1,5-anhydro-2,4-dideoxy-2-(4-fluoro-5-methyl-1-oxo-6-(4-(1H-pyrazol-1-yl)benzyl)-1,3-dihydro-2H-isoindol-2-yl)-L-threo-pentitol or a salt thereof, which comprises reacting 4-fluoro-3-hydroxy-5-methyl-6-[4-(1H-pyrazol-1-yl)benzyl]-2-benzofuran-1(3H)-one or a salt thereof, 3-fluoro-2-formyl-4-methyl-5-[4-(1H-pyrazol-1-yl)benzyl]benzoic acid or a salt thereof, or a mixture thereof with 2-amino-1,5-anhydro-2,4-dideoxy-L-threo-pentitol.

2. A method of producing 4-fluoro-3-hydroxy-5-methyl-6-[4-(1H-pyrazol-1-yl)benzyl]-2-benzofuran-1(3H)-one or a salt thereof, 3-fluoro-2-formyl-4-methyl-5-[4-(1H-pyrazol-1-yl)benzyl]benzoic acid or a salt thereof, or a mixture thereof, which comprises subjecting a compound represented by the formula (I)

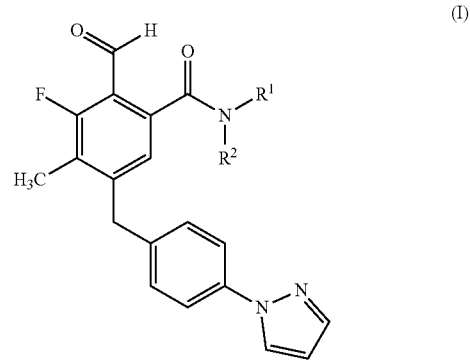

(I)

wherein

R$^1$ and R$^2$ are each independently a hydrogen atom or an optionally substituted hydrocarbon group, or R¹ and R² form, together with the adjacent nitrogen atom, a 3- to 8-membered monocyclic nitrogen-containing non-aromatic heterocycle, or a salt thereof, to a hydrolysis reaction.

3. A method of producing a compound represented by the formula (I)

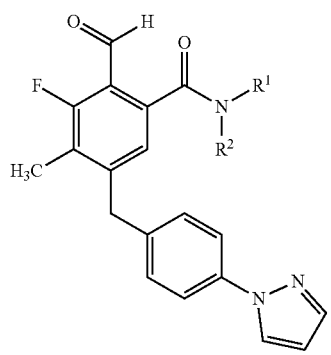

(I)

wherein

R¹ and R² are each independently a hydrogen atom or an optionally substituted hydrocarbon group, or R¹ and R² form, together with the adjacent nitrogen atom, a 3- to 8-membered monocyclic nitrogen-containing non-aromatic heterocycle, or a salt thereof, which comprises subjecting a compound represented by the formula (II)

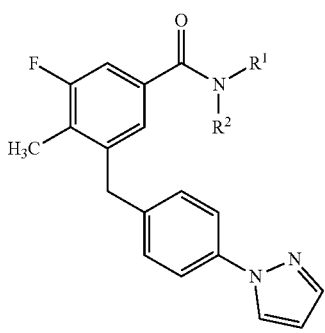

(II)

wherein each symbol is as defined above, or a salt thereof, to a formylation reaction.

4. A method of producing 4-fluoro-3-hydroxy-5-methyl-6-[4-(1H-pyrazol-1-yl)benzyl]-2-benzofuran-1(3H)-one or a salt thereof, 3-fluoro-2-formyl-4-methyl-5-[4-(1H-pyrazol-1-yl)benzyl]benzoic acid or a salt thereof, or a mixture thereof, which comprises Step (i): a step of subjecting a compound represented by the formula (II)

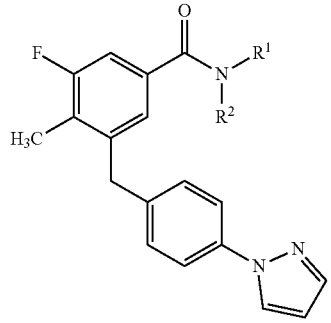

(II)

wherein

R¹ and R² are each independently a hydrogen atom or an optionally substituted hydrocarbon group, or R¹ and R² form, together with the adjacent nitrogen atom, a 3- to 8-membered monocyclic nitrogen-containing non-aromatic heterocycle, or a salt thereof, to a formylation reaction to obtain a compound represented by the formula (I)

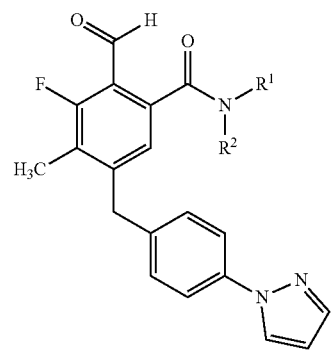

(I)

wherein each symbol is as defined above, or a salt thereof, and

Step (ii): a step of subjecting the compound represented by the formula (I) or a salt thereof, to a hydrolysis reaction.

5. A method of producing 1,5-anhydro-2,4-dideoxy-2-(4-fluoro-5-methyl-1-oxo-6-(4-(1H-pyrazol-1-yl)benzyl)-1,3-dihydro-2H-isoindol-2-yl)-L-threo-pentitol or a salt thereof, which comprises Step (i): a step of subjecting a compound represented by the formula (II)

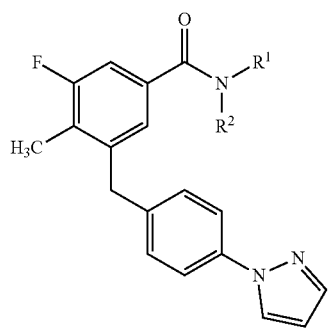

(II)

wherein

R¹ and R² are each independently a hydrogen atom or an optionally substituted hydrocarbon group, or R¹ and R² form, together with the adjacent nitrogen atom, a 3- to 8-membered monocyclic nitrogen-containing non-aromatic heterocycle,
or a salt thereof, to a formylation reaction to obtain a compound represented by the formula (I)

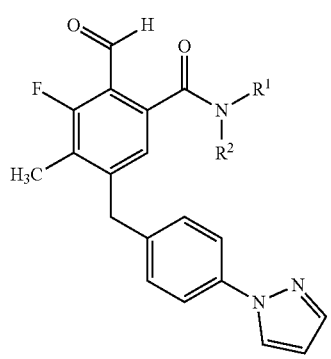

(I)

wherein each symbol is as defined above,
or a salt thereof,
Step (ii): a step of subjecting the compound represented by the formula (I) or a salt thereof to a hydrolysis reaction to obtain 4-fluoro-3-hydroxy-5-methyl-6-[4-(1H-pyrazol-1-yl)benzyl]-2-benzofuran-1(3H)-one or a salt thereof, 3-fluoro-2-formyl-4-methyl-5-[4-(1H-pyrazol-1-yl)benzyl]benzoic acid or a salt thereof, or a mixture thereof, and
Step (iii): a step of reacting the obtained 4-fluoro-3-hydroxy-5-methyl-6-[4-(1H-pyrazol-1-yl)benzyl]-2-benzofuran-1 (3H)-one or a salt thereof, 3-fluoro-2-formyl-4-methyl-5-[4-(1H-pyrazol-1-yl)benzyl]benzoic acid or a salt thereof, or a mixture thereof with 2-amino-1,5-anhydro-2,4-dideoxy-L-threo-pentitol.

6. 4-Fluoro-3-hydroxy-5-methyl-6-[4-(1H-pyrazol-1-yl)benzyl]-2-benzofuran-1(3H)-one or a salt thereof.

7. 3-Fluoro-2-formyl-4-methyl-5-[4-(1H-pyrazol-1-yl)benzyl]benzoic acid or a salt thereof.

8. 3-Fluoro-2-formyl-4-methyl-N,N-di(propan-2-yl)-5-[4-(1H-pyrazol-1-yl)benzyl]benzamide or a salt thereof.

9. 3-Fluoro-4-methyl-N,N-di(propan-2-yl)-5-[4-(1H-pyrazol-1-yl)benzyl]benzamide or a salt thereof.

10. A method of producing 4-fluoro-3-hydroxy-5-methyl-6-[4-(1H-pyrazol-1-yl)benzyl]-2-benzofuran-1(3H)-one or a salt thereof, 3-fluoro-2-formyl-4-methyl-5-[4-(1H-pyrazol-1-yl)benzyl]benzoic acid or a salt thereof, or a mixture thereof, which comprises subjecting a compound represented by the formula (VIII)

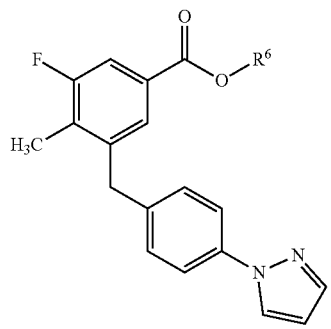

(VIII)

wherein R⁶ is a hydrogen atom or an optionally substituted $C_{1-6}$ alkyl group,
or a salt thereof, to a formylation reaction, and then a hydrolysis reaction, if desired.

11. A method of producing a compound represented by the formula (VIII)

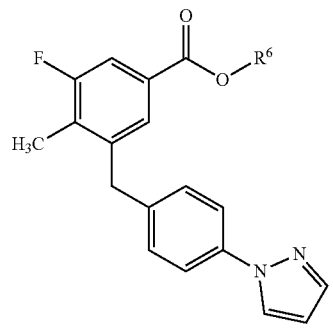

(VIII)

wherein R⁶ is a hydrogen atom or an optionally substituted $C_{1-6}$ alkyl group,
or a salt thereof, which comprises subjecting a compound represented by the formula (IX)

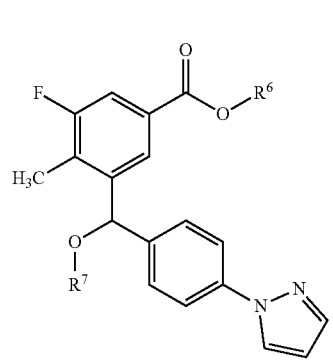

(IX)

wherein
R⁶ is as defined above, and
R⁷ is a protecting group,
or a salt thereof, to a reduction reaction.

12. A method of producing a compound represented by the formula (IX)

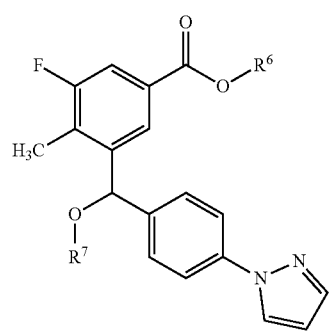

(IX)

wherein

R⁶ is a hydrogen atom or an optionally substituted $C_{1-6}$ alkyl group, and

R⁷ is a protecting group, or a salt thereof, which comprises subjecting a compound represented by the formula (X)

(X)

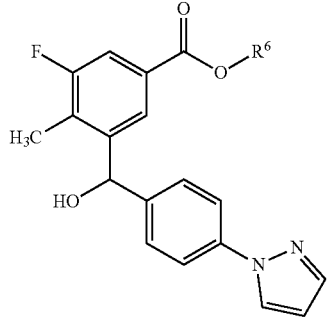

wherein R⁶ is as defined above, or a salt thereof, to a protection reaction of the hydroxy group.

13. A method of producing a compound represented by the formula (X)

(X)

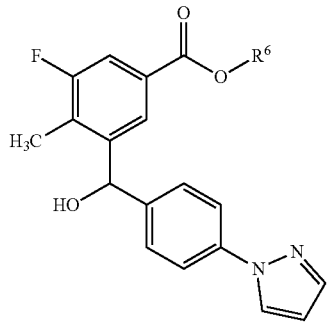

wherein R⁶ is a hydrogen atom or an optionally substituted $C_{1-6}$ alkyl group, or a salt thereof, which comprises reacting a compound represented by the formula (XI)

(XI)

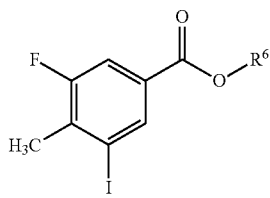

wherein the symbol is as defined above, or a salt thereof, with 4-(1H-pyrazol-1-yl)benzaldehyde.

14. A method of producing a compound represented by the formula (IX)

(IX)

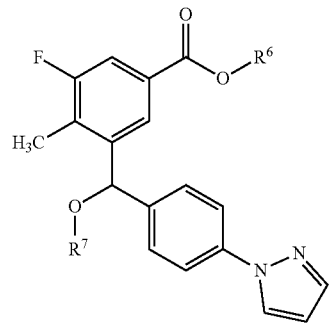

wherein

R⁶ is a hydrogen atom or an optionally substituted $C_{1-6}$ alkyl group, and

R⁷ is a protecting group, or a salt thereof, which comprises

Step (i): a step comprising reacting a compound represented by the formula (XI)

(XI)

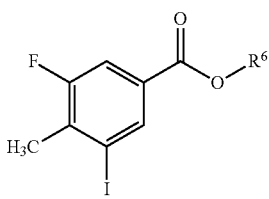

wherein R⁶ is as defined above, or a salt thereof, with 4-(1H-pyrazol-1-yl)benzaldehyde to obtain a compound represented by the formula (X)

(X)

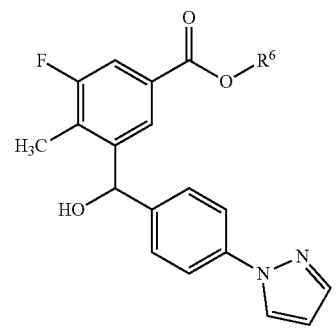

wherein the symbol is as defined above, or a salt thereof, and

Step (ii): a step of subjecting the compound represented by the formula (X) or a salt thereof, to a protection reaction of the hydroxy group.

15. A method of producing a compound represented by the formula (VIII)

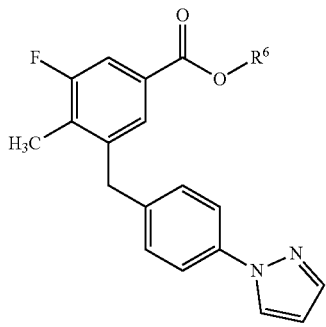

(VIII)

wherein R⁶ is a hydrogen atom or an optionally substituted $C_{1-6}$ alkyl group,
or a salt thereof, which comprises
Step (i): a step of reacting a compound represented by the formula (XI)

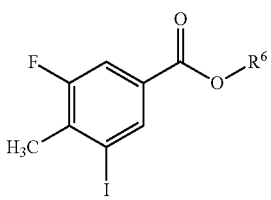

(XI)

wherein R⁶ is as defined above,
or a salt thereof, with 4-(1H-pyrazol-1-yl)benzaldehyde to obtain a compound represented by the formula (X)

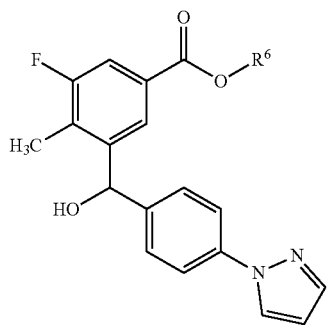

(X)

wherein the symbol is as defined above,
or a salt thereof,
Step (ii): a step of subjecting the compound represented by the formula (X) or a salt thereof to a protection reaction of the hydroxy group to obtain a compound represented by the formula (IX)

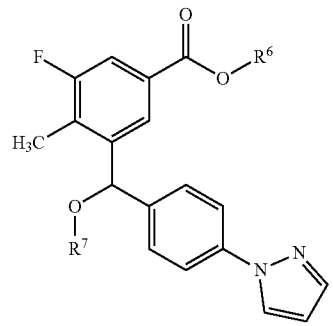

(IX)

wherein
R⁶ is as defined above, and
R⁷ is a protecting group,
or a salt thereof, and
Step (iii): a step of subjecting the compound represented by the formula (IX) or a salt thereof, to a reduction reaction.

16. A method of producing 4-fluoro-3-hydroxy-5-methyl-6-[4-(1H-pyrazol-1-yl)benzyl]-2-benzofuran-1(3H)-one or a salt thereof, 3-fluoro-2-formyl-4-methyl-5-[4-(1H-pyrazol-1-yl)benzyl]benzoic acid or a salt thereof, or a mixture thereof, which comprises
Step (i): a step of reacting a compound represented by the formula (XI)

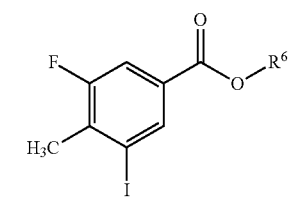

(XI)

wherein R⁶ is a hydrogen atom or an optionally substituted $C_{1-6}$ alkyl group,
or a salt thereof, with 4-(1H-pyrazol-1-yl)benzaldehyde to obtain a compound represented by the formula (X)

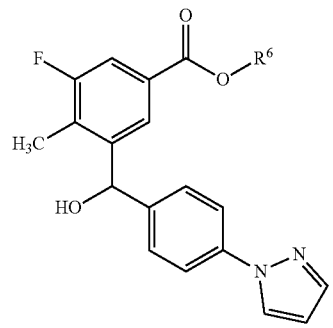

(IX)

wherein the symbol is as defined above,
or a salt thereof,
Step (ii): a step of subjecting the compound represented by the formula (X) or a salt thereof to a protection reaction of the hydroxy group to obtain a compound represented by the formula (IX)

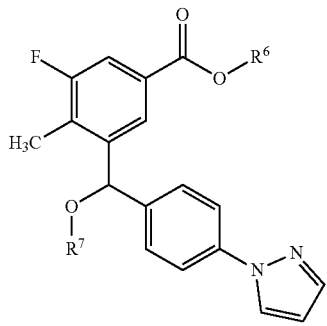

(IX)

wherein
R⁶ is as defined above, and
R⁷ is a protecting group,
or a salt thereof,
Step (iii): a step of subjecting the compound represented by the formula (IX) or a salt thereof to a reduction reaction to obtain a compound represented by the formula (VIII)

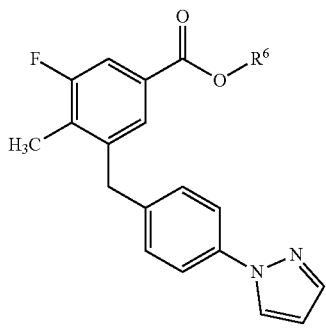

(VIII)

wherein the symbol is as defined above,
or a salt thereof, and
Step (iv): a step of subjecting the compound represented by the formula (VIII) or a salt thereof to a formylation reaction, and then a hydrolysis reaction, if desired.

17. A method of producing 1,5-anhydro-2,4-dideoxy-2-(4-fluoro-5-methyl-1-oxo-6-(4-(1H-pyrazol-1-yl)benzyl)-1,3-dihydro-2H-isoindol-2-yl)-L-threo-pentitol or a salt thereof, which comprises Step (i): a step comprising reacting a compound represented by the formula (XI)

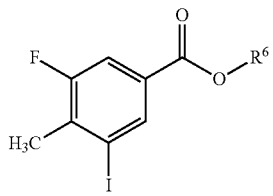

(XI)

wherein R⁶ is a hydrogen atom or an optionally substituted $C_{1-6}$ alkyl group,
or a salt thereof, with 4-(1H-pyrazol-1-yl)benzaldehyde to obtain a compound represented by the formula (X)

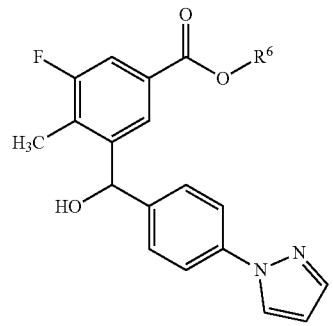

(IX)

wherein the symbol is as defined above,
or a salt thereof,
Step (ii): a step of subjecting the compound represented by the formula (X) or a salt thereof to a protection reaction of the hydroxy group to obtain a compound represented by the formula (IX)

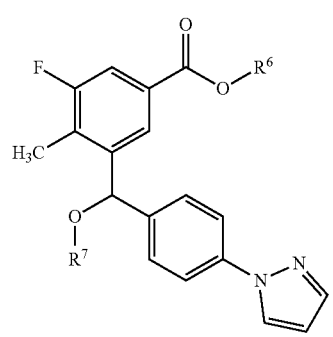

(IX)

wherein
R⁶ is as defined above, and
R⁷ is a protecting group,
or a salt thereof,
Step (iii): a step of subjecting the compound represented by the formula (IX) or a salt thereof to a reduction reaction to obtain a compound represented by the formula (VIII)

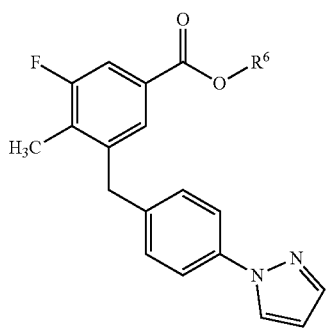

(VIII)

wherein the symbol is as defined above,
or a salt thereof,
Step (iv): a step of subjecting the compound represented by the formula (VIII) or a salt thereof to a formylation reaction, and then a hydrolysis reaction, if desired, to obtain 4-fluoro-3-hydroxy-5-methyl-6-[4-(1H-pyrazol-1-yl)benzyl]-2-benzofuran-1(3H)-one or a salt thereof, 3-fluoro-2-formyl-4-methyl-5-[4-(1H-pyrazol-1-yl)benzyl]benzoic acid or a salt thereof, or a mixture thereof, and Step (v): a step of reacting 4-fluoro-3-hydroxy-5-methyl-6-[4-(1H-pyrazol-1-yl)benzyl]-2-benzofuran-1(3H)-one or a salt thereof, 3-fluoro-2-formyl-4-methyl-5-[4-(1H-pyrazol-1-yl)benzyl]benzoic acid or a salt thereof, or a mixture thereof with 2-amino-1,5-anhydro-2,4-dideoxy-L-threo-pentitol.

* * * * *